(12) United States Patent
Smith et al.

(10) Patent No.: US 7,049,313 B2
(45) Date of Patent: May 23, 2006

(54) ATM INHIBITORS

(75) Inventors: Graeme Cameron Murray Smith, Cambridge (GB); Niall Morrison Barr Martin, Cambridge (GB); Stephen Philip Jackson, Cambridge (GB); Mark James O'Connor, Cambridge (GB); Alan Yin Kai Lau, Cambridge (GB); Xiao-Ling Fan Cockcroft, Horsham (GB); Ian Timothy Williams Matthews, Horsham (GB); Keith Allan Menear, Horsham (GB); Laurent Jean Martin Rigoreau, Horsham (GB); Marc Geoffery Hummersone, Horsham (GB); Roger John Griffin, Morpeth (GB)

(73) Assignee: Kudos Pharmaceuticals Ltd., (GB)

( * ) Notice: Subject to any disclaimer, the term of this patent is extended or adjusted under 35 U.S.C. 154(b) by 0 days.

(21) Appl. No.: 10/373,114

(22) Filed: Feb. 24, 2003

(65) Prior Publication Data
US 2004/0002492 A1 Jan. 1, 2004

Related U.S. Application Data

(60) Provisional application No. 60/360,493, filed on Feb. 28, 2002, provisional application No. 60/395,884, filed on Jul. 15, 2002.

(30) Foreign Application Priority Data
Feb. 25, 2002 (GB) .................... 0204350

(51) Int. Cl.
*A61K 31/535* (2006.01)
*C07D 413/00* (2006.01)
*A61P 35/00* (2006.01)

(52) U.S. Cl. .................. 514/231.5; 544/114; 544/145; 544/147

(58) Field of Classification Search ........... 544/114, 544/145, 147; 514/235.5, 231.5
See application file for complete search history.

(56) References Cited

U.S. PATENT DOCUMENTS

| | | | |
|---|---|---|---|
| 4,954,518 A | 9/1990 | Takano et al. | |
| 5,252,735 A | 10/1993 | Morris | |
| 5,284,856 A | 2/1994 | Naik et al. | |
| 5,302,613 A | 4/1994 | Morris | |
| 5,703,075 A * | 12/1997 | Gammill et al. ......... | 514/233.5 |
| 5,733,920 A | 3/1998 | Mansuri et al. | |
| 5,922,755 A | 7/1999 | Tanaka et al. | |
| 6,348,311 B1 | 2/2002 | Kastan et al. | |
| 6,387,640 B1 | 5/2002 | Kastan et al. | |
| 2004/0192687 A1 | 9/2004 | Martin et al. | |

FOREIGN PATENT DOCUMENTS

| | | |
|---|---|---|
| EP | 0 610 519 A1 | 8/1994 |
| EP | 0 635 268 A1 | 1/1995 |
| EP | 0 640 339 A1 | 3/1995 |
| EP | 0 641 566 A1 | 3/1995 |
| EP | 0 648 492 A2 | 4/1995 |
| EP | 0 658 343 A1 | 6/1995 |
| GB | 1303724 | 1/1973 |
| GB | 2 302 021 A | 1/1997 |
| JP | 03215-423 | 1/1990 |
| WO | WO 90/06921 | 6/1990 |
| WO | WO 91/19707 | 12/1991 |
| WO | WO 92/00290 | 1/1992 |
| WO | WO 95/29673 | 11/1995 |
| WO | WO 96/01108 | 1/1996 |
| WO | WO 97/15658 | 5/1997 |

(Continued)

OTHER PUBLICATIONS

Abraham, Robert T., "Cell cycle checkpoint signaling through the ATM and ATR kinases," *Genes & Dev.*, 15:2177-2196 (2001).

(Continued)

*Primary Examiner*—Taofiq Solola
*Assistant Examiner*—Robert Shiao
(74) *Attorney, Agent, or Firm*—Michael Best & Friedrich LLP

(57) ABSTRACT

The application concerns a compound of formula I:

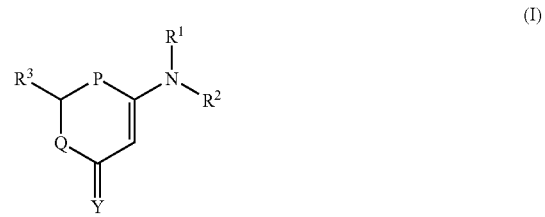

Figure 1:
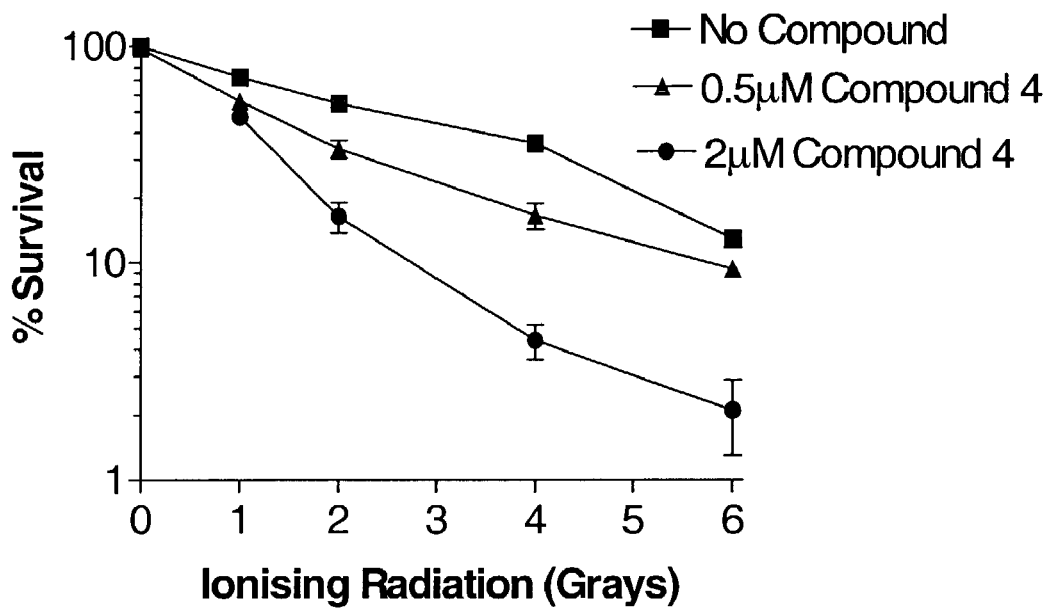

wherein one of P and Q is O, and the other of P and Q is CH, where there is a double bond between whichever of Q and P is CH and the carbon atom bearing the $R^3$ group;

Y is either O or S;

$R^1$ and $R^2$ are independently hydrogen, an optionally substituted $C_{1-7}$ alkyl group, $C_{3-20}$ heterocyclyl group, or $C_{5-20}$ aryl group, or may together form an optionally substituted heterocyclic ring having from 4 to 8 ring atoms;

$R^3$ is a phenyl or pyridyl group, attached by a first bridge group selected from —S—, —S(=O)—, —S(=O)$_2$—, —O—, —NR$^N$— and CR$^{C1}$R$^{C2}$— to an optionally substituted $C_{5-20}$ carboaryl group, the phenyl or pyridyl group and optionally substituted $C_{5-20}$ carboaryl group being optionally further linked by a second bridge group, so as to form an optionally substituted $C_{5-7}$ ring, the phenyl or pyridyl group being further optionally substituted.

9 Claims, 6 Drawing Sheets

FOREIGN PATENT DOCUMENTS

| | | |
|---|---|---|
| WO | WO 97/18323 | 5/1997 |
| WO | WO 98/55602 | 12/1998 |
| WO | WO 98/56391 | 12/1998 |
| WO | WO 99/47494 | 9/1999 |
| WO | WO 01/53266 A1 | 7/2001 |
| WO | WO 02/20500 | 3/2002 |
| WO | WO 02/20500 A2 | 3/2002 |
| WO | WO 02/056912 A2 | 7/2002 |
| WO | WO 03/024949 A1 | 3/2003 |
| WO | WO 03/034997 A2 | 5/2003 |
| WO | WO 03/035618 A2 | 5/2003 |

OTHER PUBLICATIONS

Archer, S. et al., "Ring-Hydroxylated Analogues of Lucanthone as Antitumore Agents," *J. Med Chem.*, 25, 220-227 (1982).

Banin, S., et al., "Enhanced phosphorylation of p53 by ATM in response to DNA damage," *Science*, 281:1674-1677 (1998).

Berge, Stephen M., et al., "Review article," *J. Pharm. Sci.*, 66:1, pp. 1-19 (1977).

Brown, P.O., "Integration of retroviral DNA," *Curr Top Microbiol Immunol.*, 157:19-48 (1990).

Daniel, Rene, et al., "Wortmannin potentiates integrase-mediated killing of lymphocytes and reduces the efficiency of stable transduction by retroviruses," *Mol. Cell Biol*, 21:4, 1164-1172 (2001).

Durocher, Daniel, and Jackson, Stephen P., "DNA-PK, ATM and ATR as sensors of DNA damage: variations on a theme?," *Curr Opin Cell Biol.*, 13:225-231 (2001).

Giroux, A., et al, "One pot biaryl synthesis via in situ boronate formation," *Tet. Lett.*, 38:22, 3841-3844 (1997).

Haselhorst, Dorte, et al., "Development of cell lines stably expressing human immunodeficiency virus type 1 proteins for studies in encapsidation and gene transfer," *J Gen Virol*, 79:231-237 (1998).

Herzog, Karl-Heinz et al., "Requirement for ATM in ionizing radiation-induced cell death in the developing central nervous system," *Science*, 280: 1089-1091 (1998).

Ishiyama, T. et al., "Synthesis of arylboronates via the palladium(0)-catalyzed cross-coupling reaction of tetra(alkoxo)diborons with aryl triflates," *Tett. Lett.*, 38:19, 3447-3450 (1997).

Keith, Curtis T. and Schreiber, Stuart L., "PIK-related kinases: DNA repair, recombination, and cell cycle checkpoints," *Science*, 270: 50-51 (1995).

Lavin, Martin F. and Shiloh, Yosef, "The genetic defect in ataxia-telangiectasia," *Annu. Rev. Immunol*, 15:177-202 (1997).

Metcalfe, Judith A. et al., "Accelerated telomere shortening in ataxia telangiectasia," *Nature Genetics*, 13:350-353 (1996).

Mlotkowska, B.L. et al., "Two-dimensional NMR studies of 2-substituted thioxanthene sulfoxides," *J. Heterocyclic Chem.*, 28: 731-736 (Apr.-May 1991).

Naldini, Luigi et al., "In vivo gene delivery and stable transduction of nondividing cells by a lentiviral vector," *Science*, 272: 263-267 (1996).

Sarkaria, Jann N. et al., "Inhibition of ATM and ATR kinase activities by the radiosensitizing agent, caffeine," *Cancer Res.*, 59: 4375-4382 (1999).

Savitsky, Kinneret et al., "A single ataxia telangiectasia gene with a product similar to PI-3 kinase," *Science*, 268:1749-1753 (1995).

Shiloh, Yosef, "ATM and ATR: networking cellular responses to DNA damage," *Curr. Opin. Genet. Dev.*, 11:71-77 (2001).

Toker, Alex and Cantley, Lewis C., "Signalling through the lipid producdtsd of phosphoinositide-3-OH kinase," *Nature*, 387:673-676 (1997).

Zakian, Virginia A., "ATM-related genes: What do they tell us about functions of the human gene?" *Cell*, 82:685-687 (1995).

Hickson, Ian, et al, Identification and Characterization of a Novel and Specific Inhibitor of the Ataxia-Telangiectasia Mutated Kinase ATM, Cancer Research, Dec. 15, 2004, 9152-9159, vol. 64.

Chiosis G, et al., "LY294002-geldanamycin heterodiamers as selective inhibitors of the PI3K and PI3k-related family", Bioorganic & Medicinal Chemistry Letters, vol. 11, No. 7, Apr. 9, 2001 pp. 909-913.

Hollick, J J, et al., "2,6-Disubstituted pyran-4-one and thiopyran-4-one inhibitors of DNA-dependent protein kinase" Bioorganic and Medicinal Chemistry Letters, vol. 13, No. 18, Sep. 15, 2003 pp. 3083-3086, XP002303369.

Bantick, J.R., et al., "Synthesis of 2-aminochromones," *J. Heterocyclic Chem.*, 1981, vol. 18, pp. 679-684.

Bettoni, et al., "Synthesis and absolute configuration of substituted morpholines," *Tetrahedron*, 1980, vol. 36, pp. 409-415.

Boyd, J., et al., "The chemistry of the insoluble red woods," *J. Chem. Soc.*, 1948, pp. 174-176.

Buon, C., et al., "Synthesis of 3-substituted and 2,3-disubstituted-4H-1,4-Benzoxazines," *Tetrahedron*, 2000, vol. 56, pp. 605-614.

Daniel, R., et al., "A role for DNA-PK in retroviral DNA integration," *Science*, 1999, vol. 284, pp. 644-647.

Datta, A., et al., "Reformatsky reaction on aroylketene S, N-acetals: a facile route to 4-amino-6-aryl-2H-pyran-2-ones," *Synthesis*, 1988, vol. 3, pp. 248-250.

Di Braccio, M., et al., "1,2-fused pyrimidines VII," *Eur. J. Med., Chem.*, 1995, vol. 30, No. 1, pp. 27-38.

Di Braccio, M., et al., "Pyran derivatives XIX. (Dialkylamino) substituted 1-benzopyranones and naphthopyranoes with platelet antiaggregating activity," *Farmaco*, 1995, vol. 50, No. 10, pp. 703-711.

Ermili, A., et al., "Chemical and pharmacological research on pyran derivatives," Enclosed: *Chemical Abstracts*, 1977, vol. 87, No. 15, p. 588 (XP-002218602). 117750g.

Gell, D., et al., "Mapping of protein-protein interactions within the DNA-dependent protein kinase complex," *Nucleic Acid Res.*, 1999, vol. 27, No. 17, pp. 3494-3502.

Goytisolo, et al., "The absence of DNA-dependent protein kinase catalytic subunit in mice results in anaphase bridges and in increased telomeric fusions with normal telomere length and G-strand overhang," *Mol. Cell. Biol.*, 2001, vol. 21, No. 11, pp. 3642-3651.

Hartley, K. O., et al., "DNA-dependent protein kinase catalytic subunit: a relative of phosphatidylinositol 3-kinase and the ataxia telengiectasia gene product," *Cell*, 1995, vol. 82, pp. 849-856.

Izzard, R.A., et al., "Competitive & noncompetitive inhibition of the DNA-dependent protein kinase," *Cancer Research*, 1999, vol. 59, No. 11, pp. 2581-2586.

Jackson, S. P., "DNA damage detection by DNA dependent protein kinase and related enzymes," *Cancer Surv.*, 1996, vol. 28, pp. 261-279.

Jung, J. C., et al., "Simple and cost effective synthesis of 4-hydroxycoumarin," *Synth. Commun.*, 1999, vol. 29, No. 20, pp. 3587-3595.

Knight, A.R., et al., "Isolation and characterization of 4-chloro-3,4';3',4-tercoumarin," *Can. J. Chem.*, 1968, vol. 46, pp. 2495-2499.

Kubik, et al., "Fine tuning of the cation affinity of artificial receptors based on cyclic peptides by intramolecular conformational control," *Eur. J. Org. Chem.*, 2001, pp. 311-322.

Morris, J., et al., "Synthesis and biological evaluation of antiplatelet 2-aminochromones," *J. Med. Chem.*, 1993, vol. 36, No. 14, pp. 2026-2032.

Morris, J., et al., "Synthesis of 2-amino-6-phenyl-4H-pyran-4-ones," *Synthesis*, 1994, pp. 43-46.

Morris, J., et al., "Reaction of phosgeniminium salts with enolates derived from Lewis acid complexes of 2-hydroxypropiophenones and related β-Diketones," *J. Org. Chem.*, 1996, vol. 61, No. 9, pp. 3218-3220.

Oh, C., et al., "Nucleophilic vinylic substitution of halocoumarins and halo-1,4-napthoquinones with morpholine," *J. Heterocyclic Chem.*, 1994, vol. 31, pp. 841-843.

Roma, G., et al., "Synthesis, antiplatelet activity and comparative molecular field analysis of substituted 2-amino-4H pyrido[1,2-a]pyrimidin-4-ones, their congeners and isosteric analogues," *Bioorganic & Medicinal Chemistry*, 2000, vol. 8, pp. 751-768.

Roma, G., et al., "Pyran derivatives XX. 2-aminochromone benzo-fused derivatives with antiproliferative properties," *Il Farmaco*, 1998, vol. 53, pp. 494-503.

Rosenzweig, K.E., et al., "Radiosensitization of human tumor cells by the phosphatidylinositol 3-kinase inhibitors Wortmannin and LY294002 correlates with inhibition of DNA-dependent protein kinase and prolonged G2-M delay," *Clin. Cancer Res.*, 1997, vol. 3, 1149-1156.

Schroth, W., et al., "2,4,6-Tris(dialkylamino) pyrylium salts and related systems, synthesis and reaction behavior," *Tetrahedron Letters*, 1988, vol. 29, No. 37, pp. 4695-4698.

Schroth, W. et al., "2,4,6-Tris(dialkylamino) pyrylium salts and related systems, synthesis and reaction behavior," Chemical Abstracts, 110:135031.

Skehan, P., et al., "New colorimetric cytotoxicity assay for anticancer-drug screening," *J. Natl. Cancer Inst.*, 1990, vol. 82, No. 13, pp. 1107-1112.

Smith, G. C. M., et al., "The DNA-dependent protein kinase," *Genes & Dev.*, 1999, vol. 13, pp. 916-934.

Snyder, et al., "Structure and reactions of malonyl-α-aminopyridine. I," *J. Am. Chem. Soc.*, 1952, vol. 74, pp. 4910-4916.

Ten Hoeve, et al., "Direct substitution of aromatic ethers by lithium amides. A new aromatic amination reaction," *J. Org. Chem.*, 1993, vol. 58, pp. 5101-5106.

Veuger, S.J., et al., "Radiosensitization and DNA repair inhibition by the combined use of novel inhibitors of DNA-dependent protein kinase and poly (ADP-ribose) polymerase-1," *Cancer Research*, 2003, vol. 63, pp. 6008-6015.

Vlahos, C.J., et al., "A specific inhibitor of phosphatidylinositol 3-kinase, 2-(4-morpholinyl)-8-phenyl-4H-1-benzopyran-4-one (LY294002)," *J. Biol. Chem.*, 1994, vol. 269, No. 7, pp. 5241-5248.

Wymann, M.T., et al., "Wortmannin inactivates phosphoinositide-3-kinase by covalent modification of Lys-802, a residue involved in the phosphate transfer reaction," *Mol. Cell Biol.*, 1996, vol. 16, No. 4, pp. 1722-1733.

Leahy, et al., "Identification of a highly potent and selective DNA-dependent protein kinase (DNA-PK) inhibitor (NU7441) by screening of chromenone librariest", Bioorganic & Medicinal Chemistry Letters 14 (2004) 6083-6087.

Griffin, et al., "Selective Benzopyranone and Pyrimido [2,1-a]isoquinolin-4-one Inhibitors of DNA-Dependent Protein Kinase: Synthesis, Structure—Activity Studies, and Radiosensitization of a Humn Tumor Cell Line in Vitro", J. Med. Chem., 2005, 48, 569-585.

Willmore, et al., "A novel DNA-dependent protein kinase inhibitor, NU7026, potentiates the cytotoxicity of topoisomerase II poisons used in the treatment of leukemia", Blood, Jun. 15, 2004, vol. 103, No. 12, 4659-4665.

\* cited by examiner

A

B

C

ATM INHIBITORS

This application claims the benefit of prior filed co-pending provisional patent application No. 60/360,493 filed on Feb. 28, 2002 and provisional patent application No. 60/395,884 filed on Jul. 15, 2002.

The present invention relates to compounds which act as ATM inhibitors, their use and synthesis.

Human DNA is constantly under attack from reactive oxygen intermediates principally from by-products of oxidative metabolism. Reactive oxygen species are capable of producing DNA single-strand breaks and, where two of these are generated in close proximity, DNA double strand breaks (DSBs). In addition, single- and double-strand breaks can be induced when a DNA replication fork encounters a damaged template, and are generated by exogenous agents such as ionising radiation (IR) and certain anti-cancer drugs (e.g. bleomycin, etoposide, camptothecin). DSBs also occur as intermediates in site-specific V(D)J recombination, a process that is critical for the generation of a functional vertebrate immune system. If DNA DSBs are left unrepaired or are repaired inaccurately, mutations and/or chromosomal aberrations are induced, which in turn may lead to cell death. To combat the serious threats posed by DNA DSBs, eukaryotic cells have evolved several mechanisms to mediate their repair. Critical to the process of DNA repair is the slowing down of cellular proliferation to allow time for the cell to repair the damage. A key protein in the detection of DNA DSBs and in the signalling of this information to the cell cycle machinery is the kinase ATM (ataxia telangiectasia mutated) (Durocher and Jackson (2001) DNA-PK, ATM and ATR as sensors of DNA damage: variations on a theme? *Curr Opin Cell Biol.*, 13:225–31, Abraham (2001) Cell cycle checkpoint signaling through the ATM and ATR kinases. *Genes Dev.*, 15; 2177–96).

The ATM protein is an ~350 kDa polypeptide that is a member of the phosphatidylinositol (PI) 3-kinase family of proteins by virtue of a putative kinase domain in its carboxyl-terminal region (Savitsky et al (1995) A single ataxia telangiectasia gene with a product similar to PI-3 kinase. *Science*, 268:1749–53). Classical PI 3-kinases, such as PI 3-kinase itself, are involved in signal transduction and phosphorylate inositol lipids that act as intracellular second messengers (reviewed in Toker and Cantley (1997) Signalling through the lipid products of phosphoinositide-3-OH kinase, *Nature*, 387: 673–6). However, ATM bears most sequence similarity with a subset of the PI 3-kinase family that comprises proteins which, like ATM, are involved in cell cycle control and/or in the detection and signalling of DNA damage (Keith and Schreiber (1995) PIK-related kinases: DNA repair, recombination, and cell cycle checkpoints, *Science*, 270; 50–1, Zakian (1995) ATM-related genes: what do they tell us about functions of the human gene? *Cell*, 82; 685–7). Notably there is no evidence to date that any members of this subset of the PI 3-kinase family are able to phosphorylate lipids. However, all members of this family have been shown to possess serine/threonine kinase activity. ATM phosphorylates key proteins involved in a variety of cell-cycle checkpoint signalling pathways that are initiated in response to DNA DSBs production (see below). These downstream effector proteins include p53, Chk2, NBS1/nibrin, BRCA1 and Rad 17 (Abraham, 2001)

ATM is the product of the gene mutated in ataxia-telangiectasia (A-T) (Savitsky et al (1995)). A-T is a human autosomal recessive disorder present at an incidence of around 1 in 100,000 in the population. A-T is characterised by a number of debilitating symptoms, including progressive cerebellar degeneration, occulocutaneous telangiectasia, growth retardation, immune deficiencies, cancer predisposition and certain characteristics of premature ageing (Lavin and Shiloh (1997), The genetic defect in ataxia-telangiectasia. *Annu. Rev. Immunol.*, 15:177–202; Shiloh (2001), ATM and ATR: networking cellular responses to DNA damage, *Curr. Opin. Genet. Dev.*, 11:71–7). At the cellular level, A-T is characterised by a high degree of chromosomal instability, radio-resistant DNA synthesis, and hypersensitivity to ionizing radiation (IR) and radiomimetic drugs. In addition, A-T cells are defective in the radiation induced $G_1$-S, S, and $G_2$-M cell cycle checkpoints that are thought to arrest the cell cycle in response to DNA damage in order to allow repair of the genome prior to DNA replication or mitosis (Lavin and Shiloh, 1997). This may in part reflect the fact that A-T cells exhibit deficient or severely delayed induction of p53 in response to IR. Indeed, p53-mediated downstream events are also defective in A-T cells following IR exposure. ATM therefore acts upstream of p53 in an IR-induced DNA damage signalling pathway. A-T cells have also been shown to accumulate DNA double-strand breaks (dsbs) after ionizing radiation, suggesting a defect in dsb repair.

It is clear that ATM is a key regulator of the cellular response to DNA DSBs. Therefore the inhibition of this kinase through small molecules will sensitise cells to both ionising radiation and to chemotherapeutics that induce DNA DSBs either directly or indirectly. ATM inhibitors may thus be used as adjuncts in cancer radiotherapy and chemotherapy. To date the only reported inhibitors of ATM (caffeine and wortmannin; Sarkaria, et al., (1999) Inhibition of ATM and ATR kinase activities by the radiosensitizing agent, caffeine. *Cancer Res.*, 59:4375–82; Banin, et al., (1998) Enhanced phosphorylation of p53 by ATM in response to DNA damage.

*Science*, 281:1674–1677) do cause radiosensitisation but it is unclear whether this mechanism of action is mediated through ATM inhibition as these small molecules are very non-specific in action as kinase inhibitors.

ATM function in response to ionising radiation induced DNA damage has been shown to be tissue specific. For example, while fibroblasts derived from Atm null mice are radiosensitive Atm null neurons are radioresistant through a lack of IR induced apoptosis (Herzog et al., (1998) Requirement for Atm in ionizing radiation-induced cell death in the developing central nervous system. *Science*, 280: 1089–91). Therefore, inhibitors of ATM have the potential to be radio-protective in specific cellular contexts.

ATM inhibitors may also prove useful in the treatment of retroviral mediated diseases. It has been demonstrated that ATM function is required to allow stable retroviral DNA transduction under certain conditions (Daniel et al. (2001) Wortmannin potentiates integrase-mediated killing of lymphocytes and reduces the efficiency of stable transduction by retroviruses. *Mol. Cell Biol.*, 21: 1164–72). Therefore ATM inhibitors have the potential to block retroviral DNA integration.

ATM is known to play a crucial role in controlling the length of telomeric chromosomal ends (Metcalfe et al. (1996) Accelerated telomere shortening in ataxia telangiectasia. *Nat Genet.*, 13 :350–3). Telomeric ends in most normal cell types shorten at each cell division. Cells with excessively shortened telomeres are unable to divide. Inhibitors of ATM may therefore, have utility in preventing cancer progression by limiting the growth potential of cancerous or pre-cancerous cells. Furthermore, ATM does not appear to be part of the telomerase enzyme itself (Metcalfe et al.

(1996)) Therefore it is likely that ATM inhibitors will work synergistically with anti-telomerase drugs.

Cells derived from A-T patients or from mice null for ATM grow slower in culture than genetically matched ATM positive cells. Therefore an ATM inhibitor may have growth inhibitory/anti-proliferative properties in its own right. Therefore an ATM inhibitor may be used as a cytostatic agent in the treatment of cancer.

A-T patients display immuno-deficiencies, demonstrating that ATM is required for generation of a fully functional immune system. Inhibitors of ATM may, therefore, be used in modulating the immune system.

In summary ATM inhibitors have the potential to sensitise tumour cells to ionising radiation or DNA DSB inducing chemotherapeutics, to modulate telomere length control mechanisms, to block retroviral integration, modulate the immune system and to protect certain cell types from DNA damage induced apoptosis.

The present inventors have now discovered compounds which exhibit inhibition of ATM.

Accordingly, the first aspect of the invention provides a compound of formula I:

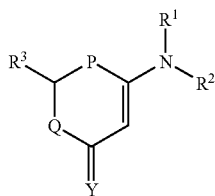

(I)

and isomers, salts, solvates, chemically protected forms, and prodrugs thereof, wherein:

one of P and Q is O, and the other of P and Q is CH, where there is a double bond between whichever of Q and P is CH and the carbon atom bearing the $R^3$ group;

Y is either O or S;

$R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms;

$R^3$ is a phenyl or pyridyl group, attached by a first bridge group selected from —S—, —S(=O)—, —S(=O)$_2$—, —O—, —NR$^N$— and CR$^{C1}$R$^{C2}$— to an optionally substituted $C_{5-20}$ carboaryl group, in which one aromatic ring atom may be replaced by a nitrogen ring atom;

the phenyl or pyridyl group and optionally substituted $C_{5-20}$ carboaryl group being optionally further linked by a second bridge group, which is bound adjacent the first bridge group on both groups so as to form an optionally substituted $C_{5-7}$ ring fused to both the phenyl or pyridyl group and the $C_{5-20}$ carboaryl group, the phenyl or pyridyl group being further optionally substituted;

wherein $R^N$ is selected from hydrogen, an ester group, an optionally substituted $C_{1-7}$ alkyl group, an optionally substituted $C_{3-20}$ heterocyclyl group and an optionally substituted $C_{5-20}$ aryl group;

and $R^{C1}$ and $R^{C2}$ are independently selected from hydrogen, an optionally substituted $C_{1-7}$ alkyl group, an optionally substituted $C_{3-20}$ heterocyclyl group and an optionally substituted $C_{5-20}$ aryl group.

Therefore, when P is O and Q is CH, the compound is of formula (Ia):

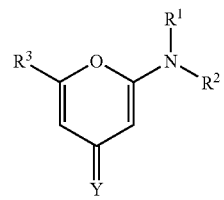

(Ia)

and when P is CH and Q is O, the compound is of formula (Ib):

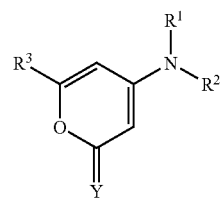

(Ib)

A second aspect of the invention provides a composition comprising a compound of the first aspect and a pharmaceutically acceptable carrier or diluent.

A third aspect of the invention provides methods of treating a condition in a patient which is known to be ameliorated by the inhibition of ATM comprising administering to said patient a therapeutically-effective amount of a compound of the first aspect.

A fourth aspect of the invention provides methods of treating cancer in a patient comprising administering to said patient a therapeutically-effective amount of a compound of the first aspect in combination with ionising radiation or a chemotherapeutic agent.

A fifth aspect of the invention provides methods of treating a retroviral mediated disease, including acquired immunodeficiency syndrome, in a patient comprising administering to said patient a therapeutically-effective amount of a compound of the first aspect.

Another aspect of the invention provides a method of inhibiting ATM in vitro or in vivo, comprising contacting a cell with an effective amount of a compound of the first aspect.

Definitions $C_{1-7}$ alkyl: The term "$C_{1-7}$ alkyl", as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl", as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran ($C_6$), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulphur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulphur ring atom include, but are not limited to, those derived from oxathiolane and oxathiane (thioxane).

Examples of $C_{3-20}$ heterocyclyl groups having one nitrogen ring atom and one sulphur ring atom include, but are not limited to, those derived from thiazoline, thiazolidine, and thiomorpholine.

Other examples of $C_{3-20}$heterocyclyl groups include, but are not limited to, oxadiazine and oxathiazine.

Examples of heterocyclyl groups which additionally bear one or more oxo (=O) groups, include, but are not limited to, those derived from:

$C_5$ heterocyclics, such as furanone, pyrone, pyrrolidone (pyrrolidinone), pyrazolone (pyrazolinone), imidazolidone, thiazolone, and isothiazolone;

$C_6$heterocyclics, such as piperidinone (piperidone), piperidinedione, piperazinone, piperazinedione, pyridazinone, and pyrimidinone (e.g., cytosine, thymine, uracil), and barbituric acid;

fused heterocyclics, such as oxindole, purinone (e.g., guanine), benzoxazolinone, benzopyrone (e.g., coumarin);

cyclic anhydrides (—C(=O)—O—C(=O)— in a ring), including but not limited to maleic anhydride, succinic anhydride, and glutaric anhydride;

cyclic carbonates (—O—C(=O)—O— in a ring), such as ethylene carbonate and 1,2-propylene carbonate;

imides (—C(=O)—NR—C(=O)— in a ring), including but not limited to, succinimide, maleimide, phthalimide, and glutarimide;

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam, γ-butyrolactam (2-pyrrolidone), δ-valerolactam, and ε-caprolactam;

cyclic carbamates (—O—C(=O)—NR— in a ring), such as 2-oxazolidone;

cyclic ureas (—NR—C(=O)—NR— in a ring), such as 2-imidazolidone and pyrimidine-2,4-dione (e.g., thymine, uracil).

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g. fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$), and pyrene ($C_{16}$).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heteroaryl groups which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

The above $C_{1-7}$ alkyl, $C_{3-20}$ heterocyclyl, and $C_{5-20}$ aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

$C_{1-2}$ alkdioxylene: The term "$C_{1-2}$ alkdioxylene," as used herein, pertains to a bidentate moiety obtained by removing two hydrogen atoms from each of two different alcohol groups of a $C_{1-2}$ hydrocarbon diol compound having from 1 or 2 carbon atoms, i.e. CH$_2$(OH)$_2$ and HO—CH$_2$—CH$_2$—OH, to form —O—CH$_2$—O— and —O—CH$_2$—CH$_2$—O—. This bidentate moiety may be the substituent group of a single atom or of two adjacent atoms.

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$alkyl-group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl and phthalimidyl:

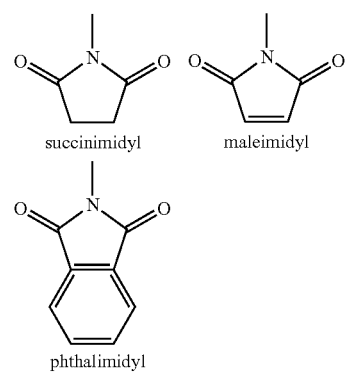

succinimidyl    maleimidyl phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Tetrazolyl: a five membered aromatic ring having four nitrogen atoms and one carbon atom,

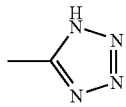

Amino: —NR¹R², wherein R¹ and R² are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$alkyl group, or, in the case of a "cyclic" amino group, R¹ and R², taken together with the nitrogen atom to which they are attached, form a heterocyclic ring having from 4 to 8 ring atoms. Examples of amino groups include, but are not limited to, —NH₂, —NHCH₃, —NHC(CH₃)₂, —N(CH₃)₂, —N(CH₂CH₃)₂, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, hydrogen, a $C_{1-7}$ alkyl group, a $C_{3-20}$ heterocyclyl group, or a $C_{5-20}$ aryl group, preferably H or a $C_{1-7}$ alkyl group.

Amidine: —C(=NR)NR₂, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is —C(=NH)NH₂.

Nitro: —NO₂.

Nitroso: —NO.

Azido: —N₃.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH₃ and —SCH₂CH₃.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH₃ and —SSCH₂CH₃.

Sulfone (sulfonyl): —S(=O)₂R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)₂CH₃ (methanesulfonyl, mesyl), —S(=O)₂CF₃ (triflyl), —S(=O)₂CH₂CH₃, —S(=O)₂C₄F₉ (nonaflyl), —S(=O)₂CH₂CF₃ (tresyl), —S(=O)₂Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH₃ and —S(=O)CH₂CH₃.

Sulfonyloxy: —OS(=O)₂R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)₂CH₃ and —OS(=O)₂CH₂CH₃.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH₃ and —OS(=O)CH₂CH₃.

Sulfamino: —NR¹S(=O)₂OH, wherein R¹ is an amino substituent, as defined for amino groups. Examples of sulfamino groups include, but are not limited to, —NHS(=O)₂OH and —N(CH₃)S(=O)₂OH.

Sulfonamino: —NR¹S(=O)₂R, wherein R¹ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)₂CH₃ and —N(CH₃)S(=O)₂C₆H₅.

Sulfinamino: —NR¹S(=O)R, wherein R¹ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH₃ and —N(CH₃)S(=O)C₆H₅.

Sulfamyl: —S(=O)NR¹R², wherein R¹ and R² are independently amino substituents, as defined for amino groups. Examples of sulfamyl groups include, but are not limited to, —S(=O)NH₂, —S(=O)NH(CH₃), —S(=O)N(CH₃)₂, —S(=O)NH(CH₂CH₃), —S(=O)N(CH₂CH₃)₂, and —S(=O)NHPh.

Sulfonamino: —NR¹S(=O)₂R, wherein R¹ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)₂CH₃ and —N(CH₃)S(=O)₂C₆H₅. A special class of sulfonamino groups are those derived from sultams—in these groups one of R¹ and R is a $C_{5-20}$ aryl group, preferably phenyl, whilst the other of R¹ and R is a bidentate group which links to the $C_{5-20}$ aryl group, such as a bidentate group derived from a $C_{1-7}$ alkyl group. Examples of such groups include, but are not limited to:

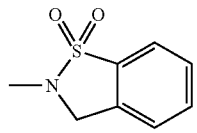

2,3-dihydro-tenzo[d]isothiazole-1,1-dioxide-2-yl

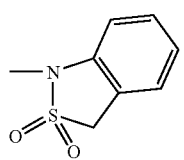

1,3-dihydro-benzo[c]isothiazole-2,2-dioxide-1-yl

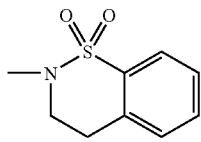

3,4-dihydro-2H-benzo[e][1,2]thiazine-1,1-dioxide-2-yl

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O) (OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O) (OCH$_2$CH$_3$)—N(CH$_3$)$_2$, —OP(=O) (OCH$_2$CH$_3$)—N(i-Pr)$_2$, and —OP(=O) (OCH$_2$CH$_2$CN)—N(i-Pr)$_2$.

In many cases, substituents may themselves be substituted. For example, a C$_{1-7}$ alkoxy group may be substituted with, for example, a C$_{1-7}$ alkyl (also referred to as a C$_{1-7}$ alkyl—C$_{1-7}$alkoxy group), for example, cyclohexylmethoxy, a C$_{3-20}$ heterocyclyl group (also referred to as a C$_{5-20}$ aryl—C$_{1-7}$ alkoxy group), for example phthalimidoethoxy, or a C$_{5-20}$ aryl group (also referred to as a C$_{5-20}$aryl-C$_{1-7}$alkoxy group), for example, benzyloxy.

C$_{5-7}$ Ring

The C$_{5-7}$ ring in R$^3$ has at least two carbon-carbon double bond, by virtue of its fusion to a benzene or pyridine ring and a C$_{5-20}$ carboaryl group. If the C$_{5-20}$ carboaryl group contains a nitrogen ring atom, this does not form part of the C$_{5-7}$ ring. The same applies to the nitrogen ring atom of the pyridyl group.

Thus, the C$_{5-7}$ ring may be a C$_{5-7}$ sulphur containing heterocycle, a C$_{5-7}$ oxygen heterocycle, a C$_{5-7}$ nitrogen containing heterocycle or a C$_{5-7}$ cyclic group containing at least 5 carbon ring atoms.

The second bridge group may typically be a single bond (resulting in a C$_5$ ring), or have 1 or 2 atoms in a chain (resulting in C$_6$ and C$_7$ rings respectively), which atoms are usually selected from C, S, O and N, with substitution as appropriate.

C$_{5-7}$ Sulphur Containing Heterocycle

The C$_{5-7}$ sulphur containing heterocycle in R$^3$ will have at least two carbon-carbon double bonds, by virtue of its fusion to a benzene or pyridine ring and a C$_{5-20}$ carboaryl group. Examples of relevant C$_{5-7}$ sulphur containing heterocycles include, but are not limited to:

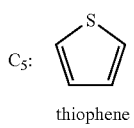

thiophene

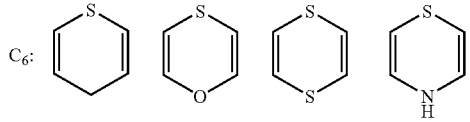

thiaine 4-thiaoxaine 1,4-dithiaine 4H-4-azathiaine

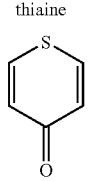

4-oxothiaine

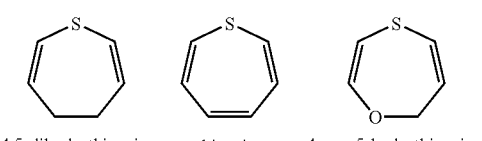

4,5-dihydrothiaepine thiaepine 4-oxa-5-hydrothiaepine

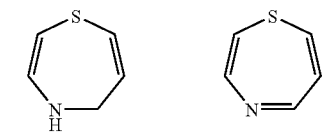

4H-4-aza-5-hydrothiaepine 4-azathiaepine

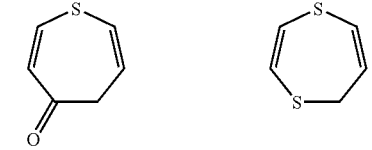

4-oxo-5-hydrothiaepine 5-hydro-1,4-dithiaepine

The C$_{5-7}$ sulphur containing heterocycle may be substituted (when possible) by the substituent group listed above.

The groups shown above may in particular be substituted on the sulphur atom in the first bridge group by one or two oxo (=O) groups.

C$_{5-7}$ Oxygen Containing Heterocycle

The C$_{5-7}$ oxygen containing heterocycle in R$^3$ will have at least two carbon-carbon double bonds, by virtue of its fusion to a benzene or pyridine ring and a C$_{5-20}$ carboaryl group. Examples of relevant C$_{5-7}$ oxygen containing heterocycles include, but are not limited to:

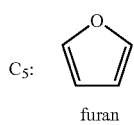

furan

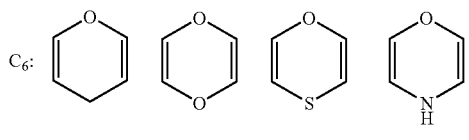

4H-pyran 1,4-dioxin 4-thiaoxaine 4H-1,4-Oxazine (p-Isoxazine)

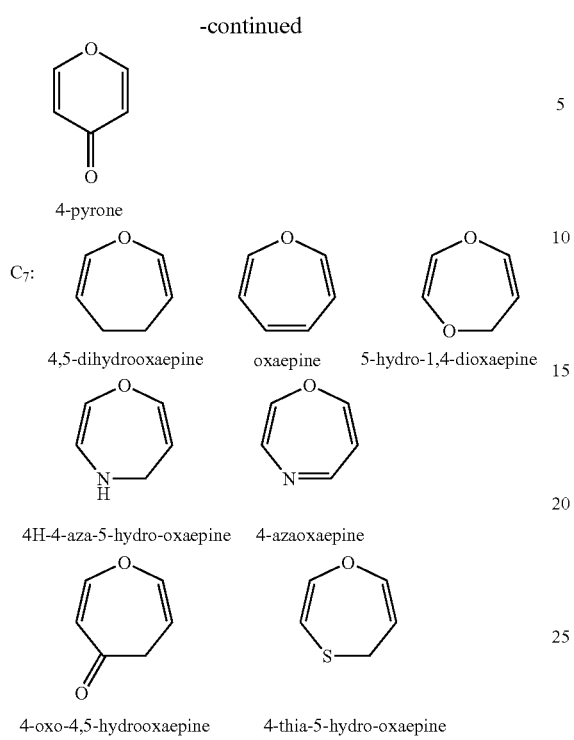

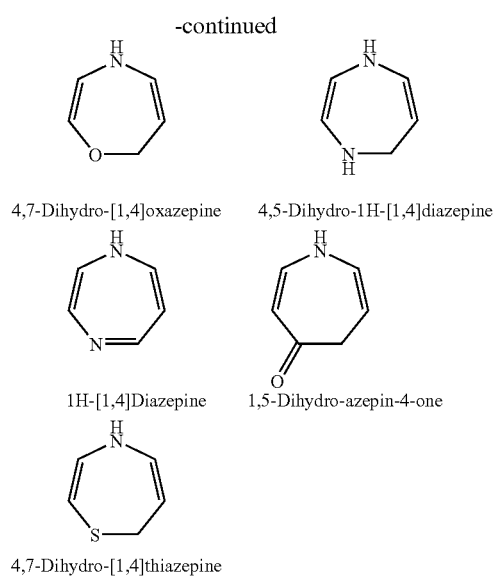

The C$_{5-7}$ oxygen containing heterocycle may be substituted (when possible) by the substituent groups listed above.

C$_{5-7}$ Nitrogen Containing Heterocycle

The C$_{5-7}$ nitrogen containing heterocycle in R$^3$ will have at least two carbon-carbon double bonds, by virtue of its fusion to a benzene or pyridine ring and a C$_{5-20}$ carboaryl group. Examples of relevant C$_{5-7}$ nitrogen containing heterocycles include, but are not limited to (illustrated with R$^N$=H):

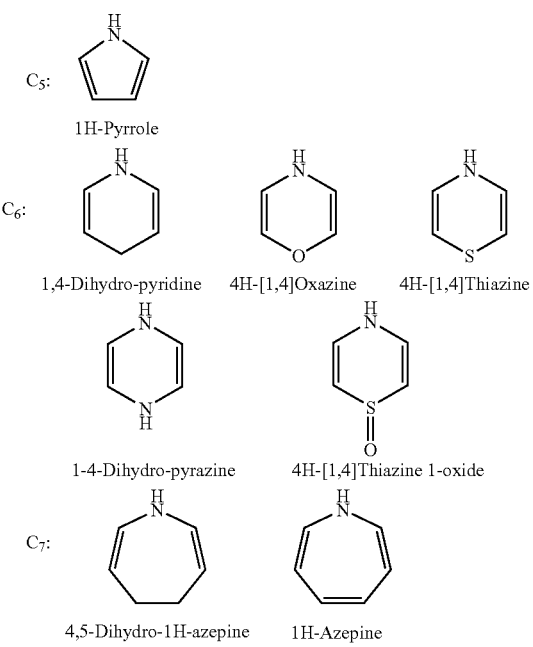

The C$_{5-7}$ nitrogen containing heterocycle may be substituted (when possible) by the substituent group listed above. In particular, the nitrogen atom in the first bridge group may be substituted by R$^N$.

C$_{5-7}$ Cyclic Group Containing at Least 5 Carbon Ring Atoms

The C$_{5-7}$ cyclic group containing at least 5 carbon ring atoms in R$^3$ will have at least two carbon-carbon double bonds, by virtue of being fused to a benzene or pyridine ring and a C$_{5-20}$ carboaryl group. Examples of relevant C$_{5-7}$ cyclic group containing at least 5 carbon ring atoms include, but are not limited to:

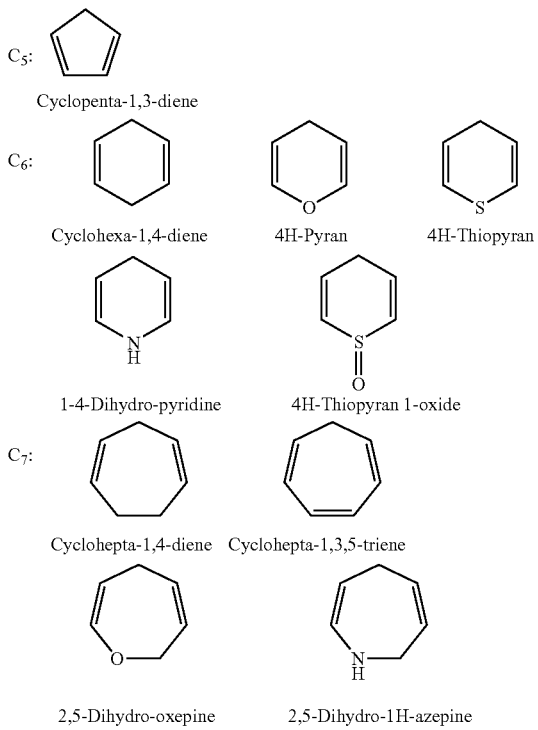

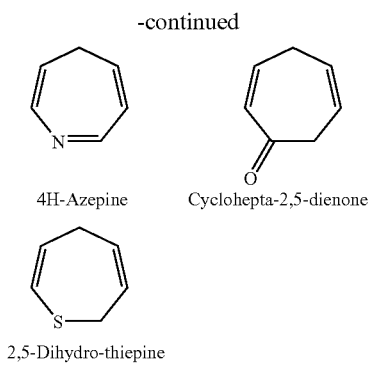

4H-Azepine    Cyclohepta-2,5-dienone 2,5-Dihydro-thiepine

The $C_{5-7}$ cyclic group containing at least 5 carbon ring atoms may be substituted (when possible) by the substituent group listed above.

Possible $R^3$ Structures

Accordingly, when the phenyl or pyridyl group is linked to a $C_{5-20}$ carboaryl group, $R^3$ can be of the following structure, wherein the phenyl or pyridyl group and the $C_{5-20}$ carboaryl group are illustrated as benzene rings, without being limited thereto, and where X may be O, S, S(=O), S(=O)$_2$, NR$^N$ and CR$^{C1}$R$^{C2}$:

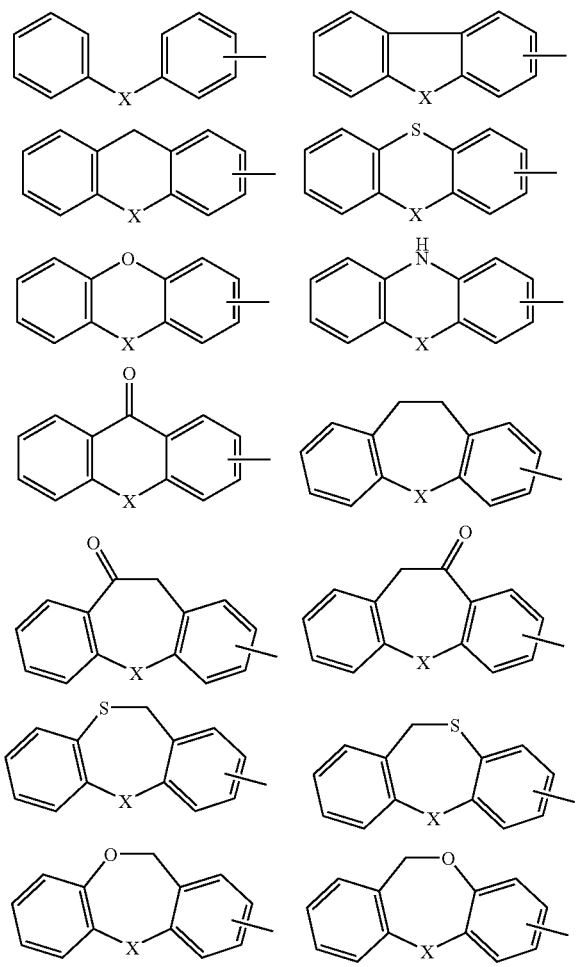

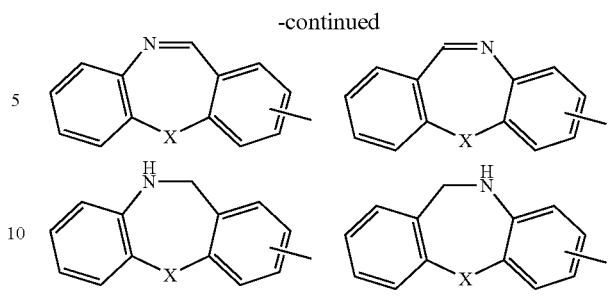

with substitution as appropriate on the above core structures

When the phenyl or pyridyl group is linked to a $C_{5-20}$ carboaryl group in which one aromatic carbon ring atom has been replaced by an aromatic nitrogen ring atom, then $R^3$ can be any of the structures shown above, where the benzene ring represents a $C_{5-20}$ carboaryl group containing a nitrogen ring atom, for example:

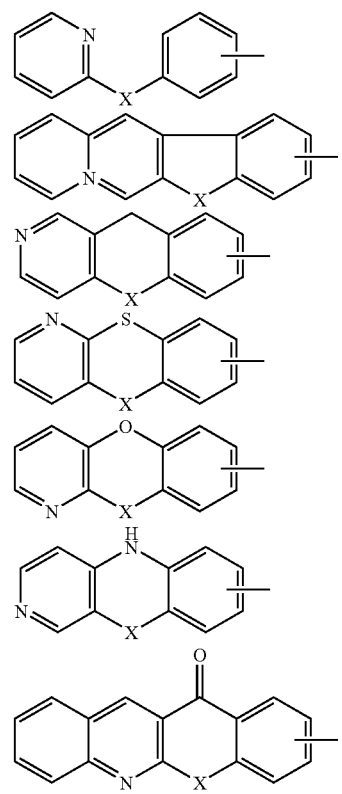

where X is as defined above.

If the first group in $R^3$ is a pyridyl group, rather than the phenyl group as illustrated above, the nitrogen ring atom may be at any available position of the ring.

The first bridge may be situated at any possible position of the phenyl group in $R^3$ and the optional second bridge group may be situated on either adjacent atom of the phenyl group (if possible). Therefore, the resulting $R^3$ group (as a whole) may be a radical at a number of possible positions on the benzene ring bound to the central moiety, for example the following possible $R^3$ group (unsubstituted xanthenyl):

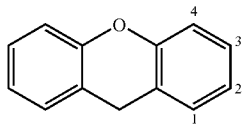

may be a radical at the 1, 2, 3 or 4 positions.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

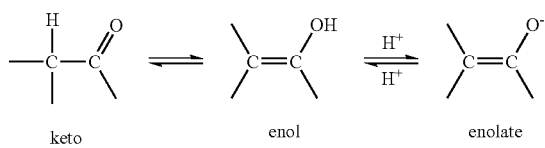

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts", J. Pharm. Sci., Vol. 66, pp. 1–19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, paimitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$ aminoalkyl (e.g. aminoethyl; 2-(N,N-diethylamino)ethyl; 2-(4-morpholino) ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Further Preferences

The following preferences may be different for different aspects of the present invention, and may be combined together.

In compounds of formula I, it is preferred that P is O and Q is CH, i.e. that the compound is of formula Ia.

Y is preferably O.

In formula I, when $R^1$ and $R^2$ form, along with the nitrogen atom to which they are attached, a heterocyclic ring having from 4 to 8 atoms, this may form part of a $C_{4-20}$ heterocyclyl group defined above (except with a minimum of 4 ring atoms), which must contain at least one nitrogen ring atom. It is preferred that $R^1$ and $R^2$ form, along with the nitrogen atom to which they are attached, a heterocyclic ring having 5, 6 or 7 atoms, more preferably 6 ring atoms.

Single rings having one nitrogen atom include azetidine, azetidine, pyrrolidine (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine; two nitrogen atoms include imidazolidine, pyrazolidine (diazolidine), imidazoline, pyrazoline (dihydropyrazole), and piperazine; one nitrogen and one oxygen include tetrahydrooxazole, dihydrooxazole, tetrahydroisoxazole, dihydroisoxazole, morpholine, tetrahydrooxazine, dihydrooxazine, and oxazine; one nitrogen and one sulphur include thiazoline, thiazolidine, and thiomorpholine.

Preferred rings are those containing one heteroatom in addition to the nitrogen, and in particular, the preferred heteroatoms are oxygen and sulphur. Thus preferred groups include morpholino, thiomorpholino, thiazolinyl. Preferred groups without a further heteroatom include pyrrolidino.

The most preferred groups are morpholino and thiomorpholino.

As mentioned above, these heterocyclic groups may themselves be substituted; a preferred class of substituent is a $C_{1-7}$ alkyl group. When the heterocyclic group is morpholino, the substituent group or groups are preferably methyl or ethyl, and more preferably methyl. A sole methyl substituent is most preferably in the 2 position.

As well as the single ring groups listed above, rings with bridges or cross-links are also envisaged. Examples of these types of ring where the group contains a nitrogen and an oxygen atom are:

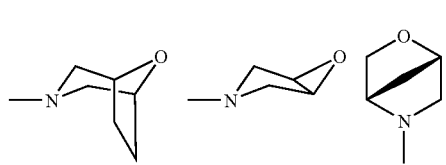

-continued

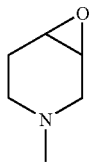

These are named 8-oxa-3-aza-bicyclo[3.2.1]oct-3-yl, 6-oxa-3-aza-bicyclo[3.1.0]hex-3-yl, 2-oxa-5-aza-bicyclo[2.2.1]hept-5-yl, and 7-oxa-3-aza-bicyclo[4.1.0]hept-3-yl, respectively.

In $R^3$, the phenyl or pyridyl group is preferably a phenyl group.

$R^{C1}$ and $R^{C2}$ are preferably H.

$R^N$ is preferably H, or an ester.

Preferred substituents of the phenyl or pyridyl ring in $R^3$ include, but are not limited to, halo, hydroxy, $C_{1-7}$ alkyl, $C_{1-7}$ alkoxy, acyl, acyloxy, amino, nitro, cyano, thiol and $C_{1-7}$ alkylthio, with halo and hydroxy being most preferred.

Preferred substituents of the phenyl or pyridyl ring or the $C_{5-20}$ carboaryl group in $R^3$ also include, but are not limited to, acylamido, sulfonamino, ether, ester, amido, amino and acyl.

In the acylamido group, the amide substituent is preferably hydrogen, and the acyl substituent is preferably selected from ester (where the ester substituent is alkyl or aryl), $C_{1-7}$ alkyl (optionally substituted by ether, ester, $C_{5-20}$ aryl, acyloxy, amino and heterocyclyl), $C_{5-20}$ aryl (optionally substituted by alkoxy, alkyl, alkoxy, ester and $C_{5-20}$ aryl) and $C_{3-20}$ heterocylyl (optionally substitued by acyl)

A particularly preferred acyl susbtituent on the acylamido group is of formula III:

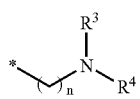

(III)

wherein n is 1 to 4, preferably 1 or 2, and $R^3$ and $R^4$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms.

In the sulfonamino group, the amino substituent is preferably hydrogen and the sulfonamino substituent selected from $C_{1-7}$ alkyl and $C_{5-20}$ aryl.

In the ether group, the ether substituent is preferably $C_{1-7}$ alkyl (optionally substituted by amino, $C_{3-20}$ heterocyclyl, thioether and $C_{5-20}$ aryl). A particularly preferred ether substituent is of formula III (defined above).

In the amido group, the amido substituents are preferably independently selected from hydrogen and $C_{1-7}$ alkyl (optionally substituted by $C_{3-20}$ heterocyclyl, $C_{5-20}$ aryl and amino). A particularly preferred amido substituent is of formula III (defined above).

In the acyl group, the acyl substituent is preferably $C_{3-20}$ heterocylyl.

These substituents are preferably either para to the radical position in the phenyl or pyridyl group, and when the first bridge group is ortho the radical position in the phenyl or pyridyl group, para to the first bridge group in the $C_{5-20}$ aryl group (especially when that group is phenyl).

Preferred structures for $R^3$ include, but are not limited to the following 'core' groups, which may bear substitution at appropriate positions, where * indicates the preferred radical position (which is typically adjacent the first bridge group on the phenyl group):

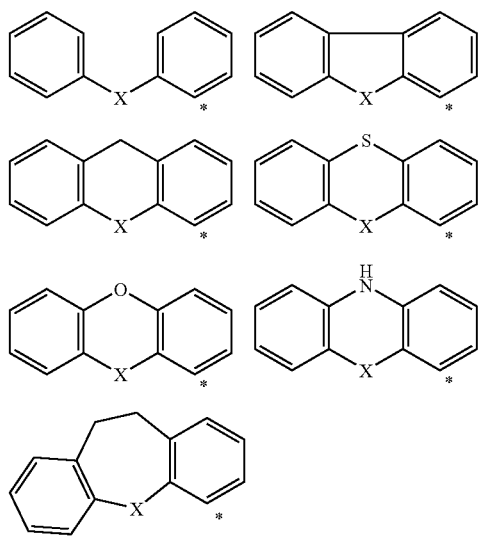

with the most preferred core structures being:

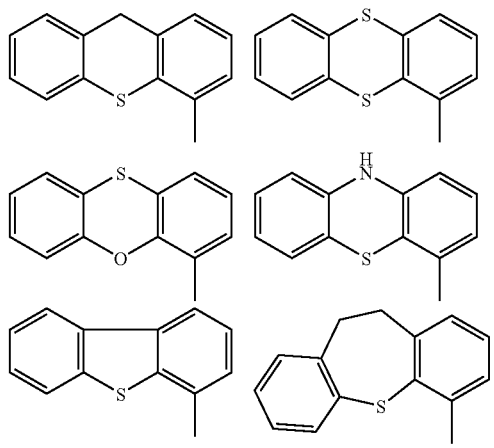

Particularly preferred $R^3$ groups include:

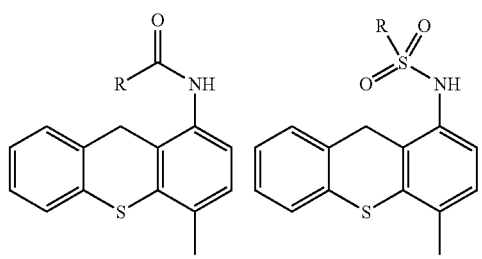

-continued

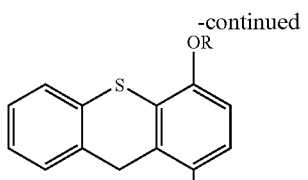

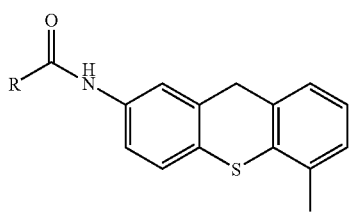

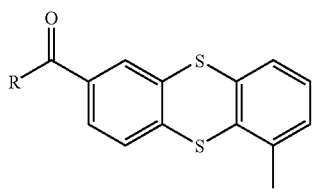

wherein R stands for the appropriate substituent group, as defined above.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), acetyl (Ac), 1,3-bis(diphenylphosphino)propane (dppf).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et₂O), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis Routes

Compounds according to the first aspect of the invention, of formula Ia, where Y=O, may be synthesised by the coupling of a 2-chloro-6-amino-pyran-4-one to an appropriate arylboronic acid or arylboronate ester using a palladium catalysed coupling reaction, e.g. Suzuki coupling. Compounds where Y=S can be derived from the corresponding compound where Y=O.

Synthesis of 2-chloro-6-amino-pyran-4-ones

These may be synthesised by the following route:

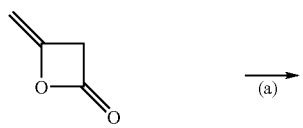

-continued

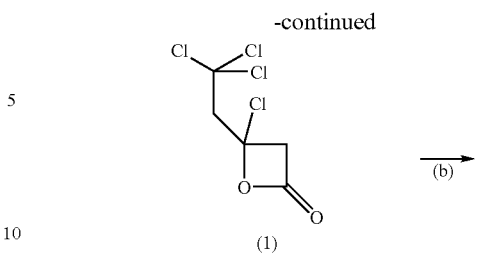

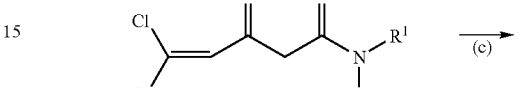

In step (a) CCl₄ is added across the carbon-carbon double bond of diketene by free-radical addition to yield 4-chloro-4(2,2,2,-trichloro-ethyl)-oxetan-2-one (1). Suitable initiators include peroxide, such as BCHPO ((bis-4-t-butylcyclohexyl)peroxydicarbonate).

In step (b), the amine R¹R²NH opens the lactone ring by nucleophilic attack at the carbonyl centre. The oxy anion generated then displaces the chlorine atom on the α-carbon to give rise to a β-keto-amide intermediate. Further elimination of HCl finally give the 5,5-dichloro-1-amino-pent-4-ene-1,3-dione. Suitable conditions for this step include inorganic base such as sodium hydrogen carbonate and solvent such as dry dichloromethane.

In step (c), ring closure takes place by displacement of one of the 5-chloro groups by the oxygen of the amide moiety to form the pyran-4-one ring, which reaction is catalysed by a Lewis acid, such as perchloric acid.

Arylboronic Acids and Arylboronate Esters

Some appropriate arylboronic acids and arylboronate esters are commercially available. Other appropriate arylboronic acids and arylboronate esters may be synthesised by using one of the following routes, in which the starting materials are commercially available or readily synthesised. For example, a synthesis route to thioxanthenone is described in Archer, S., et al., *J. Med. Chem.*, 25, 220–227, 1982, and the conversion of thioxanthenone to thiothanxene is described in Mlotkowska, B. L., et al., *J. Heterocyclic Chem.*, 28, 731–736, 1991. Other routes are shown in the examples, and include routes where the central $C_{5-7}$ ring is synthesised by ring closure from an appropriate carboxylic acid, optionally followed by reduction of the remaining keto group.

Synthesis of Aryl Boronate Esters

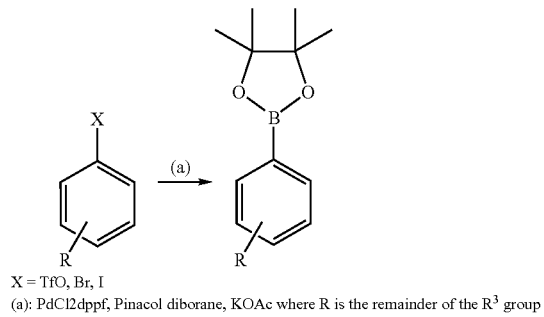

X = TfO, Br, I
(a): PdCl2dppf, Pinacol diborane, KOAc where R is the remainder of the $R^3$ group (a): PdCl2dppf, dppf, Pinacol diborane, KOAc
where R is the remainder of the $R^3$ group Aryl boronate esters may be formed by Pd(0)-catalysed cross coupling reaction of the appropriate aryl triflate or aryl halide with tetra(alkoxy)diboron, e.g. pinacol diboron. Suitable conditions include the use of a catalyst, such as $PdCl_2dppf$, extra ligands, such as dppf, potassium acetate as a base, in a solvent such as dioxane, DMF or DMSO.

Examples of this method are to be found in T Ishiyama, et al., *Tet. Lett.*, vol. 38, no. 19, 3447–3450, 1997 and A Giroux, et al., *Tet. Lett.*, vol. 38, no. 22, 3841–3844, 1997.

Synthesis of Aryl Boronic Acids

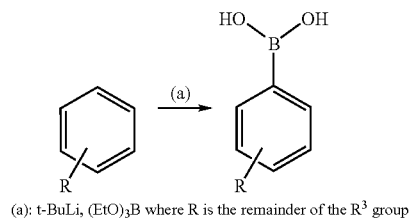

(a): t-BuLi, $(EtO)_3B$ where R is the remainder of the $R^3$ group (a):t-BuLi, $(EtO)_3B$
where R is the remainder of the $R^3$ group Boronic acids may be generated via lithiation of the aromatic ring by tert-butyl lithium followed by the reaction of the anion formed with alkyl borate such as triethyl borate to give the desired aryl boronic acid.

Palladium Catalysed Coupling

The coupling of the arylboronic acid or arylboronate ester to the 2-chloro-6-amino-pyran-4-one can be carried out using the normal conditions, e.g. a palladium catalyst (Pd($PPh_3)_4$, Pd(dppf)$Cl_2$) and base ($Na_2CO_3$, $NaOCH_2CH_3$, TlOH, $N(CH_2CH_3)_3$, $K_3PO_4$).

Compounds according to the first aspect of the invention, of formula Ib, where Y=O may be synthesised according to the following method, wherein R represents the rest of $R^3$:

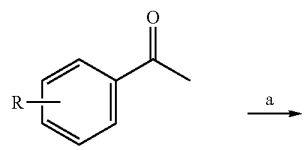

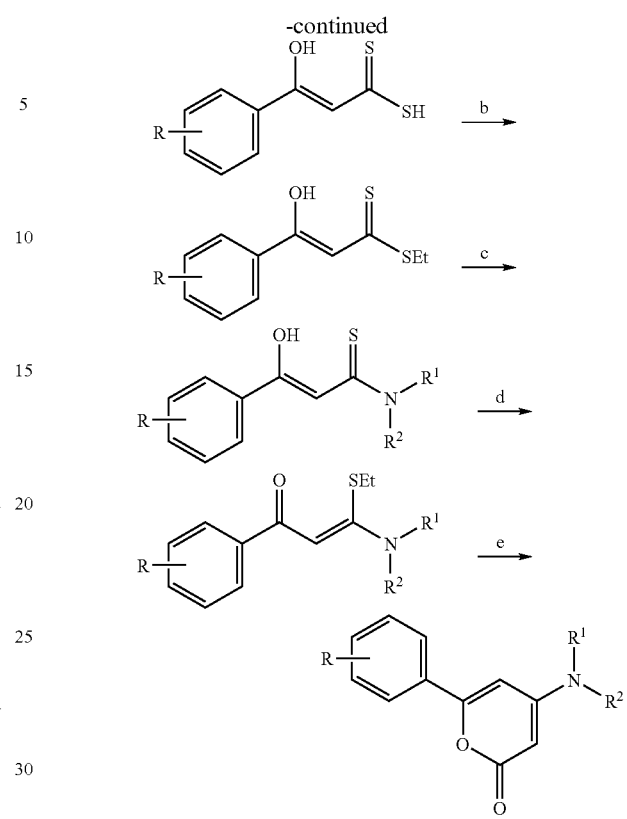

In step (a), $CS_2$ is added to the acetophenone derivative, in the presence of a base, such as potassium tert-butoxide, to yield a 3-aryl-3-hydroxy-dithioacrylic acid.

In step (b), iodoethane undergoes nucleophilic attack by the activated thioacid, to yield the ethyl ester. Activation of the thioacid can be achieved by the use of base, for example, a mixture of tetrabutylammonium hydrogen sulphate and sodium hydroxide.

In step (c), an amine displaces the ethyl group, which is followed in step (d) by reaction of the remaining thio group with iodoethane (via the tautomeric compound).

The final step (e) is a condensation with ethyl bromoacetate to yield the ring-closed 4-amino-6-aryl-pyran-2-one.

Conversion of Y from O to S

This conversion may be achieved using Lawesson's reagent in an organic solvent, such as toluene, followed by the appropriate purification steps. Protection of groups sensitive to Lawesson's reagent can be carried out before it is used, followed by deprotection once the pyranthione has been synthesised.

Use of Compounds of the Invention

The present invention provides active compounds, specifically, active 2-aryl-6-amino-pyran-4-ones, 2-aryl-6-amino-pyran-4-thiones, 4-amino-6-aryl-pyran-2-ones and 4-amino-6-aryl-pyran-2-thiones.

The term "active", as used herein, pertains to compounds which are capable of inhibiting ATM activity, and specifically includes both compounds with intrinsic activity (drugs) as well as prodrugs of such compounds, which prodrugs may themselves exhibit little or no intrinsic activity.

One assay which may be used in order to assess the ATM inhibition offered by a particular compound is described in the examples below.

The present invention further provides a method of inhibiting ATM in a cell, comprising contacting said cell with an effective amount of an active compound, preferably in the form of a pharmaceutically acceptable composition. Such a method may be practised in vitro or in vivo.

For example, a sample of cells (e.g. from a tumour) may be grown in vitro and an active compound brought into contact with said cells in conjunction with agents that have a known curative effect, and the enhancement of the curative effect of the compound on those cells observed.

The present invention further provides active compounds which inhibit ATM activity as well as methods of inhibiting ATM activity comprising contacting a cell with an effective amount of an active compound, whether in vitro or in vivo.

The invention further provides active compounds for use in a method of treatment of the human or animal body. Such a method may comprise administering to such a subject a therapeutically-effective amount of an active compound, preferably in the form of a pharmaceutical composition.

The term "treatment" as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage form comprising an active compound, which is effective for producing some desired therapeutic effect, commensurate with a reasonable benefit/risk ratio.

The present inventors have found that compounds of the present invention can efficiently repress retroviral vector transduction in one-step, cell based integration assays (termed LUCIA) and inhibit HIV-1 infection in 4-day replication assays at sub-micromolar concentrations. Further, in contrast to the observations of Daniel et al., where it was concluded that the effect of ATM on retroviral integration would only be seen in a DNA-PK-deficient background, this effect works in the presence of functional DNA-PK activity.

Initial linkage of linear retroviral DNA with host cell chromosomal DNA is catalysed by viral integrase (IN) and results in short staggered DNA strand breaks in the host cell DNA at the site of attachment (Brown, P. O. (1990) Integration of retroviral DNA. *Curr Top Microbiol Immunol*, 157, 19–48). These gapped DNA intermediates are shown to be sensed as sites of DNA damage by the host cell and repaired by the ATM pathway to complete the process of integration and allow productive infection to occur. Compounds of the invention prevent the repair of gapped DNA intermediates by the ATM pathway and thus prevent complete integration of retroviral DNA into the host genome.

As described above, the invention provides a compound as defined in the first aspect of the invention for use in the treatment of retroviral infection and the use of such a compound in the manufacture of a medicament for use in the treatment of retroviral infection.

Also provided by the invention is a method of treatment of a retroviral infection comprising administering a compound as defined in the first aspect of the invention to an individual in need thereof.

An exemplary compound of the invention which is shown to be useful in the treatment of retroviral infection is 2-Thianthren-1-yl-6-morpholin-4-yl-pyran-4-one (4).

Retroviral mediated diseases which may be treated as described above include HIV infection and acquired immunodeficiency syndrome (AIDS) and Human T-cell Leukaemia virus (HTLV) infection and its associated diseases adult T-cell leukaemia/lymphoma (ATLL) and tropical spastic paraparesis/HTLV-1 associated myelopathy (TSP/HAM).

Compounds of the invention may be used in combination with other retroviral therapies to suppress virus replication, for example in a 'highly active anti-retroviral therapy' or HAART treatment.

The invention provides a pharmaceutical composition comprising a compound as described herein and one or more other anti-retroviral agents.

The invention also provides a composition comprising a compound as defined in the first aspect of the invention and one or more other anti-retroviral agents for treatment of a retroviral infection and the use of such a composition in the manufacture of a medicament for use in the treatment of a retroviral infection.

Suitable anti-retroviral agents which inhibit retroviral replication, for example retroviral protease inhibitors (PI) such as Sequinavir, Indinavir, Ritonavir and Nelfinavir, nucleoside retroviral reverse transcriptase inhibitors such as 3'-azido-3'deoxythymidine (AZT; Zidovudine), 2',3'-Dideoxycytosine (ddC; Zalcitabine), 2',3'-Dideoxyinosine (ddI; Didanosine)and 3TC; (Lamivudine), and non-nucleoside retroviral reverse transcriptase inhibitors such as Nevirapine, Delavirdine and Efavirenz.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

In these examples, reference is made to the following figures.

FIG. 1 shows that compound 4 can sensitise cells to ionising radiation. The % survival of HeLa cells was measured with increasing ionising radiation, in the absence of compound 4 (■), and at two different concentrations of compound 4, 0.5 µM (▲) and 2 µM (●).

Figure 2:
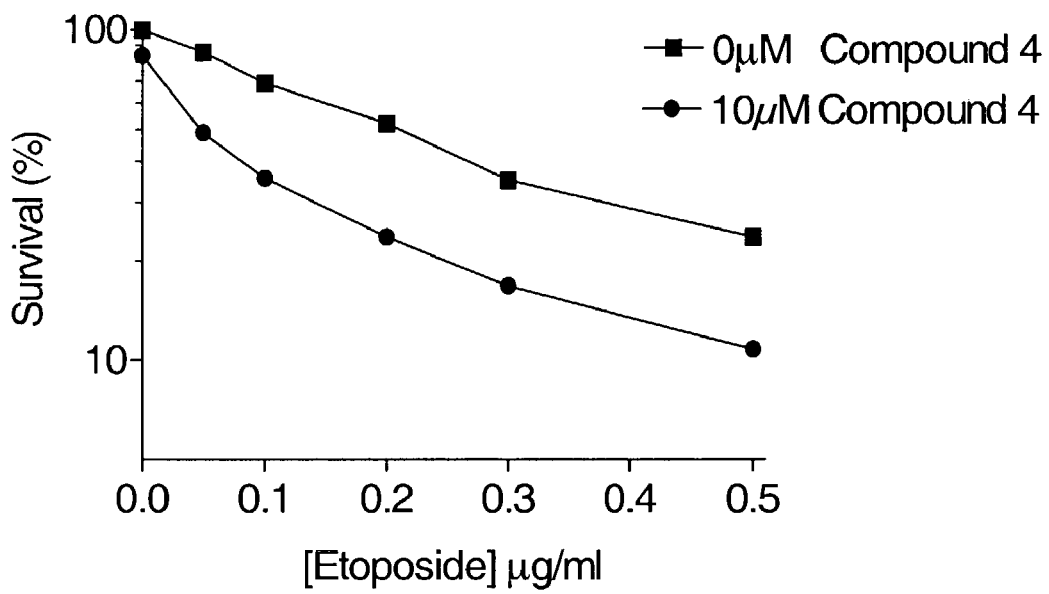

FIG. 2 shows that compound 4 can sensitise cells to etopside. The % survival of LoVo cells was measured with increasing concentrations of etopside, in the absence of compound 4 (■), and in the presence of 10 µM of compound 4 (●)

Figure 3:
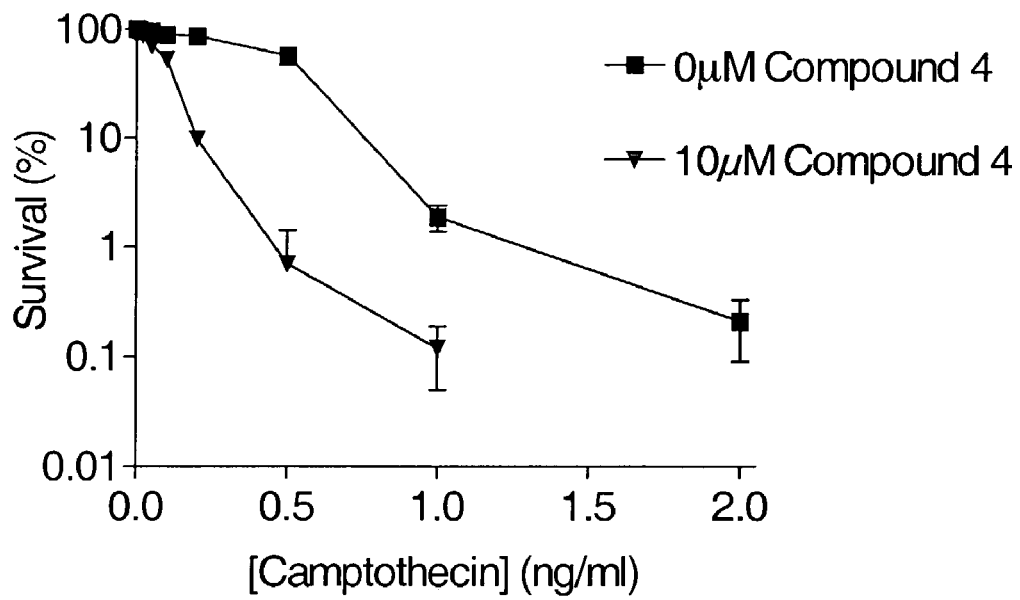

FIG. 3 shows that compound 4 can sensitise cells to camptothecin. The % survival of LoVo cells was measured with increasing concentrations of camptothecin, in the absence of compound 4 (■), and in the presence of 10 µM of compound 4 (●).

Figure 4:
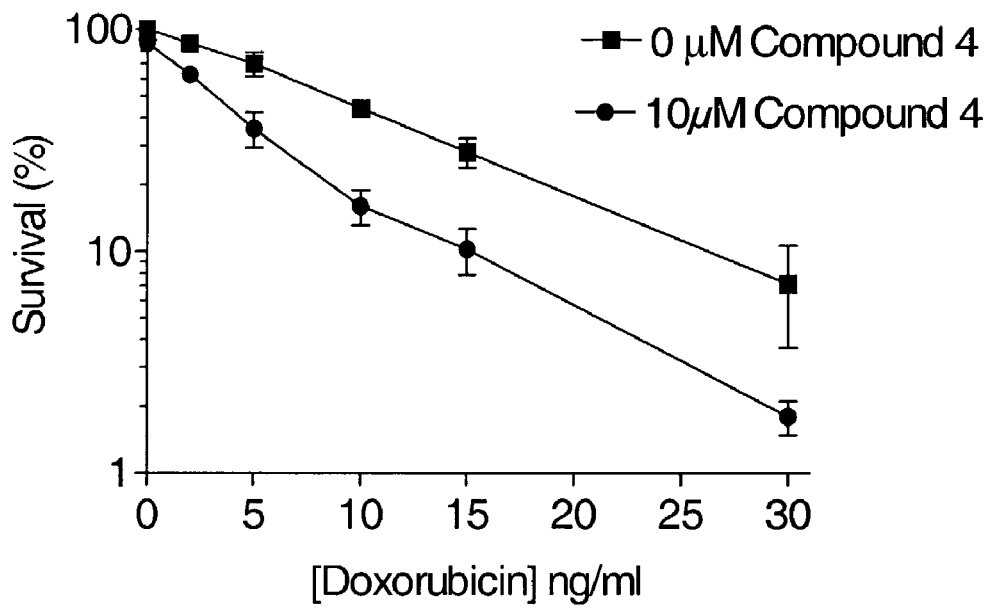

FIG. 4 shows that compound 4 can sensitise cells to doxorubicin. The % survival of LoVo cells was measured with increasing concentrations of doxorubicin, in the absence of compound 4 (■), and in the presence of 10 µM of compound 4 (●).

Figure 5:
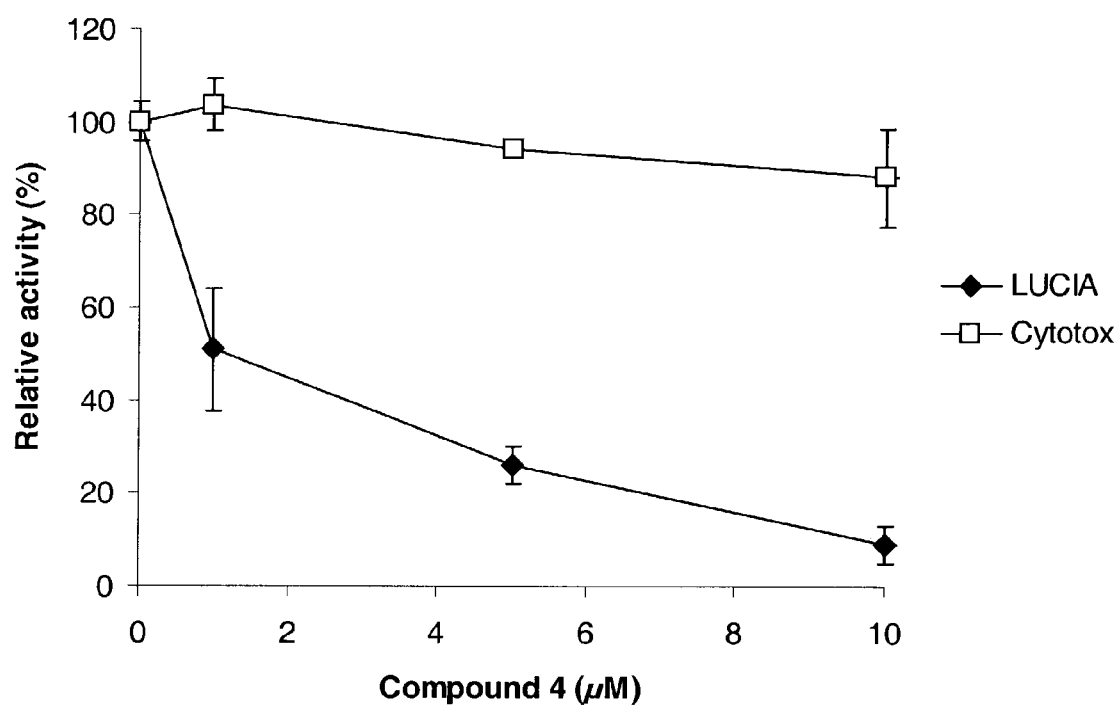

FIG. 5 shows that compound 4 can inhibit recombinant retroviral vector infections. The inhibition of retroviral transduction by the ATM inhibitor Compound 4 was assessed by performing HIV-1 based LUCIA on Jurkat T-cells in the presence of increasing concentrations of compound 4 (♦). Data are presented as transduction efficiency (luciferase signal) relative to untreated control cells. The $IC_{50}$ concentration for HIV-1 infections by compound 4 is around 1 µM. Drug cytotoxicity (□) was determined by MTS formazan dye reduction assays and data are presented as the percentage of viable cells remaining after drug treatment. No significant cytotoxicity was observed over the concentration range of Compound 4 tested.

Figure 6:
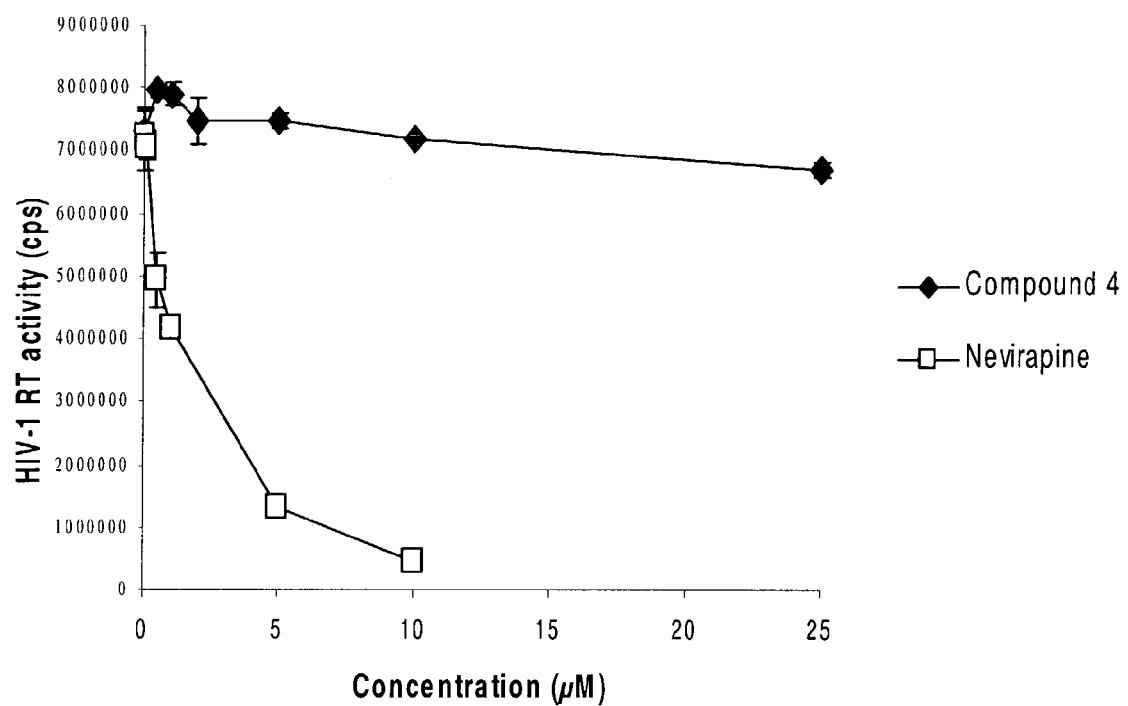

FIG. 6 shows that Compound 4 does not inhibit HIV-1 RT. The inhibition of HIV-1 RT was assessed by performing chemilluminescent HIV-1 reverse transcriptase assays in the presence of increasing amounts of compound 4 (♦). No significant anti-RT activity for compound 4 is observed over the concentration range used. Control RT inhibition using nevirapine (□) is also shown.

Figure 7:
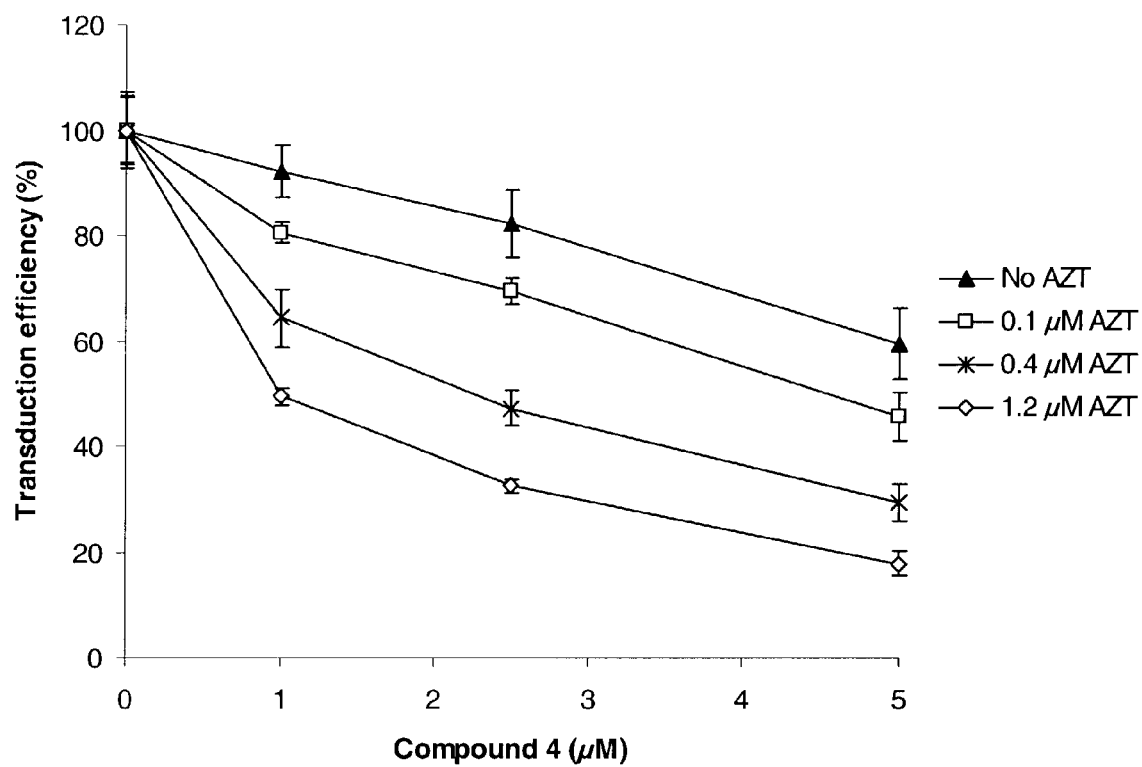

FIG. 7 shows that Compound 4 acts synergistically with AZT to inhibit HIV-1 infections. HIV-1 based LUCIA was performed on HeLa cells with increasing concentrations of Compound 4 in the absence (▲) or presence of 0.1 μM (□), 0.4 μM (*) or 1.2 μM (◇) AZT. Data are presented as transduction efficiency (as determined by luciferase activity) relative to untreated control cells. The combined presence of both Compound 4 and AZT shows enhanced anti-HIV activity when compared to each drug alone.

Figure 8:
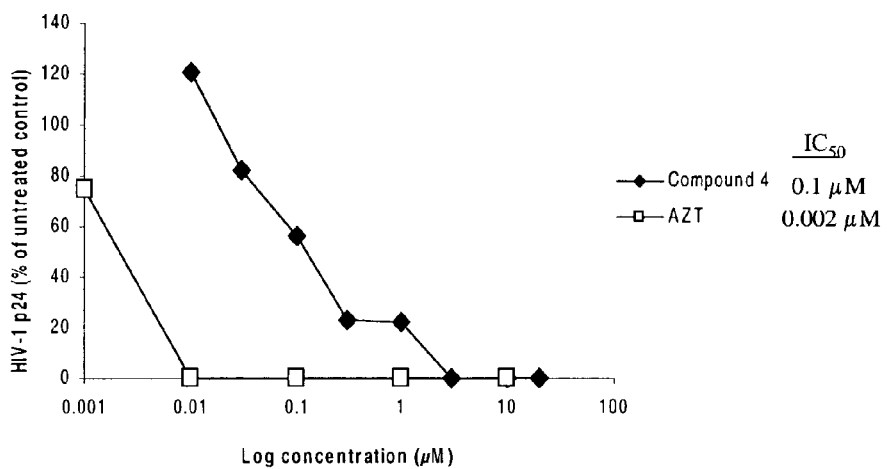
Figure 8:
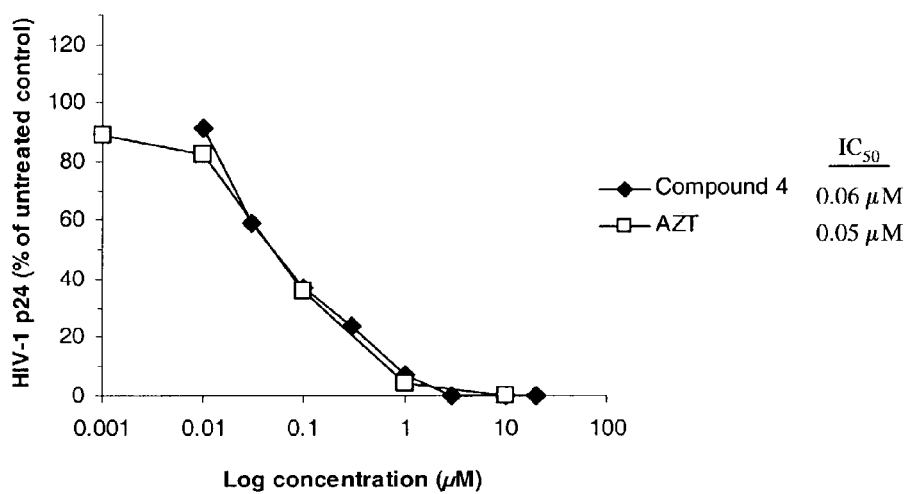
Figure 8:
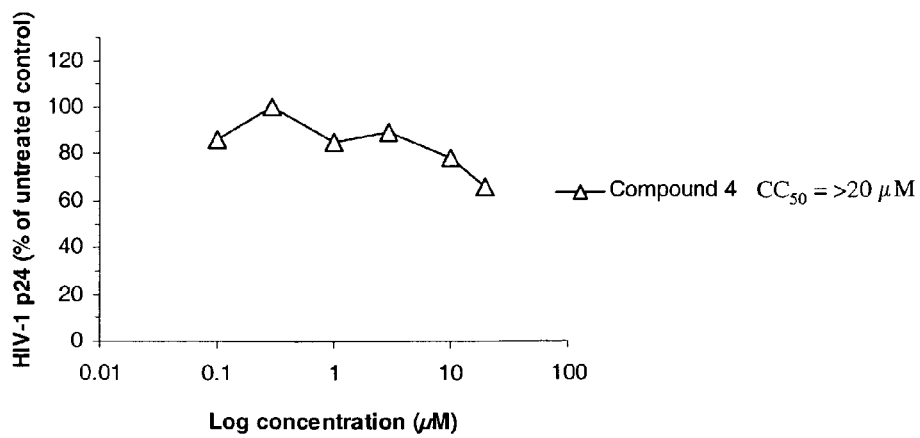

FIG. 8 shows that Compound 4 inhibits HIV-1 replication. 4-day HIV-1 replication assays were performed on C1866 cells in the presence of increasing concentrations of Compound 4 (♦) or AZT (□). HIV-1 titres were quantified by p24 antigen ELISA and data are shown as the percentage of HIV-1 p24 in cell-free supernatants relative to untreated control cells. (A) Replication assays performed using wild type HIV-1 strain (HIV-1$_{HXB2}$ wt). (B) Replication assays performed using an AZT resistant HIV-1 strain (HIV-1$_{HXB2}$ AZTres). Compound 4 inhibits HIV-1 replication equally well in both wild-type and AZT resistant HIV-1 strains. (C) Control drug cytotoxicity (Δ) was determined by XTT dye reduction assays. Data are presented as the percentage of viable cells remaining after drug treatment. No significant cytotoxicity was observed over the effective Compound 4 concentration range shown to inhibit HIV-1 replication.

A) CHEMICAL EXAMPLES

General Experimental Methods

Thin layer chromatography was carried out using Merck Kieselgel 60 F$_{254}$ glass backed plates. The plates were visualized by the use of a UV lamp (254 nm). Silica gel 60 (particle sizes 40–63 μ) supplied by E. M. Merck was employed for flash chromatography. $^1$H NMR spectra were recorded at 300 MHz on a Bruker DPX-300 instrument. Chemical shifts were referenced to tetramethylsilane.

Purification and Identification of Libraries Samples

The samples were purified on Gilson LC units.

Mobile phase A—0.1% aqueous TFA, Mobile phase B—Acetonitrile, Flow rate 6 ml/min., Gradient—typically starting at 90% A/10% B for one minute, rising to 97% B after 15 minutes, holding there for 2 minutes, then back to the starting conditions. Column: Jones Chromatography Genesis 4μ C18 column, 10 mm×250 mm. Peak acquisition based on UV detection at 254 nm.

Mass Specs were recorded on a Finnegan LCQ instrument in positive ion mode.

Mobile phase A—0.1% aqueous formic acid, Mobile phase B—Acetonitrile, Flow rate 2 ml/min., Gradient— starting at 95% A/5% B for one minute, rising to 98% B after 5 minutes, holding there for 3 minutes, then back to the starting conditions. Column—Phenomenex 5μ Luna C18 column, 4.6 mm×50 mm UV detection at 254 nm, PDA detection scanning from 210 to 600 nm.

Mass Spectra of Other Compounds

Mass spectra of non-library compounds and building blocks were recorded on a Micromass ZQ instrument (single quadrupole, operating in electrospray ionisation mode), using a Waters 600 HPLC Pump and 2700 Autosampler.

Mobile Phase A: 0.1% Formic acid in water, Mobile phase B: 0.1% Formic acid in acetonitrile, Flow rate: 2.0 ml/min., Gradient: 5% B to 95% B over 3 mins, hold 3 mins. Column: Varies, but always C18 50 mm×4.6 mm (Currently Genesis C18 4μ. Jones Chromatography). PDA detection: Waters 996, scan range 210–400 nm.

Synthesis of
2-Chloro-6-morpholin-4-yl-pyran-4-one (3)

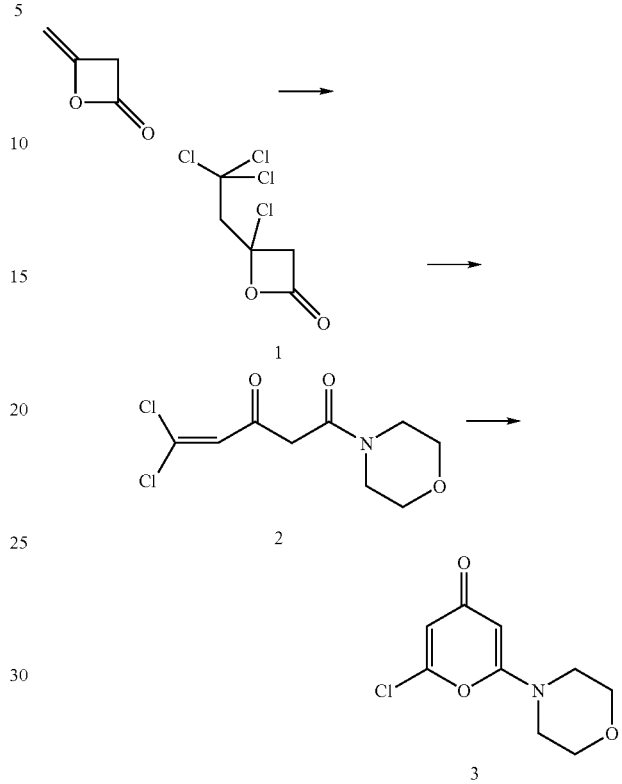

4-Chloro-4-(2,2,2-trichloro-ethyl)-oxetan-2-one (1)

A solution of BCHPO (bis-4-t-butylcyclohexyl)peroxydicarbonate (11.8 g) and diketene (83.5 ml) in CCl$_4$ (300 ml) was added dropwise over 120 minutes to a refluxing solution of CCl$_4$, and was stirred for a further 1 hour. The resulting pale yellow solution was cooled and azeotroped with DCM. The resulting residue was stirred with hexane (3×150 ml) for 10 minutes and the liquor was decanted off through a celite pad. The filtered liquors were combined and concentrated in vacuo to give 1 as a pale yellow oil (125.0 g, 52.9%).

5,5-Dichloro-1-morpholin-4-yl-pent-4-ene-1,3-dione (2)

Two separate solutions of 1 (62.5 g, 0.26 mmol) and morpholine (24.0 g, 0.28 mol) in DCM (120 ml) were added simultaneously to a mixture of NaHCO$_3$ (44.0 g, 0.52 mol) in dry DCM (300 ml). The reaction was maintained at 15° C. over 140 minutes with stirring. The reaction was filtered, washed with DCM (3×100 ml) and the combined organic layers were concentrated in vacuo to a slurry which was then passed through a short silica pad, and further washed with DCM (4×100 ml). The combined organic layers were concentrated in vacuo, suspended in hexane (400 ml) and stirred for 1 hour, filtered and dried to give a cream solid. The solid was suspended in TBME (100 ml), stirred for 15 minutes, filtered, washed with TBME and dried to give 2 as a white powder (47.8 g, 72%). m/z (LC-MS, ESP): 252 (M$^+$+1).

2-Chloro-6-morpholin-4-yl-pyran-4-one (3)

To a suspension of 2 (11.3 g, 44.9 mmol) in dioxane was added perchloric acid (11.4 ml, 0.14 mol) and the reaction was heated at 90° C. under $N_2$ for 1 hour. The reaction was cooled, neutralised with 2M NaOH (75 ml) and filtered. The aqueous layer was extracted with DCM (4×30 ml) and the organic layers were combined and dried over $MgSO_4$. The organic layer was further treated with charcoal and filtered through celite. The dark yellow filtrate was evaporated in vacuo, and the resulting solid was triturated with hexane (50 ml) and dried to give 3 (7.3 g, 75%) as a light yellow powder. m/z (LC-MS, ESP): 216 ($M^+$+1). $^1$H-NMR (300 MHz, DMSO-$d_6$): 3.3 (t, 4H), 3.65 (t, 4H), 5.4 (d, 1H), 6.25 (d, 1H).

Example 1

Synthesis of 2-Thianthren-1-yl-6-morpholin-4-yl-pyran-4-one (4)

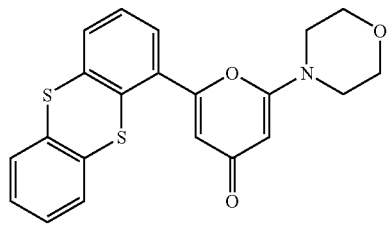

4

2-Chloro-6-morpholin-4-yl-pyran-4-one (3) (863 mg, 4 mmol), thianthrene-1-boronic acid (1.145 g, 4.4 mmol), and ground potassium carbonate (1.105 g, 8 mmol) were suspended in dioxane (10 ml) and degassed (sonication for 5 minutes then saturated with $N_2$). $Pd(PPh_3)_4$ (231 mg, 0.2 mmol) was then added and the reaction mixture was then heated at 90° C. for 24 hours under a vigorous stirring and a $N_2$ atmosphere. The solvent was removed in vacuo and the residue was then suspended in water 50 ml) and extracted with ethyl acetate (3×100 ml). The organics were combined, washed with saturated brine and dried over sodium sulphate. The solvent was removed in vacuo and the residue was purified by column chromatography (silica; ethyl acetate: ethanol; 9:1) to give the title compound as a white solid (70 mg, 4%). $^1$H-NMR (300 MHz, DMSO-$d_6$): $\delta_H$=3.44 (4H, t, J 5 Hz); 3.76 (4H, t, J 5 Hz); 5.57 (1H, d, J 2 Hz); 6.30 (1H, d, J 2 Hz); 7.43 (2H, m); 7.53 (1H, t, 8 Hz); 7.66 (3H, m); 8.49 (1H, dd, J 1 and 8 Hz). m/z (LC-MS, ESP): 396 ($M^+$+1).

Example 2

Synthesis of 2-Phenoxathiin-4-yl-6-morpholin-4-yl-pyran-4-one (5)

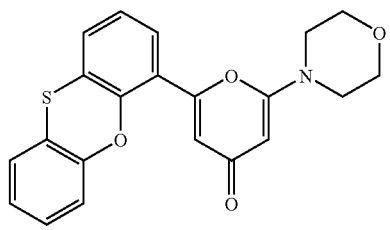

5

2-Chloro-6-morpholin-4-yl-pyran-4-one (3)(863 mg, 4 mmol), phenoxathiin-4-boronic acid (1.07 g, 4.4 mmol), and ground potassium carbonate (1.1 g, 8 mmol) were suspended in dioxane (10 ml) and degassed (sonication for 5 minutes then saturated with $N_2$). $Pd(PPh_3)_4$ (231 mg, 0.2 mmol) was then added and the reaction mixture was then heated at 90° C. for 24 hours under a vigorous stirring and a $N_2$ atmosphere. The solvent was removed in vacuo and the residue was then suspended in water (50 ml) and extracted with ethyl acetate (3×50 ml). The organics were combined, washed with saturated brine and dried over sodium sulphate. The solvent was removed in vacuo and the residue was purified by column chromatography (silica; ethyl acetate: ethanol; 9:1) to give the title compound as a white solid (620 mg, 41%). $^1$H-NMR (300 MHz, DMSO-$d_6$): $\delta$=3.38 (4H, t, J 5 Hz); 3.71 (4H, t, J 5 Hz); 5.49 (1H, d, J 2 Hz); 6.49 (1H, d, J 2 Hz); 7.06 (1H, dd, J 1 and 8 Hz); 7.26 (4H, m); 7.46 (1H, dd, J 1.5 and 8 Hz); 7.55 (1H, dd, J 1.5 and 8 Hz). m/z (LC-MS, ESP): 380 ($M^+$+1).

Example 3

Synthesis of 2-Dibenzofuran-1-yl-6-morpholin-4-yl-pyran-4-one (6)

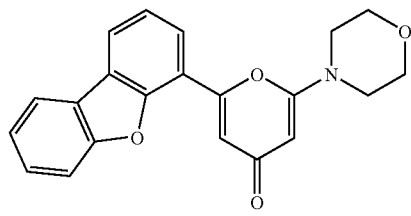

6

2-Chloro-6-morpholin-4-yl-pyran-4-one (3)(22 mg, 0.1 mmol), 4-dibenzofuran-1-boronic acid (28 mg, 0.13 mmol), and caesium carbonate (65 mg, 0.2 mmol) were suspended in dioxane (0.5 ml) and degassed (sonication for 5 minutes then saturated with $N_2$). $Pd(PPh_3)_4$ (5 mg, 0.005 mmol) was then added and the reaction mixture was then heated at 90° C. for 24 hours under a vigorous stirring and a $N_2$ atmosphere. The reaction mixture was purified by preparative HPLC to give the title compound (2.1 mg; 6%). m/z (LC-MS, ESP): 348 ($M^+$+1).

Example 4

Synthesis of 2-Dibenzothiophen-1-yl-6-morpholin-4-yl-pyran-4-one (7)

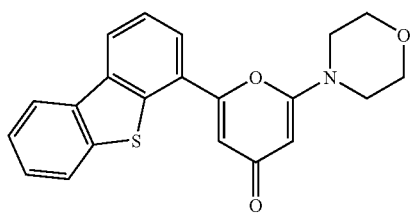

2-Chloro-6-morpholin-4-yl-pyran-4-one (3)(740 mg, 3.43 mmol), dibenzothiophene-1-boronic acid (860 mg, 3.77 mmol), and ground potassium carbonate (964 mg, 6.86 mmol) were suspended in dioxane (10 ml) and degassed (sonication for 5 minutes then saturated with $N_2$). $Pd(PPh_3)_4$ (200 mg, 0.17 mmol) was then added and the reaction mixture was then heated at 90° C. for 24 hours under a vigorous stirring and a $N_2$ atmosphere. The solvent were removed in vacuo and the residue was then suspended in water (50 ml) and extracted with ethyl acetate (3×50 ml). The organics were combined, washed with saturated brine and dried over sodium sulphate. The solvent was removed in vacuo and the residue was purified by column chromatography (silica; ethyl acetate:ethanol; 9:1) to give the title compound as a white solid (80 mg, 6%). $^1$H-NMR (300 MHz, DMSO-$d_6$): $\delta_H$=3.49 (4H, t, J 5 Hz); 3.76 (4H, t, J 5 Hz); 5.53 (1H, d, J 2 Hz); 6.63 (1H, d, J 2 Hz); 7.59 (2H, m); 7.69 (1H, t, J 8 Hz); 7.96 (1H, dd, J 1 and 7.5 Hz); 8.11 (1H, m); 8.47 (1H, m); 8.57 (1H, dd, J 1 and 8 Hz). m/z (LC-MS, ESP): 364 ($M^+$+1).

Example 5

Synthesis of 2-(2-Phenylsulfanyl-phenyl)-6-morpholin-4-yl-pyran-4-one (9)

(a) 2-phenylsulfido-benzene boronic acid (8)

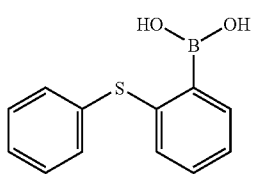

To a cooled (−78° C.), stirred solution of diphenyl sulphide (1.66 ml, 10 mmol) in 30 ml anhydrous THF, was added dropwise under a nitrogen atmosphere 7 ml t-BuLi. Upon addition of t-BuLi the solution turned orange then brown. The mixture was allowed to warm to room temperature and then left stirring for 3 hours. The mixture was cooled (−78° C.). Triethyl borate (2.03 ml, 12 mmol) was added dropwise to the cooled yellow solution turning the solution lime coloured. During this addition, the temperature was monitored and not allowed to rise above −75° C. The solution was then left to warm to room temperature and left stirring for 2 hours. Water was added to the reaction mixture and the aqueous were extracted with diethyl ether. The aqueous layer (pH 14) was acidified to pH 1 with (1 M HCl) and the product was extracted into diethyl ether. The organics were dried over magnesium sulphate and the organics were evaporated off in vacuo, yielding an oily residue (690 mg, 30%), which was used without further purification.

(b) 2-(2'-Phenylsulfido-phenyl)-6-morpholin-4-yl-pyran-4-one (9)

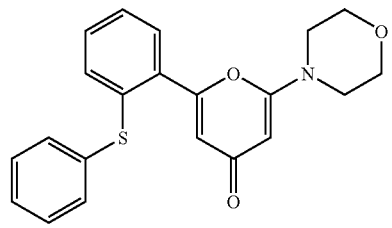

2-Chloro-6-morpholin-4-yl-pyran-4-one (3)(582 mg, 2.7 mmol), 2-phenylsulphido-benzene boronic acid (8) (690 g, 3 mmol), and ground potassium carbonate (819 mg, 5.94 mmol) were suspended in dioxane (10 ml) and degassed (sonication for 5 minutes then saturated with $N_2$). $Pd(PPh_3)_4$ (156 mg, 0.13 mmol) was then added and the reaction mixture was then heated at 90° C. for 24 hours under a vigorous stirring and a $N_2$ atmosphere. The solvent was removed in vacuo and the residue was purified by preparative HPLC to give the title compound (27 mg, 3%). $^1$H-NMR (300 MHz, DMSO-$d_6$): $\delta_H$=3.37 (4H, t); 3.76 (4H, t) 5.45 (1H, d); 6.31 (1H, d); 7.32–7.55 (9H, m). m/z (LC-MS, ESP): 366 ($M^+$+1).

Example 6

Synthesis of 2-(1-Fluoro-9-oxo-9H-thioxanthen-4-yl)-6-morpholin-4-yl-pyran-4-one (13)

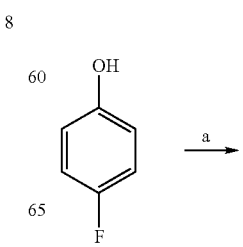

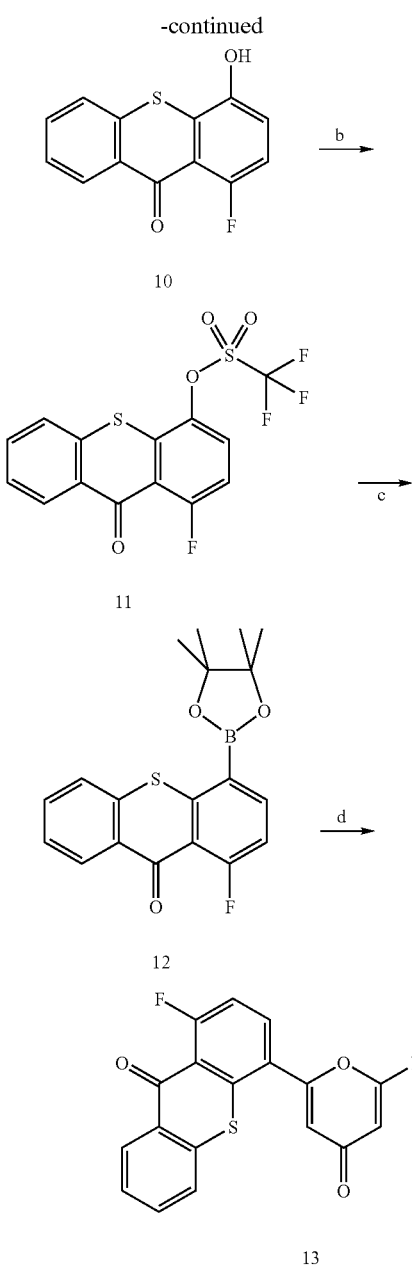

a: H₂SO₄, Thiosalicylic acid;
b: Tf₂O, pyridine;
c: bis(pinacolato)diboron, PdCl₂dppf, dppf, dioxane, 100° C.;
d: chloropyranone, Pd(PPh₃)₄, dioxane, 90° C.

(a) 1-Fluoro-4-hydroxy-thioxanthen-9-one (10)

Thiosalicylic acid (46.26 g, 0.3 mol) and 4-fluorophenol (56.05 g, 0.5 mol) were dissolved in conc. $H_2SO_4$ (750 ml) and the mixture was stirred under nitrogen for 24 hours. The reaction mixture was then poured onto ice (1.5 L) and the yellow precipitate was filtered and washed with water (300 ml). The precipitate was dried at 50° C. for 24 hours and was used without further purification (31.4 g, 42.5%). m/z (LC-MS, ESP): 247 ($M^+$+1).

(b) 1-Fluoro-9-oxo-thioxanthen-4-yl trifluoromethane sulfonate (11)

1-Fluoro-4-hydroxy-thioxanthen-9-one (4.92 g, 20 mmol) was dissolved in dry pyridine (100 ml) and cooled to 0° C. under a nitrogen atmosphere. Triflic anhydride (3.66 ml, 22.3 mmol) was added drop wise to the stirred solution over 5 minutes. The reaction was left overnight and was then poured onto water (300 ml) and the precipitate formed was filtered. The solid was purified through a plug of silica (ethyl acetate:hexane; 1:9) to give the title compound as a white fluffy solid (1.72 g, 22.4%). m/z (LC-MS, ESP): 379 ($M^+$+1).

(c) 1-Fluoro-4-(4,4,5,5-tetramethyl-[1,3,2]dioxaborolan-2-yl)-thioxanthen-9-one (12)

1-fluoro-9-oxo-thioxanthen-4-yl trifluoromethane sulfonate (11) (378 mg, 1 mmol), bis(pinacolato)diboron (305 mg, 1.2 mmol), and ground potassium acetate (294 mg, 3mmol) were suspended in dioxane (5 ml) and degassed (sonication for 5 minutes then saturated with $N_2$). PdCl₂dppf (40 mg, 0.050 mmol) and dppf (27.7 mg, 0.05 mmol) was then added and the reaction mixture was then heated at 100° C. for 24 hrs under a vigorous stirring and a $N_2$ atmosphere. The solvent was removed in vacuo and the residue was purified by column chromatography (silica; ethyl acetate: ethanol; 9:1) to give an oil which was used without further purification (116 mg, 32%). m/z (LC-MS, ESP): 357 ($M^+$+1).

(d) 2-(1-Fluoro-9-oxo-thioxanthen-4-yl)-6-morpholin-4-yl-pyran-4-one (13)

2-Chloro-6-morpholin-4-yl-pyran-4-one (3) (100 mg, 0.46 mmol), 1-Fluoro-4-(4,4,5,5-tetramethyl-[1,3,2]dioxaborolan-2-yl)-thioxanthen-9-one (12) (110 mg, 0.31 mmol), and ground potassium carbonate (63 mg, 0.62 mmol) were suspended in dioxane (5 ml) and degassed (sonication for 5 minutes then saturated with $N_2$). Pd(PPh₃)₄ (18 mg, 0.016 mmol) was then added and the reaction mixture was then heated at 90° C. for 24 hours under a vigorous stirring and a $N_2$ atmosphere. The solvent were removed in vacuo and the residue was then suspended in water (50 ml) and extracted with ethyl acetate (3×50 ml). The organics were combined, washed with saturated brine and dried over sodium sulphate. The solvent was removed in vacuo and the residue was purified by column chromatography (silica; ethyl acetate:ethanol; 9:1) to give the title compound as a white solid (5 mg, 4%). m/z (LC-MS, ESP): 410 ($M^+$+1).

Example 7

Synthesis of 2-(1-Fluoro-9H-thioxanthen-4-yl)-6-morpholin-4-yl-pyran-4-one (17)

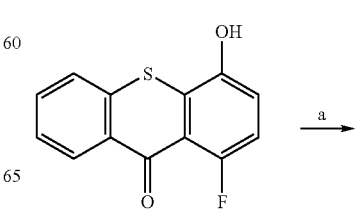

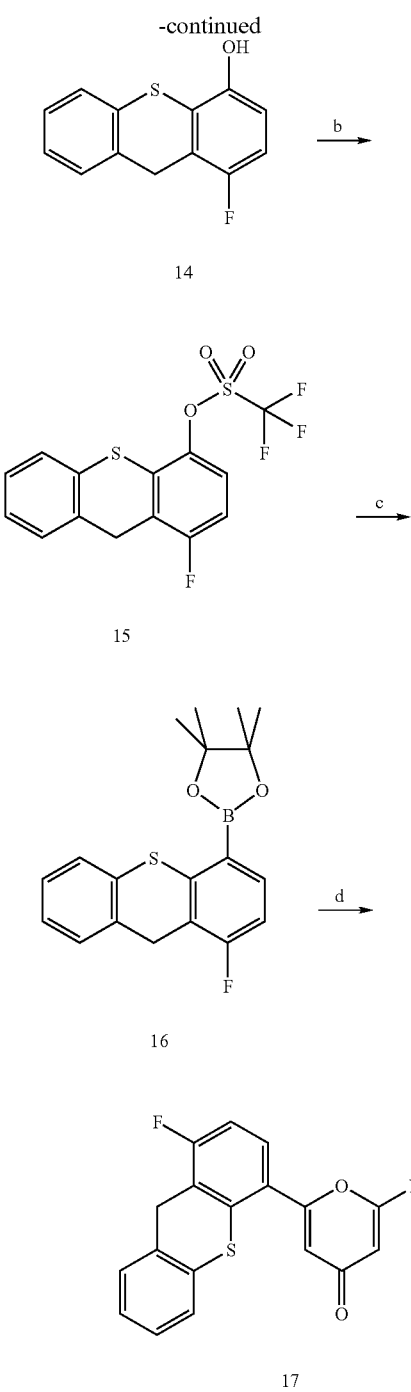

a: BH₃-THF;
b: Tf₂O, pyridine;
c: bis(pinacolato)diboron, PdCl₂dppf, dppf, dioxane, 100° C.;
d: chloropyranone, Pd(PPh₃)₄, dioxane, 90° C.

(a) 1-Fluoro-4-hydroxy-thioxanthen-9-one (14)

1-Fluoro-4-hydroxy-thioxanthen-9-one (4.93 g, 20 mmol) was dissolved in THF (50 ml) and cooled down to 0° C. under a N₂ atmosphere. Borane-tetrahydrofuran complex (1M, 60 ml, 60 mmol) was added drop wise to the stirred solution over 10 minutes. The reaction was left to react overnight and was then quenched with acetone (100 ml). The mixture was evaporated to dryness and the residue was taken into water (200 ml). The product was extracted in ethyl acetate (3×100 ml) and the organics were combined, dried over sodium sulphate and evaporated in vacuo. The residue was purified by column chromatography (silica, hexane: ethyl acetate, 9:1) to give a white solid which is readily oxidised by air (2.19 g, 47%). $^1$H-NMR (300 MHz, DMSO-d₆): $\delta_H$=3.86 (2H, s); 6.73 (1H, m); 6.95 (1H, m); 7.24 (2H, m) 7.47 (2H, m); 10.07 (1H, s).

(b) 1-Fluoro-9H-thioxanthen-4-yl trifluoromethane sulfonate (15)

1-Fluoro-4-hydroxy-thioxanthen-9-one (1.66 g, 7.15 mmol) was dissolved in dry pyridine (35 ml) and cooled to 0° C. under a nitrogen atmosphere. Triflic anhydride (2.22 g, 7.87 mmol) was added dropwise to the stirred solution over 5 minutes. The reaction was left to react for 4 hours at room temperature and was then pour onto water (350 ml). The milky solution was extracted with DCM (3×200 ml), the organics were combined and dried over magnesium sulphate. The solvent was removed in vacuo and the solid obtained was purified through a plug of silica (ethyl acetate: hexane; 3:97) to give the title compound as a white fluffy solid (2.55 g, 98%). $^1$H-NMR (300 MHz, DMSO-d₆): $\delta_H$=3.86 (2H, s); 7.3–7.6 (6H, m)

(c) 1-Fluoro-4-(4,4,5,5-tetramethyl-[1,3,2]dioxaborolan-2-yl)-9H-thioxanthe (16)

1-fluoro-9H-thioxanthen-4-yl trifluoromethane sulfonate (1 g, 2.75 mmol), bis(pinacolato)diboron (840 mg, 3.30 mmol), and ground potassium acetate (809 mg, 8.25 mmol) were suspended in dioxane (7 ml) and degassed (sonication for 5 minutes then saturated with N₂). PdCl₂dppf (0.112 mg, 0.138 mmol) and dppf (77 mg, 0.138 mmol) was then added and the reaction mixture was then heated at 100° C. for 24 hours under a vigorous stirring and a N₂ atmosphere. The solvent were removed in vaccuo and the residue was purified by column chromatography (silica; ethyl acetate:ethanol; 9:1) to give an oil which was used without further purification (460 mg, 49%).

(d) 2-(1-Fluoro-9H-thioxanthen-4-yl)-6-morpholin-4-yl-pyran-4-one (17)

2-Chloro-6-morpholin-4-yl-pyran-4-one (3)(252 mg, 1.17 mmol), 1-Fluoro-4-(4,4,5,5-tetramethyl-[1,3,2]dioxaborolan-2-yl)-9H-thioxanthe (400 mg, 1.17 mmol), and ground potassium carbonate (239 mg, 2.34 mmol) were suspended in dioxane (7 ml) and degassed (sonication for 5 minutes then saturated with N₂). Pd(PPh₃)₄ (67 mg, 0.059 mmol) was then added and the reaction mixture was then heated at 90° C. for 24 hrs under a vigorous stirring and a N₂ atmosphere. The solvent were removed in vaccuo and the residue was purified by column chromatography (silica; ethyl acetate: ethanol; 9:1) to give an off white solid which was triturated in ether and gave the title compound as a white solid (72.3 mg, 16%). $^1$H-NMR (300 MHz, DMSO-d₆): $\delta_H$=3.41 (4H, t); 3.71 (4H, t) 5.50 (1H, d); 6.21 (1H, d); 7.25–7.35 (3H, m); 7.52–7.62 (3H, m). m/z (LC-MS, ESP): 396 (M$^+$+1).

Example 8

Synthesis of 2-Thianthren-1-yl-6-morpholin-4-yl-pyran-4-thione (18)

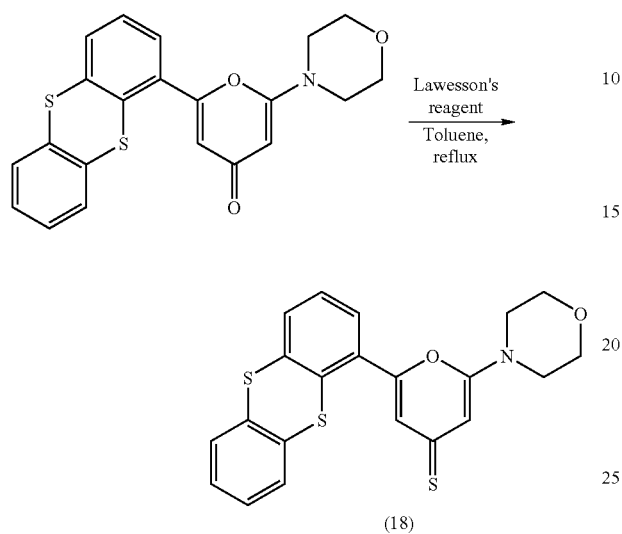

2-Thianthren-1-yl-6-morpholin-4-yl-pyran-4-one (4)(140 mg, 0.354 mmol) was dissolved in toluene (5 ml). Lawesson's reagent (215 mg, 0.53 mmol) was added to the solution and the mixture was refluxed overnight under nitrogen with stirring. The toluene was evaporated off in vacuo and the residue was purified via column chromatography (silica, dichloromethane) to give the desired compound (18) as dark orange solid (27 mg, 18%). $^1$H-NMR (300 MHz, DMSO-$d_6$): $\delta_H$=3.56 (4H, t, J 5 Hz); 3.73 (4H, t, J 5 Hz); 7.83 (1H, d, J 2 Hz); 7.76 (1H, d, J 2 Hz); 7.30–7.80 (7H, m). m/z (LC-MS, ESP):412 (M$^+$+1).

Example 9

2-(7-Amino-9H-thioxanthen-4-yl)-6-morpholin-4-yl-pyran-4-one N-amide derivatives

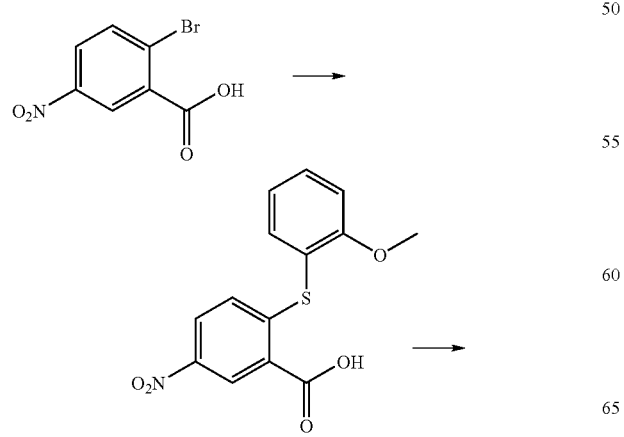

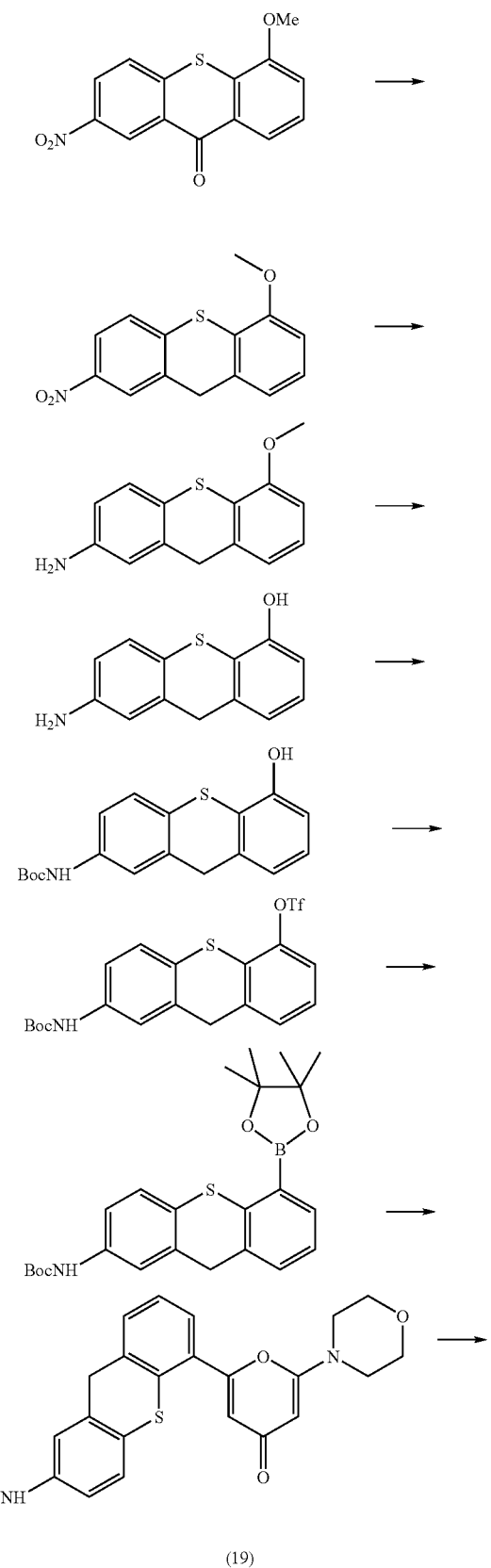

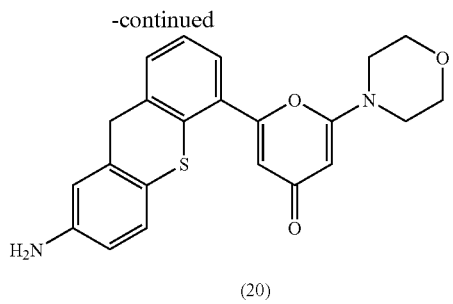

(20)

2-(2-Methoxy-phenylsulfanyl)-5-nitro-benzoic acid

2-Methoxythiophenol (9.9 ml, 81.29 mmol) was added to a solution of KOH (18.24 g, 325.18 mmol) in water (80 ml) degassed for 15 minutes. 2-Bromo-5-nitrobenzoic acid (20.0 g, 81.29 mmol) and copper bronze (258 mg, 4.06 mmol) were added to the reaction mixture, which was refluxed overnight. The reaction was stopped and the mixture was filtered through a celite pad and washed with 2M NaOH then water (50 ml). The filtrate was acidified (pH 1) with concentrated HCl. The precipitate formed was filtered and dried overnight in a vacuum oven (50° C.) to give the crude title compound (26.0 g) as a pale yellow solid. The product was used without further purification.

5-Methoxy-2-nitro-thioxanthene-9-one 2-(2-Methoxy-phenylsulfanyl)-5-nitro-benzoic acid (13.00 g, 42.58 mmol) was suspended in methanesulphonic acid (100 ml) and heated at 100° C. The crude mixture was slowly poured onto ice with vigorous stirring then neutralized with conc. ammonia solution. The precipitate was filtered and washed with water. The yellow/lime colored solid was dried under vacuum at 50° C. to give the crude title compound which was used without any further purification (12 g, 98%). m/z (LC-MS, ESP), RT=4.89 min, (M$^+$+1)=288.

5-Methoxy-2-nitro 9H-thioxanthene

To a cooled (0° C.) suspension of 5-methoxy-2-nitro-thioxanthene-9-one (24.46 g, 85.13 mmol) in anhydrous tetrahydrofuran (40 ml) under nitrogen atmosphere, was added drop wise borane-THF complex (170 ml, 1.0M in THF). The mixture was allowed to warm to room temperature with stirring overnight. The reaction mixture was cooled (0° C.) and the excess borane was quenched with acetone. The solvent was evaporated in vacuo. The residue was purified by flash chromatography (1:1, dichloromethane/hexane) to give the title compound (11.59 g, 50%) as a bright yellow amorphous solid. $^1$HNMR (300 MHz, DMSO-d$_6$): δ$_H$=3.86 (3H, s), 4.03 (2H, s), 7.00 (2H, dd), 7.28 (1H, t), 7.73 (1H, d), 8.05 (1H, dd), 8.28 (1H, d).

5-Methoxy-9H-thioxanthen-2-ylamine

5-Methoxy-2-nitro 9H-thioxanthene (11.59 g, 42.40 mmol) was suspended in ethyl acetate (250 ml). SnCl$_2$.2H$_2$O (47.84 g, 212 mmol) was added and the clear yellow solution was stirred at 50° C. overnight. The reaction was quenched with NaOH (2M) and then extracted with ethyl acetate (3×300 ml). The organics were washed with saturated brine (100 ml), dried over magnesium sulphate and the solvents were removed in vacuo to give the title compound (10.32 g, 100%) as viscous yellow oil. The oil was used without further purification. $^1$HNMR (300 MHz, DMSO-d$_6$): δ$_H$=3.83 (3H, s), 3.67 (2H, s), 5.14 (2H, bs), 6.43 (1H, dd), 6.61 (1H, d), 6.89 (1H, d), 6.99 (1H, d), 7.06 (1H, d), 7.18 (1H, t). m/z (LC-MS, ESP), RT=3.88 min, (M$^+$+1)=244.

7-Amino-9H-thixanthen-4-ol

5-Methoxy-9H-thioxanthen-2-ylamine (10.32 g, 41.09 mmol) and pyridine hydrochloride (49.0 g, 424 mmol) were heated at 200° C. under nitrogen atmosphere for 5 hours. The black reaction mixture was allowed to cool down to room temperature and water (50 ml) was then added. The mixture was neutralized with NaOH (2M) to pH 7 then extracted with dichloromethane (4×100 ml). The organics were washed with saturated brine, dried over MgSO$_4$) and concentrated in vacuo to give a black oil. This oil was purified by flash chromatography (dichloromethane) to give the title compound (7.78 g, 80%) as dark brown oil which was used without further purification. $^1$HNMR (300 MHz, DMSO-d$_6$): δ$_H$=3.61 (2H, s), 5.08 (2H, bs), 6.42 (1H, dd), 6.58 (1H, d), 6.69 (1H, d), 6.81 (1H, d) 6.95–7.06 (2H, m), 9.88 (1H, bs); m/z (LC-MS, ESP), RT=3.23 min, (M$^+$+1)=230.

(5-Hydroxy-9H-thioxanthen-2-yl)-carbamic acid tert-butyl ester

To a solution of 7-amino-9H-thixanthen-4-ol (7.77 g, 81.32 mmol) in THF (14 ml) was added dropwise di-tert-butyl dicarbonate (17.74 mg, 0.49 mmol) in THF (4 ml). The reaction was stirred at room temperature under nitrogen atmosphere. Upon completion of the reaction the solvent was evaporated. The residue was taken up in methanol (50 ml), and sodium hydroxide (4.06 g, 101.16 mmol) was added. The dark brown mixture was refluxed for 20 minutes. The solvent was evaporated in vacuo and the oil was taken up in water, extracted with ethyl acetate, dried over MgSO$_4$ and evaporated in vacuo to give the crude product. The dark brown oil was purified by flash chromatography (dichloromethane) to give the title compound (4.2 g, 38%), as a cream coloured amorphous solid. $^1$HNMR (300 MHz, DMSO-d$_6$): δ$_H$=3.74 (2H, s), 6.74 (1H, d), 6.87 (1H, d), 7.04 (1H, t), 7.23–7.33 (2H, m), 7.57 (1H, bs), 10.03 (1H, bs).

(5-Trifluoromethanesulfonyl-9H-thioxanthen-2-yl)-carbamic acid tert-butyl ester To a cooled (0° C.) golden colored solution of (5-hydroxy-9H-thioxanthen-2-yl)-carbamic acid tert-butyl ester (4.0 g, 12.14 mmol) in anhydrous pyridine (8 ml) under nitrogen atmosphere was added trifluoromethanesulphonic anhydride (2.36 ml, 13.35 mmol) drop wise. The solution turned deep orange upon addition of trifluoromethanesulphonic anhydride. The reaction was allowed to warm to room temperature. After 10 minutes of stirring at this temperature the solution was poured into water (20 ml). The product was extracted with ethyl acetate. The organics were washed with saturated brine, dried over MgSO$_4$ and concentrated in vacuo to give the title compound (5.6 g, 100%) as a dark orange solid.

[5-(4,4,5,5-Tetramethyl-[1,3,2]dioxaborolan-2-yl)-9H-thioxanthen-2-yl]-carbamic acid tert-butyl ester (5-Trifluoromethanesulfonyl-9H-thioxanthen-2-yl)-carbamic acid tert-butyl ester (3.31 g, 7.17 mmol), bis(pinacolato)diboron (2.18 g, 8.6 mmol) and potassium acetate (2.11 g, 21.5 mmol) in 1,4-dioxane (20 ml) was degassed for 15 minutes. To the yellow suspension was then added PdCl$_2$ (dppf) (293 mg, 0.36 mmol) and dppf (199 mg, 0.36 mmol). The dark red mixture was heated to 90° C. under a N$_2$ atmosphere for 48 hours. The crude mixture was purified by flash chromatography (dichloromethane) to give viscous brown oil (3.15 g), which was used without any further purification.

[5-(6-Morpholin-4-yl-4-oxo-4H-pyran-2-yl)-9H-thioxanthen-2-yl]-carbamic acid tert-butyl ester (19)

[5-(4,4,5,5-Tetramethyl-[1,3,2]dioxaborolan-2-yl)-9H-thioxanthen-2-yl]-carbamic acid tert-butyl ester (1.02 g, 2.32 mmol), 2-chloro-6-morpholin-4-yl-pyran-4-one (3) (0.60 g, 2.78 mmol) and K$_2$CO$_3$ (0.64 g, 4.64 mmol) were dissolved in dry 1,4-dioxane (ml). The mixture was degassed for 15 minutes and Pd(PPh$_3$)$_4$ (0.13 g, 0.12mol) was then added The dark brown mixture was heated to 90° C. under an atmosphere of N$_2$ for 24 hour. The reaction mixture was concentrated in vacuo and water (50 ml) was added. The brown solid was filtered and washed with water (1.21 g, 88%). m/z (LC-MS, ESP), RT=4.6 minutes, (M$^+$+1)=493.

2-(7-Amino-9H-thioxanthen-4-yl)-6-morpholin-4-yl-pyran-4-one (20)

To a solution of [5-(6-Morpholin-4-yl-4-oxo-4H-pyran-2-yl)-9H-thioxanthen-2-yl]-carbamic acid tert-butyl ester (19)(1.08 g, 2.19 mmol) in dichloromethane (10 ml) was added trifluoroacetic acid (2 ml) and left under stirring at room temperature overnight. The solvent was dried in vacuo revealing a viscous dark brown liquid. Saturated sodium bicarbonate solution (20 ml) was added to the residue, which was left to stir for 20 mins. The brown precipitate was filtered, washing with water and left to dry in the vacuum oven overnight (0.77 g, 90%). $^1$HNMR (300 MHz, DMSO-d$_6$): $\delta_H$=3.40 (4H, t), 3.70 (4H, t), 3.77 (2H, s), 5.23 (2H, bs), 5.50 (1H, d), 6.17 (1H, d), 6.44 (1H, dd), 6.65 (1H, d), 7.09 (1H, d), 7.35 (1H, t), 7.47–7.59 (2H, m); m/z (LC-MS, ESP), RT=3.51 minutes, (M$^+$+1)=392.

2-(7-Amino-9H-thioxanthen-4-yl)-6-morpholin-4-yl-pyran-4-one N-amide derivatives (a) To a small test tube was added 2-(7-amino-9H-thioxanthen-4-yl)-6-morpholin-4-yl-pyran-4-one (20)(20 mg, 0.05 mmol), dry dimethylacetamide (0.5 ml), triethylamine (0.01 ml, 0.08 mmol) and the desired acid chloride (0.08 mmol) with stirring overnight. The reaction was purified by preparative HPLC to give the desired products, which are shown below:

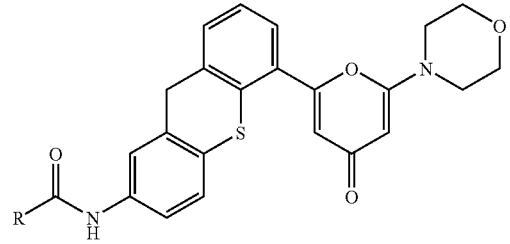

| Compound | R | Purity | Retention Time (Mins) | M$^+$ + 1 |
|---|---|---|---|---|
| 21 | phenyl acetate | 90 | 3.46 | 435 |
| 22 | methoxymethyl | 90 | 3.62 | 465 |
| 23 | methoxycarbonylmethyl | 90 | 3.58 | 493 |
| 24 | cyclopropyl | 95 | 3.82 | 461 |
| 25 | methyl butanoate | 95 | 3.66 | 521 |

-continued
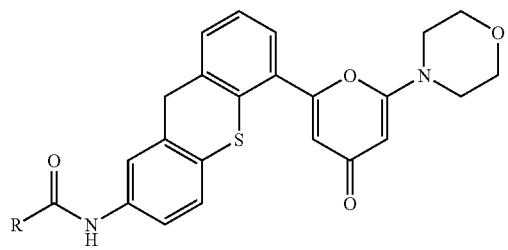
| Compound | R | Purity | Retention Time (Mins) | M+ + 1 |
|---|---|---|---|---|
| 26 | 3-pyridyl | 90 | 3.53 | 498 |
| 27 | 2-furyl | 90 | 4.16 | 487 |
| 28 | 4-pyridyl | 90 | 3.43 | 498 |
| 29 | 2-methoxyphenyl | 95 | 4.44 | 527 |
| 30 | 2-thienyl | 90 | 4.1 | 503 |
| 31 | 2-thienylmethyl | 95 | 4.03 | 517 |
| 32 | cyclobutyl | 95 | 3.99 | 475 |
| 33 | 3,5-dimethylisoxazol-4-yl | 90 | 4.13 | 516 |
| 34 | methoxycarbonyl | 90 | 3.64 | 479 |
| 35 | 3-hydroxy-1-methylpyrazol-5-yl | 90 | 4.12 | 517 |

-continued
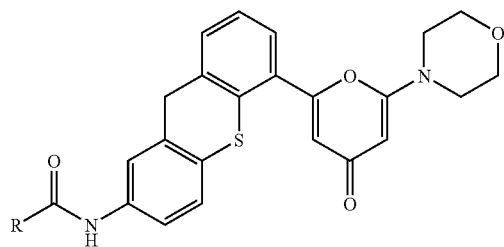
| Compound | R | Purity | Retention Time (Mins) | M+ + 1 |
|---|---|---|---|---|
| 36 | | 90 | 3.43 | 546 |
| 37 | | 90 | 3.91 | 555 |
| 38 | | 90 | 4.16 | 587 |
| 39 | | 90 | 3.59 | 507 |
| 40 | | 90 | 3.5 | 493 |
| 41 | | 90 | 4.1 | 569 |
| 42 | | 85 | 4.31 | 515 |

-continued

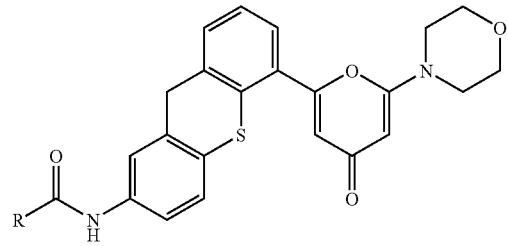

| Compound | R | Purity | Retention Time (Mins) | M⁺ + 1 |
|---|---|---|---|---|
| 43 | 2,3-dihydrobenzofuran-5-yl | 95 | 4.16 | 539 |
| 44 | 6-fluoro-4H-benzo[1,3]dioxin-8-yl | 95 | 4.46 | 573 |
| 45 | 5-methylisoxazol-3-yl | 95 | 4.02 | 502 |
| 46 | 2-(thiophen-2-yl)thiazol-4-yl | 95 | 4.72 | 586 |
| 47 | isoxazol-5-yl | 95 | 3.67 | 488 |
| 48 | HOOC-CH₂-CH₂- | 95 | 3.42 | 493 |
| 49 | 2-(HOOC)-cyclopropyl | 95 | 3.38 | 505 |
| 50 | HOOC-C(F)₂-C(F)₂- | 90 | 3.48 | 565 |

(b) To a small test tube was added 2-(7-amino-9H-thioxanthen-4-yl)-6-morpholin-4-yl-pyran-4-one (20)(20 mg, 0.05 mmol), dry dimethylacetamide (0.5 ml), triethylamine (8 μl, 0.06 mmol) and chloroacetyl chloride (4 μl, 0.06 mmol) with stirring overnight. The appropriate amine or thiol (20 mg or 20 μl) was then added and left to stir at room temperature overnight. The reaction was purified by preparative HPLC to give the desired products, which are shown below:

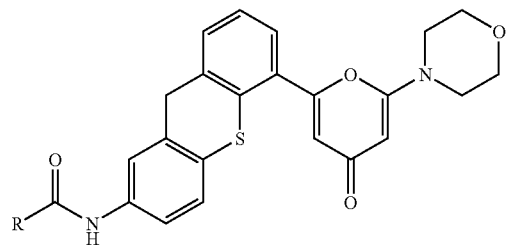
| Compound | R | Purity | Retention Time (Mins) | M+ + 1 |
|---|---|---|---|---|
| 51 | piperidine-CH2-* | 90 | 3.07 | 518 |
| 52 | piperazine-CH2-* | 95 | 2.98 | 519 |
| 53 | 4-methylpiperazine-CH2-* | 95 | 2.98 | 533 |
| 54 | (HOCH2CH2)2N-CH2-* | 95 | 2.98 | 538 |
| 55 | (MeOCH2CH2)2N-CH2-* | 95 | 3.23 | 566 |
| 56 | HOCH2CH2-NH-CH2-* | 95 | 2.93 | 494 |
| 57 | H2N-CH2CH2-NH-CH2-* | 95 | 2.74 | 493 |
| 58 | pyrrolidine-CH2-* | 95 | 3.06 | 504 |

-continued

| Compound | R | Purity | Retention Time (Mins) | M⁺ + 1 |
|---|---|---|---|---|
| 59 | 4-methyl-1,4-diazepan-1-ylmethyl | 90 | 2.99 | 547 |
| 60 | 1,4-diazepan-1-ylmethyl | 95 | 2.93 | 533 |
| 61 | azepan-1-ylmethyl | 95 | 3.82 | 532 |
| 62 | (3-morpholinopropyl)aminomethyl | 95 | 2.77 | 577 |
| 63 | (4-methoxybenzyl)aminomethyl | 95 | 3.18 | 570 |
| 64 | (1H-1,2,4-triazol-3-ylthio)methyl | 95 | 3.4 | 534 |
| 65 | (2-(diethylamino)ethyl)aminomethyl | 95 | 3.1 | 506 |
| 66 | aminomethyl | 95 | 2.96 | 450 |
| 67 | (2-morpholinoethyl)aminomethyl | 95 | 2.97 | 563 |
| 68 | ((tetrahydrofuran-2-yl)methyl)aminomethyl | 95 | 3.16 | 534 |

(c) To a small test tube was added 2-(7-amino-9H-thioxanthen-4-yl)-6-morpholin-4-yl-pyran-4-one (20) (20 mg, 0.05 mmol), dry dimethylacetamide (0.5 ml), triethylamine (8 µl, 0.06 mmol) and 3-bromopropionyl chloride (5 µl, 0.05 mmol) with stirring overnight. The appropriate amine or thiol (20 mg or 20 µl, hydrochloride salts were freed by addition of triethylamine) was then added and left to stir at room temperature overnight. The reaction was purified by preparative HPLC to give the desired products, which are shown below:

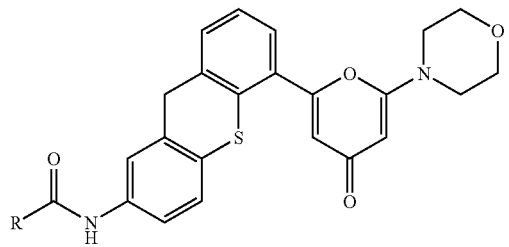
| Compound | R | Purity | Retention Time (Mins) | M+ + 1 |
|---|---|---|---|---|
| 69 | piperidine-N-CH2CH2-* | 90 | 3.17 | 532 |
| 70 | HN-piperazine-N-CH2CH2-* | 90 | 2.88 | 533 |
| 71 | Me-N-piperazine-N-CH2CH2-* | 95 | 2.98 | 547 |
| 72 | (HOCH2CH2)2N-CH2CH2-* | 95 | 2.95 | 552 |
| 73 | (MeOCH2CH2)2N-CH2CH2-* | 95 | 3.19 | 580 |
| 74 | HOCH2CH2-NH-CH2CH2-* | 95 | 2.95 | 508 |
| 75 | H2N-CH2CH2-NH-CH2CH2-* | 90 | 2.76 | 507 |
| 76 | pyrrolidine-N-CH2CH2-* | 95 | 3.08 | 518 |
| 77 | Me-N-homopiperazine-N-CH2CH2-* | 90 | 2.81 | 561 |
| 78 | HN-homopiperazine-N-CH2CH2-* | 95 | 2.83 | 547 |

-continued
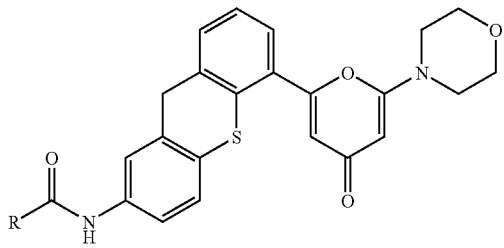
| Compound | R | Purity | Retention Time (Mins) | M+ + 1 |
|---|---|---|---|---|
| 79 | azepan-1-yl-ethyl | 90 | 3.2 | 546 |
| 80 | morpholin-4-yl-propyl-NH-ethyl | 95 | 2.84 | 591 |
| 81 | 4-methoxybenzyl-NH-ethyl | 95 | 3.3 | 584 |
| 82 | 1H-1,2,4-triazol-3-ylthio-ethyl | 95 | 3.43 | 548 |
| 83 | diethylamino-ethyl | 90 | 3.06 | 520 |
| 84 | H₂N-ethyl | 90 | 2.98 | 464 |
| 85 | morpholin-4-yl-propyl-NH-ethyl | 95 | 2.89 | 577 |
| 86 | tetrahydrofuran-2-yl-methyl-NH-ethyl | 95 | 3.14 | 548 |
Example 10
2-(4-Hydroxy-9H-thioxanthen-1-yl)-6-morpholin-4-yl-pyran-4-one ether derivatives
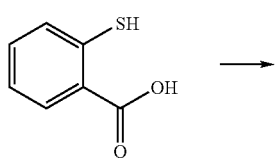
-continued
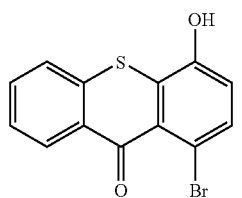

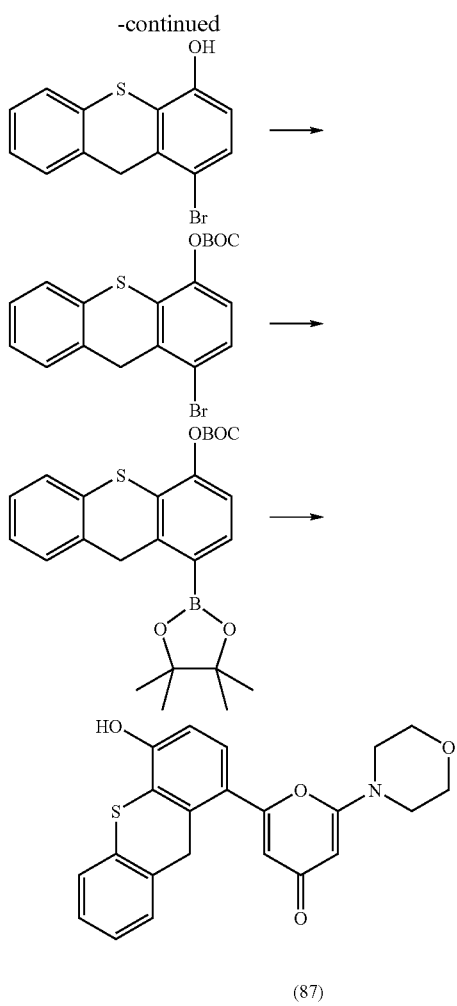

(87)

1-Bromo-4-hydroxy-thioxanthen-9-one

Thiosalicylic acid (20.0 g, 129.71 mmol) and 4-bromophenol (35.9 g, 207.53 mmol) were suspended in conc. H₂SO₄ (200 ml) and stirred for 48 hours. The red solution was slowly poured onto ice (500 ml) with vigorous stirring. The resulting yellow precipitate was filtered, and dried in a vacuum oven (50° C.) to give the title compound (24.23 g, 61%) as a yellow amorphous solid. m/z (LC-MS, ESP), RT=4.39 min, (M⁻−1)=305–307.

1-Bromo-9H-thioxanthen-4-ol

To a cooled 0° C.) suspension of 1-bromo-4-hydroxy-thioxanthen-9-one (24.23 g, 78.88 mmol) in anhydrous tetrahydrofuran (40 ml) under nitrogen atmosphere, was added dropwise borane-THF complex (237 ml, 1M in THF). The cloudy mixture was allowed to warm to room temperature and was left stirring overnight. The suspension dissolved gradually as the reaction progressed giving a yellow solution. The reaction mixture was cooled (0° C.) and the excess borane was quenched with acetone. The yellow solution was evaporated in vacuo. The resulting oil was purified by flash chromatography (4:1, hexane/ethyl acetate) to give the title compound (11.50 g, 50%). m/z (LC-MS, ESP), RT=4.84 min, (M⁻−1)=291–293.

Carbonic acid tert-butyl ester 1-(4,4,5,5-tetramethyl-[1,3,2]dioxaborolan-2-yl)-9H-thioxanthen-4-yl ester To a stirred solution of 1-bromo-9H-thioxanthen-4-ol (11.50 g, 39.22 mmol) in pyridine (7 ml) was added triethylamine (8.15 ml, 58.83 mmol). To the solution was added dropwise di-tert-butyl dicarbonate (9.41 g, 3.14 mmol) in pyridine (4 ml). After 1 hour of stirring the crude reaction mixture was poured into water (100 ml) and extracted with dichloromethane (3×100 ml). The organics were washed with sat. brine (50 ml), dried over MgSO₄ and the solvent was evaporated in vacuo to give the title compound (10.40 g, 67%) as a clear viscous oil. ¹HNMR (300 MHz, DMSO-d₆): $\delta_H$=1.53 (9H, s), 4.09 (2H, s), 7.15–7.65 (6H, m).

Carbonic acid tert-butyl ester 1-(4,4,5,5-tetramethyl-[1,3,2]dioxaborolan-2-yl)-9H-thioxanthen-4-yl ester Carbonic acid tert-butyl ester 1-(4,4,5,5-tetramethyl-[1,3,2]dioxaborolan-2-yl)-9H-thioxanthen-4-yl ester (5.00 g, 12.71 mmol), anhydrous potassium acetate (3.74 g, 38.13 mmol), 1,1'-bis(diphenylphosphino)ferrocene (352 mg, 0.64 mmol) and bis(pinacolato)diboron (3.87 g, 15.25 mmol) were suspended in anhydrous dioxane (8 ml) under nitrogen atmosphere. The mixture was degassed for 10 minutes and dichloro[1,1'-bis(diphenylphosphino)ferrocene]palladium (II) dichloromethane adduct (514 mg, 0.64 mmol) was added to the mixture. The reaction was heated at 90° C. under nitrogen atmosphere for 24 hours. The crude reaction mixture was purified by flash chromatography (dichloromethane), to give the title compound (3.02 g) as a crude brown oil which was used without further purification.

2-(4-Hydroxy-9H-thioxanthen-1yl)-6-morpholin-4-yl-pyran-4-one (87)

Carbonic acid tert-butyl ester 1-(4,4,5,5-tetramethyl-[1,3,2]dioxaborolan-2-yl)-9H-thioxanthen-4-yl ester (3.00 g, 6.81 mmol), 2-chloro-6-morpholin-4-yl-pyran-4-one (1.22 g, 5.67 mmol) and potassium carbonate (2.07 g, 14.98 mmol) were suspended in anhydrous dioxane (6 ml) under nitrogen atmosphere. The solution was degassed for 15 minutes. To the solution tetrakis(triphenylphosphino) palladium (291 mg, 5% eq.) was added. The mixture was degassed for a further 5 minutes. The reaction was heated at 90° C. under nitrogen atmosphere for 24 hours. The solvent was evaporated in vacuo and the crude mixture was purified by column chromatography (9:1, ethyl acetate/ethanol), to yield the title compound (421 mg, 16%) as a light yellow amorphous solid. ¹H NMR (300 MHz, DMSO-d6): $\delta_H$=3.33 (4H, t), 3.67 (4H, t), 3.88 (2H, s), 5.45 (1H, d), 6.05 (1H, d), 6.87 (1H, d), 7.24–7.65 (5H, m), 10.62 (1H, bs); m/z (LC-MS, ESP), RT=3.96 min, (M⁺+1)=394.

2-(4-Hydroxy-9H-thioxanthen-1yl)-6-morpholin-4-yl -pyran-4-one ether derivatives (a) To a mixture of 2-(4-hydroxy-9H-thioxanthen-1yl)-6-morpholin-4-yl-pyran-4-one (87)(20 mg, 0.05 mmol) and potassium carbonate (16 mg, 0.11 mmol) in N,N-dimethylformamide (0.5 ml) was added dibromoethane (22 μl, 0.25 mmol). After 4 hours the appropriate amine or thiol (0.254 mmol, 5 eq) was added to the solution, and the compounds isolated are shown below:

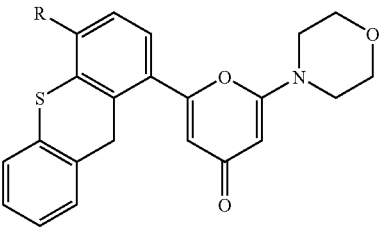
| Compound | R | Purity | Retention Time (Mins) | M+ + 1 |
|---|---|---|---|---|
| 88 | (piperidine-N-CH2CH2-O-*) | 95 | 3.26 | 505 |
| 89 | (piperazine-N-CH2CH2-O-*) | 95 | 3.00 | 506 |
| 90 | (4-methylpiperazine-N-CH2CH2-O-*) | 95 | 3.13 | 520 |
| 91 | (HOCH2CH2)2N-CH2CH2-O-* | 95 | 3.03 | 525 |
| 92 | (MeOCH2CH2)2N-CH2CH2-O-* | 95 | 3.3 | 553 |

-continued
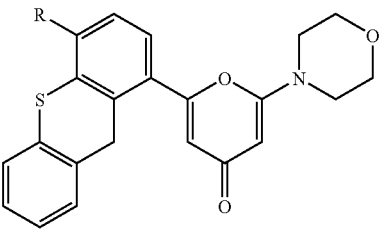
| Compound | R | Purity | Retention Time (Mins) | M+ + 1 |
|---|---|---|---|---|
| 93 | HN-CH2CH2-OH, -O-CH2CH2- | 95 | 3.02 | 481 |
| 94 | HN-CH2CH2-NH2, -O-CH2CH2- | 95 | 2.76 | 480 |
| 95 | HN-CH2-CH(OH)-CH2OH via -O-CH2CH2- | 85 | 3.03 | 511 |
| 96 | pyrrolidinyl-CH2CH2-O-* | 90 | 3.15 | 491 |
| 97 | 4-methyl-1,4-diazepan-1-yl-CH2CH2-O-* | 90 | 2.88 | 534 |

-continued
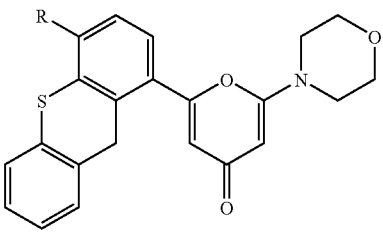
| Compound | R | Purity | Retention Time (Mins) | M+ + 1 |
|---|---|---|---|---|
| 98 | (1,4-diazepan-1-yl)ethoxy | 90 | 2.83 | 520 |
| 99 | (azepan-1-yl)ethoxy | 95 | 3.28 | 519 |
| 100 | (dimethylamino)ethoxy | 95 | 3.08 | 465 |
| 101 | (4-methoxybenzylamino)ethoxy | 95 | 3.38 | 557 |
| 102 | (1,2,4-triazol-3-ylthio)ethoxy | 90 | 3.7 | 521 |

(b) 2-(4-hydroxy-9H-thioxanthen-1yl)-6-morpholin-4-yl-pyran-4-one (87)(20 mg, 0.0508 mmol), potassium carbonate (44 mg, 0.315 mmol) and N,N-dimethylformamide (0.5 ml) was added to 2, 3 or 4-picolyl chloride hydrochloride (0.25 mmol), respectively. The reactions were stirred at room temperature for 2 hours. The crude reaction mixtures were submitted for purification by preparative HPLC without any further workup, and the compounds produced are shown below:

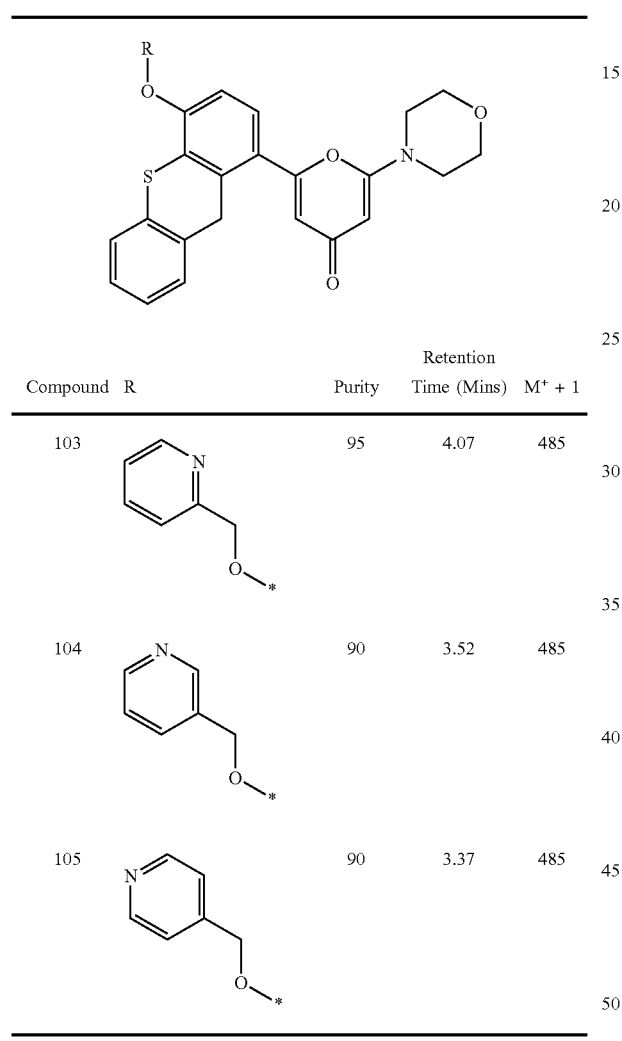

| Compound | R | Purity | Retention Time (Mins) | $M^+ + 1$ |
|---|---|---|---|---|
| 103 | 2-pyridylmethyloxy | 95 | 4.07 | 485 |
| 104 | 3-pyridylmethyloxy | 90 | 3.52 | 485 |
| 105 | 4-pyridylmethyloxy | 90 | 3.37 | 485 |

Example 11

N-Acyl 2-(1-Amino-9H-thioxanthen-4-yl)-6-morpholin-4-yl-pyran-4-one derivatives

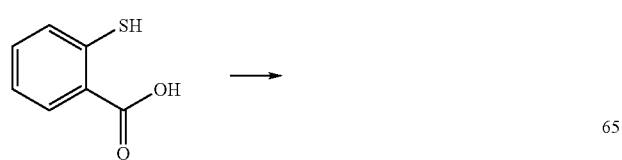

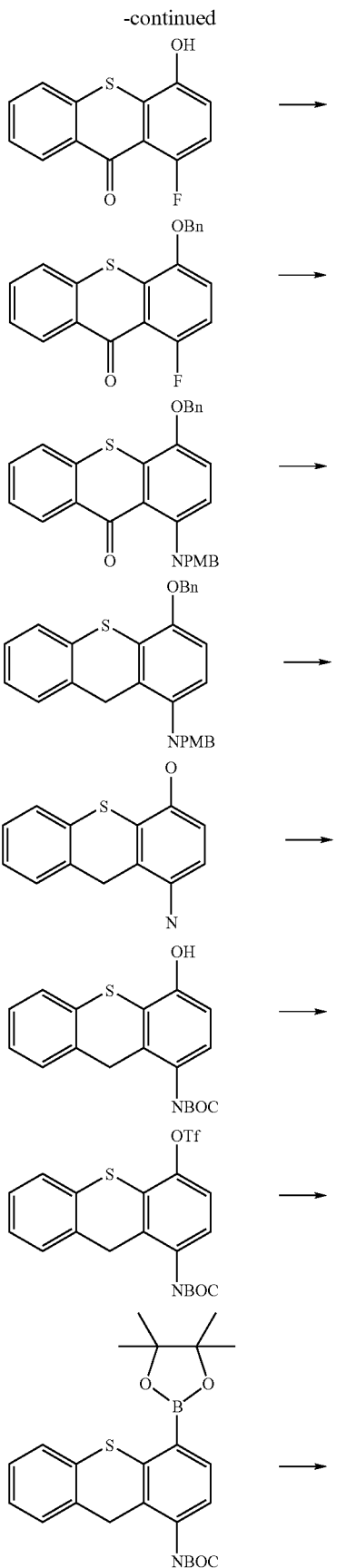

-continued

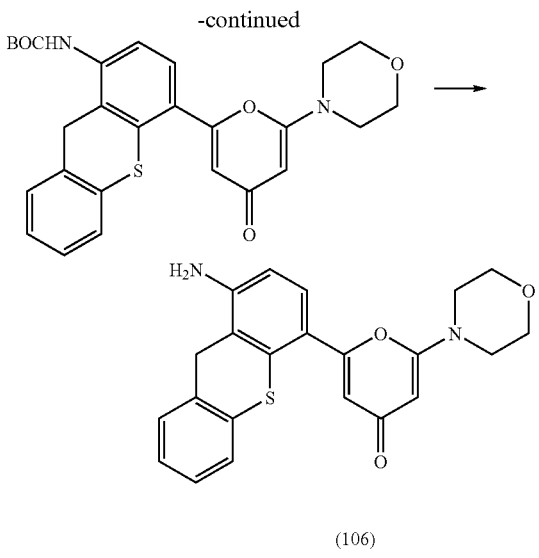

(106)

1-Fluoro-4-hydroxy-thioxanthen-9-one

To a solution of 2-thiosalicylic acid (39.32 g, 255 mmol) in concentrated sulfuric acid (700 ml) was added 4-fluorophenol (32.0 g, 280 mmol). The red solution was then stirred at room temperature for 18 hours. Upon completion, the mixture was poured directly onto 4 liters of crushed ice and the resulting red solid was filtered off, and then suspended in water (1 L)and treated with ammonia solution until pH 6 attained whereupon the precipitate was re-filtered to give the title compound as an orange solid (44.48 g, 70.8%) m/z (LC-MS, ESP): 247 [M+H]$^+$, R/T=3.99 mins

4-Benzyloxy-1-fluoro-thioxanthen-9-one $K_2CO_3$ (21.0 g, 150 mmol) was added to a stirred suspension of 1-Fluoro-4-hydroxy-thioxanthen-9-one (18.47 g, 75.0 mmol) in methanol (100 mL) followed by benzylbromide (16 mL, 75.0 mmol) which was added in slow stream via syringe. The resulting mixture was then heated to reflux for 90 minutes and then cooled to room temperature before it was poured onto crushed ice (0.5 L). The resulting precipitate was filtered off and dried ($P_2O_5$) to give the title compound as a yellow solid (16.7 g, 66.1%) m/z (LC-MS, ESP): 337 [M+H]$^+$, R/T=5.22 mins

4-Benzyloxy-1-(4-methoxy-benzylamino)-thioxanthen-9-one

To a solution of 4-methoxybenzyl amine (1.63 g, 11.89 mmol) in dry pyridine (10 ml) was added 4-Benzyloxy-1-fluoro-thioxanthen-9-one (1 g, 2.97 mmol) in a single portion. The mixture was then heated to reflux (140° C.) for 18 hrs. The resulting hot orange suspension was allowed to cool to room temperature before being poured onto 100 ml of crushed ice. The precipitate was filtered off and washed with copious amounts of water to give the title compound as a red/orange solid (1.35 g, 89.6%). m/z (LC-MS, ESP): 454 [M+H]$^+$ R/T=6.09 mins.

(4-Benzyloxy-9H-thioxanthen-1-yl)-(4-methoxy-benzyl)-amine

To a cooled (0° C.) suspension of 4-benzyloxy-1-(4-methoxy-benzylamino)-thioxanthen-9-one (8.16 g, 18.00 mmol) in dry THF (150 ml) was added Borane-THF complex (90 mmol, 90 ml 1M in THF) in a dropwise fashion. The reaction was allowed to slowly warm to room temperature and stirred for a further 16 hours to give a homogeneous yellow solution. To mixture was then cooled (0° C.) and diluted slowly with acetone (150 ml) and then stirred for 60 minutes at room temperature. The solvent was removed in vacuo to give a crude residue that was diluted in $CH_2Cl_2$ (100 ml) and the washed with a saturated solution of $NaHCO_3$ (100 ml), dried using MgSO4, filtered and concentrated in vacuo to give the title compound as a mild amber oil (7.90 g, 99.8%) m/z (LC-MS, ESP): 438 [M+H]$^+$, R/T=5.01 mins.

1-Amino-9H-thioxanthen-4-ol (4-Benzyloxy-9H-thioxanthen-1-yl)-(4-methoxy-benzyl)-amine (14.51 g, 33.00 mmol) was mixed thoroughly with solid pyridine hydrochloride (190 g, 165.00 mmol) before being heated to 150° C. and stirred at this temperature for a further 12 hours. Upon completion the reaction was cooled slightly before being poured into an beaker of ice/water. The brown precipitate was removed by filtration and the filtrate adjusted to pH 11 with $NH_3OH$ solution before being extracted with $CH_2Cl_2$ (3×100 ml). The combined organic phases were then washed with water (1×100 ml) and brine (1×100 ml) then dried using MgSO4, filtered and concentrated in vacuo to give the title compound as a thick brown oil (7.50 g, 99.1%) m/z (LC-MS, ESP): 229 [M+H]$^+$, R/T=4.15 mins.

(4-Hydroxy-9H-thioxanthen-1-yl)-carbamic acid tert-butyl ester

To a solution of 1-amino-9H-thioxanthen-4-ol (7.57 g, 33.00 mmol) in dry THF (50 ml) was added di-tertiary butyl dicarbonate (20 g, 91.64 mmol) in a single portion. The reaction was stirred at room temperature for 4 hours before the addition of methanol (50 mL) and solid NaOH (10 g, 250 mmol). The resulting slurry was stirred at room temperature for 1 hr before the addition of $H_2O$ (250 ml) and EtOAc (250 ml). The organic extract was removed and the remaining aqueous extracted further with EtOAc (2×50 ml). The combined organics were then dried using MgSO4, filtered and concentrated in vacuo to give the title compound a dark amber oil (10.87 g, 92%) m/z (LC-MS, ESP): 328 [M−H]$^−$, R/T=4.73 mins

Trifluoro-methanesulfonic acid 1-tert-butoxycarbonylamino-9H-thioxanthen-4-yl ester To a cooled (0° C.) solution of (4-Hydroxy-9H-thioxanthen-1-yl)-carbamic acid tert-butyl ester (10.05 g, 30.50 mmol) in dry pyridine (70 ml) was added trifluoromethanesulphonic anhydride (8 ml, 48.77 mmol) in a slow stream via syringe over 10 mins. The brown mixture was stirred at 0° C. for a further 30 mins before the addition of water in a dropwise fashion. The mixture was extracted with EtOAc (3×100 mL), the organic extracts combined, dried using MgSO4, filtered and concentrated in vacuo to give a pale brown oil. Purification of the crude residue was accomplished by flash chromatography (SiO$_2$) using Hexanes: EtOAc (4:1) to give a mild amber oil that was purified by flash chromatography (SiO$_2$) (Hexanes then 3:1-Hexanes: EtOAc) to give a mild amber oil (9.42 g, 67.0%) m/z (LC-MS, ESP): 460 [M–H]$^-$, R/T=5.52 mins.

[4-(4,4,5,5-Tetramethyl-[1,3,2]dioxaborolan-2-yl)-9H-thioxanthen-1-yl]-carbamic acid tert-butyl ester To a solution of Trifluoro-methanesulfonic acid 1-tert-butoxycarbonylamino-9H-thioxanthen-4-yl ester (3.05 g, 6.60 mmol) in dry dioxane (10 ml) was added bis(pinacolato)diboron (2.0 g, 7.92 mmol) and anhydrous potassium acetate (1.9 g, 19.80 mmol). The reaction was then degassed (sonication for 20 min then saturated with N$_2$) before the addition of dichloro[1,1'-bis(diphenylphosphino)ferrocene] palladium(II) dichloromethane adduct (0.26 g). The reaction mixture was degassed for a further 20 minutes before a reflux condenser was attached to the reaction vessel which was then heated to 100° C. and stirred vigorously for 24 hours. The brown reaction mixture was then poured onto a silica pad prepared in hexanes and eluted with CH$_2$Cl$_2$: Hexanes (1:1). The collected eluent was concentrated in vacuo to give crude title compound as a dark brown oil that was used without further purification (2.90 g,).

[4-(6-Morpholin-4-yl-4-oxo-4H-pyran-2-yl)-9H-thioxanthen-1-yl]-carbamic acid tert-butyl ester

[4-(4,4,5,5-Tetramethyl-[1,3,2]dioxaborolan-2-yl)-9H-thioxanthen-1-yl]-carbamic acid tert-butyl ester (2.90 g, 6.50 mmol) was introduced to a solution of 2-Chloro-6-morpholin-4-yl-pyran-4-one (3)(1.4 g, 6.50 mmol) in anhydrous dioxane (6 mL). Powdered K$_2$CO$_3$ (2.01 g, 14.50 mmol) was added and the mixture degassed (sonication for 20 mins then saturated with N$_2$). To the degassed solution was added Tetrakis (triphenylphosphine) palladium (0.39 g) before it was degassed for a further 20 minutes. A reflux condenser was attached to the reaction vessel which was submerged into an oil bath maintained at 100° C. for 14 hours whereupon the golden mixture was cooled and diluted with EtOAc (50 ml) and then washed with water (20 ml) and saturated brine (20 ml). Organic extract was dried using MgSO4, filtered and concentrated in vacuo to give the title compound as a light brown oil that was used without further purification. m/z (LC-MS, ESP): 493 [M+H]$^+$, R/T=4.41 mins.

2-(1-Amino-9H-thioxanthen-4-yl)-6-morpholin-4-yl-pyran-4-one (106)

To a solution of [4-(6-Morpholin-4-yl-4-oxo-4H-pyran-2-yl)-9H-thioxanthen-1-yl]-carbamic acid tert-butyl ester (3.25 g) in CH$_2$Cl$_2$ (25 ml) was added trifluoroacetic acid (5 ml). The mixture was stirred at room temperature for 18 hrs whereupon it was cooled (0° C.) and quenched by dropwise addition of saturated NaHCO$_3$ until the pH 9 was attained. The mixture was then extracted using CH$_2$Cl$_2$ (3×20 mL), the combined organic extracts were then dried (MgSO$_4$), filtered and concentrated in vacuo to give a semi-crystalline solid that was applied onto a thin silica pad and eluted with EtOAc (100%) going to EtOAc:MeOH (9:1). The eluent was concentrated in vacuo to give the title compound as a mild amber oil (1.46 g, 56.4% over three steps) m/z (LC-MS, ESP): 393 [M+H]$^+$, R/T=3.79 mins N-Acyl 2-(1-Amino-9H-thioxanthen-4-yl)-6-morpholin-4-yl-pyran-4-one derivatives (a) To a stirred solution of 2-(1-Amino-9H-thioxanthen-4-yl)-6-morpholin-4-yl-pyran-4-one (106)(39 mg, 0.1 mmol) in anhydrous N,N-dimethylformamide (1 ml), N-ethyldiisopropylamine (0.4 ml, 2.31 mmol) and O-(7-azabenzotriazol-1-yl)-N,N,N',N'-tetramethyluroniumhexafluorophosphate (50 mg, 1.3 mmol) were added. The appropriate carboxylic acid (0.1 mmol) was then added and the mixture stirred at room temperature overnight. The compound was then purified by preparative HPLC to give the desired compounds, which are shown below:

| Compound | R | Purity | M$^+$ + 1 |
|---|---|---|---|
| 107 | (2-furyl) | 95 | 487 |
| 108 | (1-acetyl-piperidin-4-yl) | 95 | 546 |
| 109 | (2-acetoxyphenyl) | 95 | 555 |
| 110 | (2-(pyridin-2-yl)thiophen-5-yl) | 95 | 580 |
| 111 | (4-methyl-1,2,3-thiadiazol-5-yl) | 95 | 519 |
| 112 | (2,1,3-benzothiadiazol-5-yl) | 95 | 555 |

-continued

| Compound | R | Purity | M⁺ + 1 |
|---|---|---|---|
| 113 | 4-NC-C₆H₄- | 95 | 522 |
| 114 | pyridin-4-yl | 95 | 498 |
| 115 | benzo[1,3]dioxol-5-yl | 85 | 541 |
| 116 | MeO-C(O)- | 95 | 479 |
| 117 | 3-(NC)-C₆H₄-NH- | 99 | 537 |
| 118 | MeO-C(O)-CH₂- | 85 | 493 |
| 119 | pyridin-3-yl | 95 | 498 |
| 120 | 2-MeO-C₆H₄- | 95 | 527 |
| 121 | 3,5-(MeO)₂-C₆H₃- | 95 | 557 |

-continued

| Compound | R | Purity | M⁺ + 1 |
|---|---|---|---|
| 122 | 2-(MeS)-pyridin-3-yl | 95 | 544 |
| 123 | 2-methyl-3-acetoxyphenyl | 95 | 569 |
| 124 | MeO-CH₂-C(O)-CH₂- | 95 | 507 |
| 125 | 2,3-dihydro-1,5-benzodioxepin-7-yl | 95 | 569 |
| 126 | isoxazol-5-yl | 95 | 488 |
| 127 | t-BuO- | 95 | 493 |
| 128 | pyrrol-2-yl | 95 | 486 |
| 129 | 3-methylfuran-2-yl | 98 | 501 |

(b) To a solution of 2-(1-amino-9H-thioxanthen-4-yl)-6-morpholin-4-yl-pyran-4-one (106)(25 mg, 0.06 mmol) and pyridine (0.5 mmol) in CH₂Cl₂ (1 mL) was added the appropriate sulfonyl chloride (0.2 mmol) in a single portion. The reaction was stirred at room temperature overnight. The resulting reaction mixture was then purified by preparative HPLC to give the desired compounds, which are shown below:

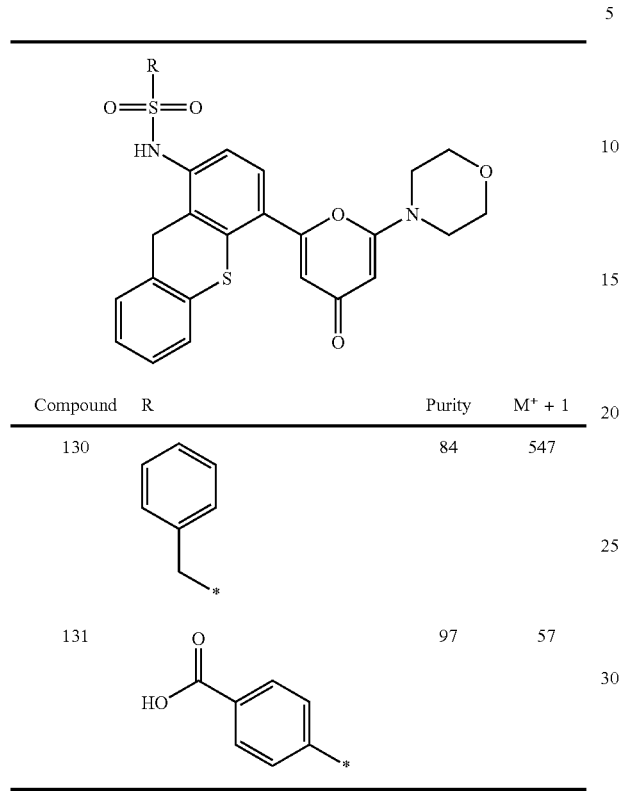

| Compound | R | Purity | M⁺ + 1 |
|---|---|---|---|
| 130 | benzyl | 84 | 547 |
| 131 | 4-carboxyphenyl | 97 | 57 |

Example 12

2-Morpholin-4-yl-6-(11-oxo-10,11-dihydro-dibenzo[b,f]thiepin-4-yl)-pyran-4-one

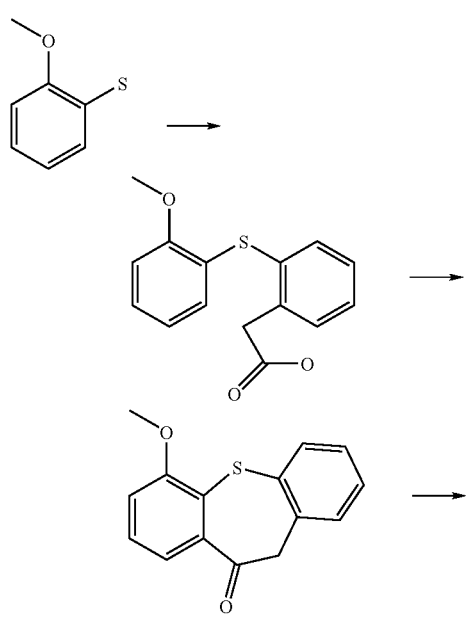

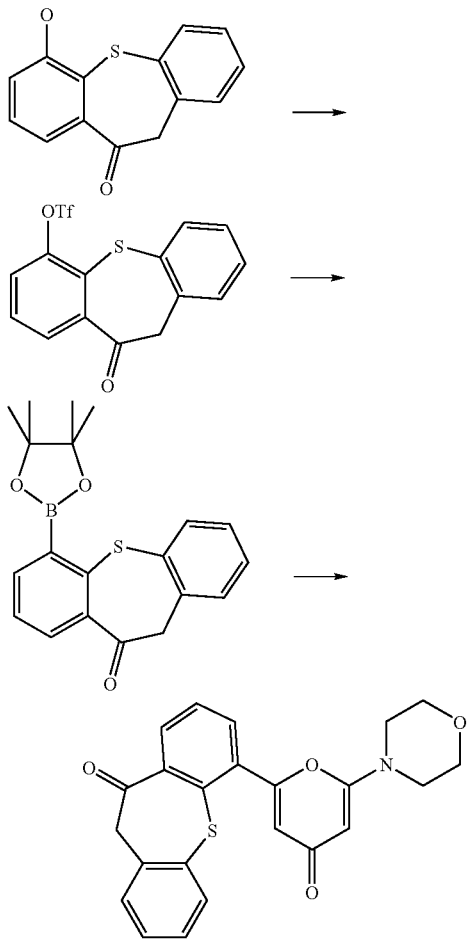

(132)

[2-(2-Methoxy-phenylsulfanyl)-phenyl]-acetic acid

2-Methoxythiophenol (2.8 g, 20 mmol) was added to a solution of potassium hydroxide (4.6 g, 80 mmol) in water (50 ml) and the mixture was degassed for 15 minutes. 2-Iodophenylacetic acid (5.24 g, 20 mmol) and copper bronze (64 mg, 1 mmol) were then added to the reaction mixture, which was refluxed overnight. The solution was cooled down, filtered and the precipitate washed with water (50 ml). The filtrate was acidified with conc HCl (pH 1), extracted with dichloromethane (3×100 ml). The organics were combined, extracted with saturated brine, dried over sodium sulphate and evaporated in vacuo to give the title compound as a pale brown oil which solidified overnight. The compound was used without any further purification (5.10 g, 93%).

6-Methoxy-11H-dibenzo[b,f]thiepin-10-one

[2-(2-Methoxy-phenylsulfanyl)-phenyl]-acetic acid (5.40 g, 20 mmol) was dissolved in methanesulfonic acid (50 ml) and the mixture was heated for 2 hours at 90° C. under stirring and a nitrogen atmosphere. The reaction mixture was cooled to room temperature and poured onto ice with stirring. The black precipitate was filtered and dried over night in a vacuum oven (50° C.). The compound was used without any further purification (4.60 g, 91%).

6-Hydroxy-11H-dibenzo[b,f]thiepin-10-one

6-Methoxy-11H-dibenzo[b,f]thiepin-10-one (1.54 g, 6 mmol) and pyridine hydrochloride (10 g) were heated for 2 hours at 200° C. with stirring and $N_2$ atmosphere. The reaction was cooled down to room temperature and then triturated in water (200 ml) The pale green precipitate was filtered and dried overnight in a vacuum oven (50° C.) (1.40 g, 96%). $^1$HNMR (300 MHz, DMSO-$d_6$): $\delta_H$=4.20 (2H, s), 7.05–7.69 (7H, m), 10.56 (1H, s).

Trifluoro-methanesulfonic acid 11-oxo-10,11-dihydro-dibenzo[b,f]thiepin-4-yl ester 6-Hydroxy-11H-dibenzo[b,f]thiepin-10-one (242 mg, 1 mmol) was dissolved in dry pyridine (5 ml) and trifluoromethanesuphonic anhydride (0.17 ml, 1 mmol) was added drop wise to the stirred solution at 0° C. under $N_2$ atmosphere. The reaction mixture was left to react for 4 hrs and was then poured into water. (50 ml) The organic were extracted with dichloromethane (3×50 ml), washed with 0.2N HCl, dried over magnesium sulphate and evaporated in vaccuo to give a dark brown solid. This solid was purified by column chromatography (dichloromethane/hexane, 3:7, Rf=0.15) to give the title compound as a pale brown solid (0.37 g, 100%). $^1$HNMR (300 MHz, DMSO-$d_6$): $\delta_H$=3.70 (2H, s), 7.31–7.8 (7H, m).

6-(4,4,5,5-Tetramethyl-[1,3,2]dioxaborolan-2-yl)-11H-dibenzo[b,f]thiepin-10-one

Trifluoro-methanesulfonic acid 11-oxo-10,11-dihydro-dibenzo[b,f]thiepin-4-yl ester (0.374 g, 1 mmol), bis(pinacolato)diboron (305 mg, 1.2 mmol) and potassium acetate (294 mg, 3 mmol) were dissolved in 1,4-dioxane (5 mL) and the mixture was degassed for 5 min. Pd(dppf)Cl$_2$ (40 mg, 0.05 mmol) and dppf (28 mg, 0.05 mmol) were added to the vessel, and the reagents heated to 100° C. under nitrogen with stirring for 12 hours. The reaction mixture was purified by flash chromatography (dichloromethane/hexane, 1:4) and the black residue was used without further purification (0.35 g).

2-Morpholin-4-yl-6-(11-oxo-10,11-dihydro-dibenzo [b,f]thiepin-4-yl)-pyran-4-one (132)

2-Chloro-6-morpholin-4-yl-pyran-4-one (3)(215 mg, 1 mmol), 6-(4,4,5,5-Tetramethyl-[1,3,2]dioxaborolan-2-yl)-11H-dibenzo[b,f]thiepin-10-one (352 mg, 1 mmol), and ground potassium carbonate (276 mg, 2 mmol) were suspended in 1,4-dioxane (10 ml) and degassed for 5 minutes. Pd(PPh$_3$)$_4$ (57 mg, 0.05 mmol) was then added and the reaction mixture was then heated at 90° C. for 4hours under a vigorous stirring and a $N_2$ atmosphere. The solvent was removed in vaccuo and the residue was then suspended in water (100 ml). The organics were extracted with dichloromethane (3×100 ml), combined, washed with saturated brine and dried over sodium sulphate. The solvent was removed in vaccuo and the residue was purified by column chromatography (silica; ethyl acetate:ethanol; 9:1) to give the title compound as a pale brown solid (0.12 g, 29%). $^1$HNMR (300 MHz, DMSO-$d_6$): $\delta_H$=3.40 (4H, t), 3.70 (4H, t), 4.43 (2H, s), 5.55 (1H, d), 6.29 (1H, d), 7.25–7.55 (5H, m), 7.78–7.81 (1H, m), 8.20–8.22 (1H, m); m/z (LC-MS, ESP), RT=4.12 min, (M$^+$+1)=406.

Example 13

2-(10,11-Dihydro-dibenzo[b,f]thiepin-4-yl)-6-morpholin-4-yl-pyran-4-one

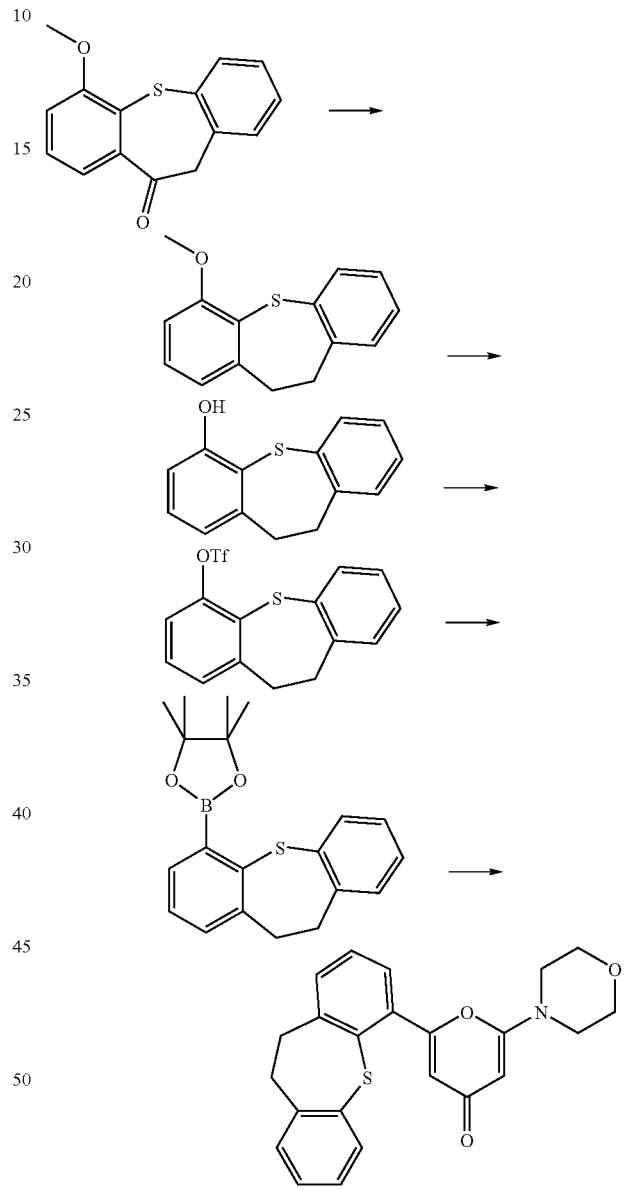

(133)

4-Methoxy-10,11-dihydro-dibenzo[b,f]thiepine

Hydrazine hydrate (4 ml) and potassium hydroxide (2.72 g, 48 mmol) was added to 6-methoxy-11H-dibenzo[b,f] thiepin-10-one (4.10 g, 16 mmol) in ethylene glycol (20 ml) and the reaction mixture was heated at 175° C. for 3 hours. The reaction mixture was cooled down to room temperature and water was added (100 ml). The white solution was extracted with ether (3×200 ml), the organics were combined, washed with water (100 ml), brine (100 ml) and dried over magnesium sulphate. The solvent was removed in vacuo to give an oil which solidify upon standing to give a brown solid which was used without any further purification (2.45 g, 63%).

10,11-Dihydro-dibenzo[b,f]thiepin-4-ol

4-Methoxy-10,11-dihydro-dibenzo[b,f]thiepine (2.42 g, 10 mmol) and pyridine hydrochloride (15 g) were heated with stirring at 180° C. for one hour. Water (100 ml) was added to the reaction mixture and the organics were extracted with ethyl acetate (3×100 ml). The organics were combined and washed with 2N HCl (50 ml), brine (50 ml), and dried over magnesium sulphate. The solvent were removed in vacuo and the residue was purified by column chromatography (1:9; dichloromethane:hexane) to give the desired compound as a white solid (1.55 g, 68%). $^1$HNMR (300 MHz, DMSO-d$_6$): $\delta_H$=3.13–3.23 (4H, m), 6.70 (2H, t), 6.97–7.15 (4H, m), 7.38 (1H,s) 9.78 (1H, s); m/z (LC-MS, ESP), RT=4.59 min, (M$^+$+1)=229.

Trifluoro-methanesulfonic acid 10,11-dihydro-dibenzo[b,f]thiepin-4-yl ester 10,11-Dihydro-dibenzo[b,f]thiepin-4-ol (1.26 g, 5.5 mmol) was dissolved in dry pyridine (5 ml) and trifluoromethanesuphonic anhydride (1.12 ml, 6.6 mmol) was added drop wise to the stirred solution at 0° C. under N$_2$ atmosphere. The reaction mixture was left to react for 4 hrs and was then poured into water. (100 ml) The organic were extracted with dichloromethane (3×50 ml), washed with 0.2N HCl, dried over magnesium sulphate and evaporated in vaccuo to give a dark brown solid. This solid was purified by flash chromatography (dichloromethane) to give an oil (1.1 g, 56%). $^1$HNMR (300 MHz, DMSO-d$_6$): $\delta_H$=3.25–3.29 (2H, m), 3.37–3.41 (2H, m), 7.12–7.17 (1H, m), 7.21–7.31 (3H, m), 7.38–7.41 (3H, s).

2-(10,11-Dihydro-dibenzo[b,f]thiepin-4-yl)-4,4,5,5-tetramethyl-[1,3,2]dioxaborolane Trifluoro-methanesulfonic acid 10,11-dihydro-dibenzo[b,f]thiepin-4-yl ester (1.08 g, 3 mmol), bis(pinacolato)diboron (914 mg, 3.6 mmol) and potassium acetate (883 mg, 9 mmol) were dissolved in 1,4-dioxane (10 mL) and the mixture was degassed for 5 minutes. Pd(dppf)Cl$_2$ (121 mg, 0.15 mmol) and dppf (83 mg, 0.15 mmol) were added to the vessel, and the reagents heated to 100° C. under nitrogen with stirring for 12-hours. The reaction mixture was purified by flash chromatography (dichloromethane) and the black residue was used without further purification (0.87 g).

2-(10,11-Dihydro-dibenzo[b,f]thiepin-4-yl)-6-morpholin-4-yl-pyran-4-one

2-Chloro-6-morpholin-4-yl-pyran-4-one (3)(1.12 g, 5.2 mmol), 2-(10,11-Dihydro-dibenzo[b,f]thiepin-4-yl)-4,4,5,5-tetramethyl-[1,3,2]dioxaborolane (880 mg, 2.6 mmol), and ground potassium carbonate (720 mg, 5.2 mmol) were suspended in 1,4-dioxane (10 ml) and degassed for 5 minutes. bis(tri-t-butylphosphine)palladium (66 mg, 0.13 mmol) was then added and the reaction mixture was then heated at 90° C. for 4 hours under a vigorous stirring and a N$_2$ atmosphere. The solvent was removed in vaccuo and the residue was then suspended in water (100 ml). The organics were extracted with dichloromethane (3×100 ml), combined, washed with saturated brine and dried over sodium sulphate. The solvent was removed in vaccuo and the residue was purified by column chromatography (silica; ethyl acetate:ethanol; 9:1) to give a pale brown solid (50 mg, 5%). $^1$HNMR (300 MHz, DMSO-d$_6$): $\delta_H$=3.24–3.32 (6H, m), 3.44 (2H, t), 3.66 (4H, t), 5.50 (1H, d), 6.10 (1H, d), 7.08–7.51 (7H, m); m/z (LC-MS, ESP), RT=4.48 min, (M$^+$+1)=392.

Example 14

2-Morpholin-4-yl-6-(10H-phenothiazin-4-yl)-pyran-4-one

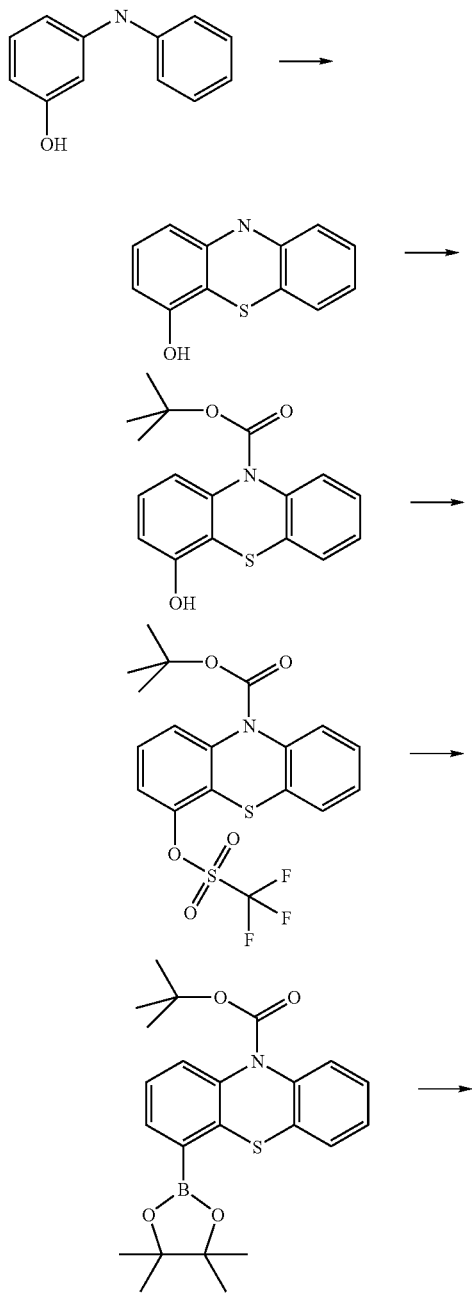

-continued

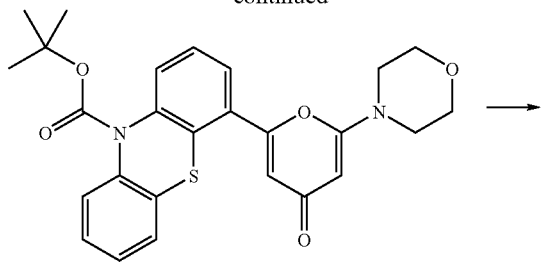

(134)

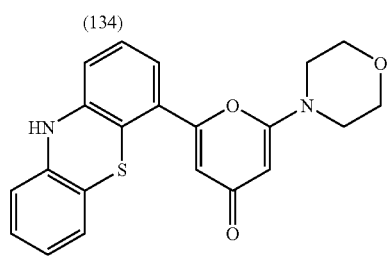

(135)

10H-Phenothiazin-4-ol

To a solution of 3-phenylamino-phenol (5 g, 26.99 mmol) in 1,2-dichlorobenzene (50 ml) was added $S_8$ sulfur(1.82 g, 56.76 mmol) in a single portion and iodine (0.1 g, 0.39 mmol) which was added in three portions over 10 minutes. A reflux condenser was attached to the reaction vessel which was heated to 185° C. under a nitrogen atmosphere. The mixture was stirred at this temperature for 4 hours and then allowed to cool to room temperature. The reaction mixture was filtered to remove a black precipitate and the filtrate diluted with $Et_2O$ (100 ml) and washed with water (2×100 ml). The organic layer was separated and the volatile solvents removed to give a deep green oil that was purified by flash column chromatography ($SiO_2$) (Hexanes then 8:1-Hexanes:EtOAc) to give a pale yellow solid (2.38 g, 40.96%) m/z (LC-MS, ESP) 216 $[M+H]^+$, R/T=4.12 mins.

4-Hydroxy-phenothiazine-10-carboxylic acid tert-butyl ester

To a solution of 10H-Phenothiazin-4-ol (0.77 g, 3.58 mmol) in anhydrous pyridine (10 ml) was added di-tertiary butyl dicarbonate (3.12 g, 14.31 mmol) in a single portion. The solution was heated to 80° C. and stirred under a nitrogen atmosphere for 60 minutes before being allowed to cool to room temperature and treated with water (20 ml) and extracted with EtOAc (2×30 ml). The organic layers were then washed with water (20 ml), dried using $MgSO_4$, filtered and concentrated in vacuo to give an amber oil. The crude residue was treated with MeOH (15 ml) and solid NaOH (0.65 g, 16.25 mmol). The mixture was heated to 80° C. for 60 minutes then cooled to room temperature and neutralised to pH7 with 1M HCl solution. The resulting suspension was then filtered and dried to give the title compound as a beige solid (1.13 g, 100%) that was used without further purification. m/z (LC-MS, ESP): 315 $[M-H]^-$, R/T=4.72 mins.

4-Trifluoromethanesulfonyloxy-phenothiazine-10-carboxylic acid tert-butyl ester

Trifluoromethanesulfonic anhydride (2.95 ml, 17.09 mmol) was added in a dropwise fashion over 10 minutes to a cooled (0° C.) stirred solution of 4-Hydroxy-phenothiazine-10-carboxylic acid tert-butyl ester (3.60 g, 11.41 mmol) in pyridine (40 ml). The reaction mixture was stirred at 0° C. for 1 hour before the addition of water (80 ml). The mixture was extracted using EtOAc (2×60 ml). The organic extracts were then dried using $MgSO_4$, filtered and concentrated in vacuo to give a dark brown oil. The crude residue was then purified by flash chromatography ($SiO_2$) (4:1-Hexanes:EtOAc) to yield a yellow oil (5.02 g, 98.24%) m/z (LC-MS, ESP): 348 $[M+H-BOC]^+$, R/T=5.61 mins 4-(4,4,5,5-Tetramethyl-[1,3,2]dioxaborolan-2-yl)-phenothiazine-10-carboxylic acid tert-butyl ester To a stirred solution of 4-trifluoromethanesulfonyloxy-phenothiazine-10-carboxylic acid tert-butyl ester (3.0 g, 6.7 mmol) in anhydrous dioxane (10 ml) was added bis(pinacolato)diboron (2.05 g, 8.06 mmol) and potassium acetate (1.96 g, 20.01 mmol). The reaction was then degassed (sonication for 20 minutes then saturated with $N_2$) before the addition of dichloro[1,1'-bis(diphenylphosphino)ferrocene] palladium(II) dichloromethane adduct (0.27 g, 0.33 mmol). The reaction mixture was degassed for a further 20 minutes before a reflux condenser was attached to the reaction vessel which was then heated to 90° C. and stirred vigorously for 72 hours. The dark brown reaction mixture was then allowed to cool to room temperature before it was applied to a thick silica pad prepared in hexanes and eluted with hexanes: $CH_2Cl_2$-(2:1). The eluent was concentrated in vacuo to give a dark brown oil (2.85 g, 100%) that was used for the next transformation with no further purification. m/z (LC-MS, ESP): 326 $[M+H-BOC]^+$, R/T=5.86 mins 4-(6-Morpholin-4-yl-4-oxo-4H-pyran-2-yl)-phenothiazine-10-carboxylic acid tert-butyl ester (134)

Powdered potassium carbonate (2.03 g, 14.68 mmol) and 2-Chloro-6-morpholin-4-yl-pyran-4-one (1.44 g, 6.70 mmol) were added to a stirred solution of 4-(4,4,5,5-tetramethyl-[1,3,2]dioxaborolan-2-yl)-phenothiazine-10-carboxylic acid tert-butyl ester (2.85 g, 6.70 mmol) in anhydrous dioxane (20 ml) and the mixture degassed (sonication for 20 minutes then saturated with $N_2$) thoroughly. Tetrakis (triphenylphosphine) palladium was then added in a single portion and the mixture degassed (sonication for 20 minutes then saturated with $N_2$) once again before a reflux condenser was attached and the mixture heated to 100° C. under a nitrogen atmosphere for 20 hours. Water (30 ml) was added and the mixture extracted with EtOAc (3×30 ml). The organic extracts were then dried using $MgSO_4$, filtered and concentrated in vacuo to yield a dark brown, crystalline solid (3.21 g, 100%) that was taken forward with no further purification. m/z (LC-MS, ESP): 479 $[M+H]^+$, R/T=4.55 mins 2-Morpholin-4-yl-6-(10H-phenothiazin-4-yl)-pyran-4-one (135)

To a stirred solution of 4-(6-Morpholin-4-yl-4-oxo-4H-pyran-2-yl)-phenothiazine-10-carboxylic acid tert-butyl ester (3.65 g, 7.63 mmol), in $CH_2Cl_2$ (30 ml) was added trifluoroacetic acid in a single portion. The mixture was stirred at room temperature for 20 hours whereupon the reaction was concentrated in vacuo to give a thick syrup that was basified in a dropwise fashion with saturated NaHCO₃ (40 ml). The dark green mixture was then stirred at room temperature for 18 hours. The mixture was filtered and the filtrant retained, washed with water and dried to give the title compound as a dark green solid (2.89 g, 83.74% over 3 steps) m/z (LC-MS, ESP): 479 [M+H]⁺, R/T=4.05 mins Example 15

4-Morpholin-4-yl-6-thianthren-1-yl-pyran-2-one

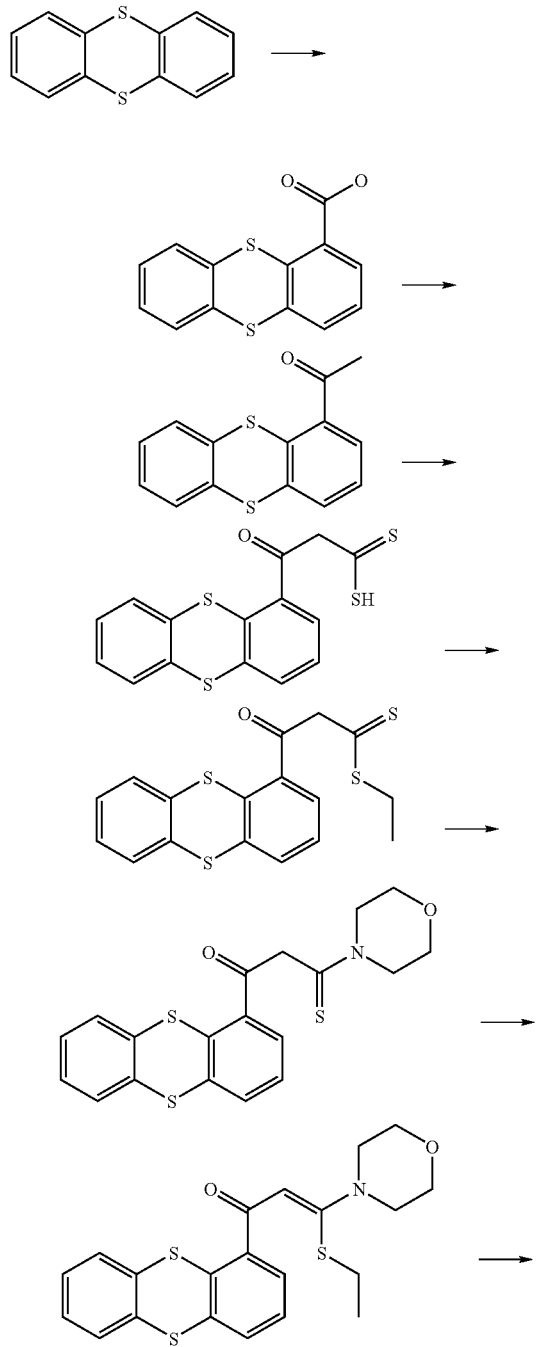

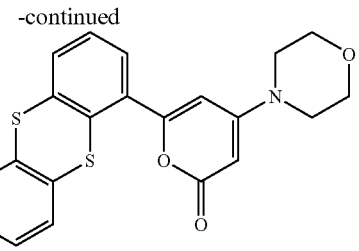

Thianthrene-1-carboxylic acid t-Butyl lithium (1.7M in hexane, 55.1 ml, 93.6 mmol) was added drop wise to a stirred solution of thianthrene (16.9 g, 78 mmol) in dry THF (250 ml) at −78° C. over 30 minutes under an inert atmosphere (N₂). The reaction mixture was allowed to warm to room temperature and the resulting reddish solution was left stirring for 24 hours. The mixture was then cooled down to −78° C. and carbon dioxide (from dry ice pellet and dried by passing over some activated A4 sieves) was bubbled into the solution for 1 hour. The reaction was warmed up back to room temperature with CO₂ still bubbling through it for another hour. Water (10 ml) was then added carefully to the solution and the pH was adjusted to 1 (pH paper) with 2N HCl. The solvent was removed in vacuo and the yellow solid formed was filtered and dried overnight in a vacuum desiccators. The solid was then recrystalised from methanol to give the desired product as a pale yellow crystalline solid (11.9 g, 59%). ¹HNMR (300 MHz, CDCl₃): δ$_H$=7.25 (3H, m); 7.50 (4H, m). m/z (LC-MS, ESP): RT=4.53 min, (M⁻−1)=259

1-Thianthren-1-yl-ethanone

Methyl lithium (1.6M in ether, 57 ml, 90 mmol) was added drop wise to a stirred solution of thianthrene-1-carboxylic acid (11.71 g, 45 mmol) in dry tetrahydrofuran (200 ml) at −78° C. over 30 minutes under an inert atmosphere (N₂). The reaction mixture was allowed to warm to room temperature and (very thick white suspension present) was left stirring for 4 hours. Water (10 ml) was then added carefully to the solution and the pH was adjusted to 1 (pH paper) with 2N HCl. The solvent was removed in vacuo and the yellow solid formed was filtered and dried overnight in a vacuum desiccators. The solid was then purified by column chromatography (ethyl acetate/hexane; 1:9) and was recrystalised from ethanol to give the desired product (6.58 g, 57%). ¹HNMR (300 MHz, CDCl₃): δ$_H$=2.65 (3H, s); 7.26 (3H, m); 7.47 (2H, m); 7.62 (2H, d). m/z (LC-MS, ESP) RT=4.95 min; (M⁺+1)=259

3-Oxo-3-thianthren-1-yl-dithiopropionic acid

A solution of CS₂ (1.55 ml, 25.5 mmol) and 1-thianthren-1-yl-ethanone (6.59 g, 25.5 mmol) in dry tetrahydrofuran (20 ml) was added drop wise to a solution of potassium t-butoxide (5.73 g, 51 mmol) in dry tetrahydrofuran (50 ml) under N₂ at 0° C. A red coloration and the formation of a precipitate were observed. The mixture was left under vigorous stirring over the weekend and was then poured onto water (200 ml) and extracted with ether (3×100 ml). The aqueous was acidified with 2N H₂SO₄ to pH 1 (Whatmann pH paper) and the extracted with ether (3×100 ml).

The organic were dried over magnesium sulphate and the solvent was evaporated in vacuo to give the desired product as a dark orange resin (5.00 g, 59%). m/z (LC-MS, ESP), RT=5.11; (M⁻−1)=333

3-oxo-3-thianthren-1-yl-dithiopropionic acid ethyl ester

Tetrabutylammonium hydrogen sulphate (5.1 g, 15 mmol) and sodium hydroxide (1.2 g, 30 mmol) were dissolved in water (50 ml) A solution of 3-oxo-3-thianthren-1-yl-dithiopropionic acid (5.02 g, 15 mmol) in dichloromethane (50 ml) was added to the solution in one portion and was stirred vigorously for 30 minutes. The aqueous layer was removed and iodoethane (4 ml) was added to the dichloromethane solution that was then stirred for 1 hr. The solvent was removed in vacuo and the residue was taken into water (200 ml) The organics were extracted with ether (3×100 ml), dried over magnesium sulphate and evaporated in vacuo. The residue was then purified by column chromatography (ethyl acetate:hexane; 1:4) to give the desired compound as a bright yellow solid (4.00 g, 73%). ¹HNMR (300 MHz, CDCl₃): $\delta_H$=1.43 (3H, t), 3.33 (3H, q), 6.57 (1H, s), 7.26 (3H, m), 7.51 (3H, m), 7.60 (1H, m), 15.09 (1H, s); m/z (LC-MS, ESP), RT=6.50 min, (M⁻−1)=361.

3-Morpholin-4-yl-1-thianthren-1-yl-3-thioxo-propan-1-one

Morpholine (0.96 ml, 11 mmol) was added to a solution of 3-oxo-3-thianthren-1-yl-dithiopropionic acid ethyl ester (3.99 g, 11 mmol) in ethanol (20 ml). The reaction was refluxed for 8 hours and was then cooled to room temperature. The precipitate formed was filtered and dried to give the desired product as a bright orange solid (3.50 g, 82%). m/z (LC-MS, ESP), RT=4.81 and 5.33 min same (M+1)=388

3-Ethylsulfanyl-3-morpholin-4-yl-1-thianthren-1-yl-propenone

3-Morpholin-4-yl-1-thianthren-1-yl-3-thioxo-propan-1-one (3.49 g, 9 mmol), iodoethane. (0.8 ml, 10 mmol), and grinded potassium carbonate (1.38 g, 10 mmol) were suspended in acetone (20 ml) and the mixture was refluxed for 24 hours. The solvent was removed in vacuo and the residue was taken into water (50 ml). The organics were extracted into dichloromethane (3×100 ml), dried over magnesium sulphate and evaporated in vacuo. The crude product was purified by column chromatography (ethyl acetate/hexane) to give the desired product as a yellow solid (2.26 g, 60%). ¹HNMR (300 MHz, CDCl₃) $\delta_H$=1.34 (3H, t), 2.96 (2H, q), 3.73 (4H, m), 3.84 (4H, m), 7.21 (3H, m), 7.47 (4H, m); m/z (LC-MS, ESP), RT=5.01 min, (M⁺+1)=416.

4-Morpholin-4-yl-6-thianthren-1-yl-pyran-2-one (136)

A suspension of activated zinc dust (0.65 g, 10 mmol), ethyl bromoacetate (0.56 ml, 5 mmol) and a few crystals of iodine in dry tetrahydrofuran (20 ml) were heated at 50° C. for one hour with stirring under a N₂ atmosphere. A solution of 3-ethylsulfanyl-3-morpholin-4-yl-1-thianthren-1-yl-propenone (1.04 g, 2.5 mmol) in dry tetrahydrofuran (20 ml) was added drop wise with stirring and the mixture was refluxed for 12 hours under a N₂ atmosphere. The mixture was then poured over ice cold dilute 3% H₂SO₄ (50 ml), the aqueous layer was extracted with ethyl acetate (3×50 ml), the combined extracts were dried over magnesium sulphate and the solvent was evaporated in vacuo. The residue was purified by column chromatography (ethyl acetate/hexane) to give the desired product (0.35 g, 35%). ¹HNMR (300 MHz, CDCl₃): $\delta_H$=3.45 (4H,t), 3.85 (4H, t), 5.35 (1H, d), 6.29 (1H, d), 7.26 (3H, m), 7.50 (3H, m) 7.61 (1H, m); m/z (LC-MS, ESP), RT=4.50 min, (M⁺+1)=396.

Example 16

6-(6-Morpholin-4-yl-4-oxo-4H-pyran-2-yl)-thianthrene-2-carboxylic acid amide Derivatives

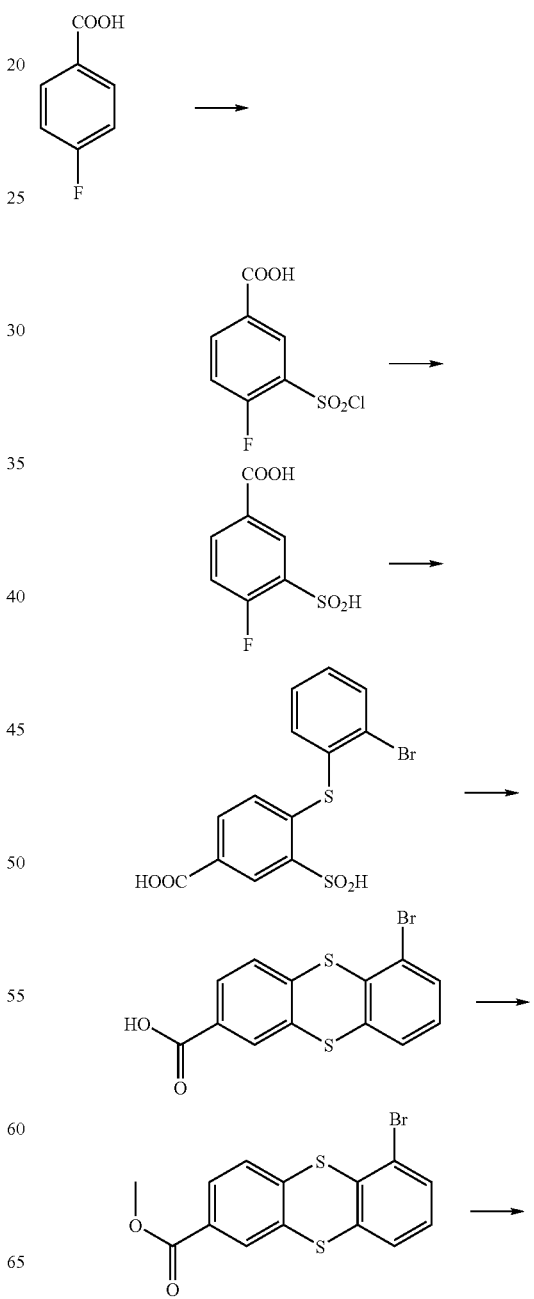

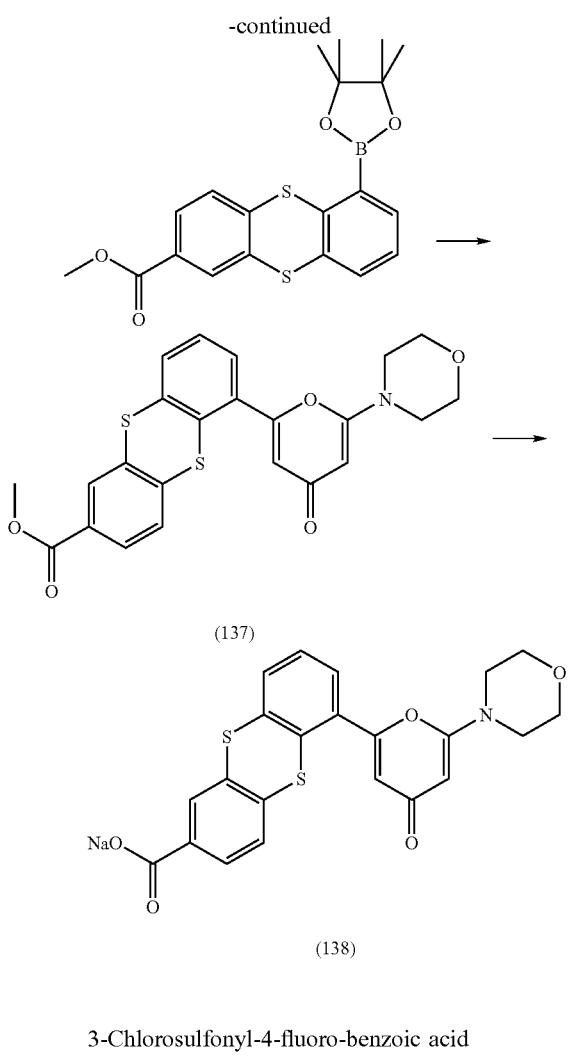

(137)

(138)

3-Chlorosulfonyl-4-fluoro-benzoic acid

Chlorosulphonic acid (100 ml, 1.5 mol) was gradually added to 4-fluorobenzoic acid (43 g, 0.307 mol) with stirring. The clear dark yellow mixture was heated to 150° C. for 24 hours. The yellow solution was cooled back to room temperature and poured onto ice with vigorous stirring. The white precipitate was filtered and pressed dry. The solid was dried overnight in a desiccator under vacuum and over activated silica (54.65 g, 75%). Mp: 116–117° C.; m/z (LC-MS, ESP), RT=4.03 min, (M$^-$-1)=237–239 (ratio 1:3).

4-Fluoro-3-sulfino-benzoic acid

Sodium sulphite (130 g, 1.034 mol) was added slowly to a solution of 3-chlorosulfonyl-4-fluoro-benzoic acid (49.39 g, 0.207 mol) in water (150 ml) at 0° C. with a vigorous stirring. After the addition was completed the reaction was warmed back to room temperature for 1 hour and the pH of the solution was kept around pH 6–7 with 2N sodium hydroxide solution. The white milky suspension was filtered and the solid washed with 2N sodium hydroxide solution (150 ml) and then water (100 ml). The filtrate was then cooled in an ice bath and concentrated HCl was added until no more precipitate was formed (pH<1). The white precipitate was then filtered, pressed dry and left in a dessicator overnight under vacuum and over activated silica (27.92 g, 66%). m/z (LC-MS, ESP), RT=0.98 min, (M$^-$-1)=203

4-(2-Bromo-phenylsulfanyl)-3-sulfino-benzoic acid

2-Bromobenzenethiol (25 g, 132 mmol) was added to a solution of 4-fluoro-3-sulfino-benzoic acid (13.5 g, 66 mmol) and NaOH pellets (11 g, 264 mmol) in water (30 ml). The yellow mixture was then degassed for 10 minutes and then heated to 140° C. for 48 hours. The reaction was then cooled to 0° C. and acidified to pH 4–5 (pH paper) with concentrated HCl. The precipitate formed was filtered, washed with hexane and was dried in a vacuum dessicator over activated silica overnight (20.69 g, 84%). m/z (LC-MS, ESP), RT=3.67 min, (M$^-$-1)=373.

6-Bromo-thianthrene-2-carboxylic acid 4-(2-bromo-phenylsulfanyl)-3-sulfino-benzoic acid (14 g, 38 mmol) was added slowly to a stirred solution of methanesulphonic acid (160 ml). The purple solution was heated to 60° C. for 3 hours. The reaction was cooled down to room temperature and was poured into ice (300 ml) where an off-white precipitate appeared. The solid was filtered and washed with water (100 ml) and then dried in a vacuum dessicator over activated silica (9.48 g, 73%). $^1$HNMR (300 MHz, CDCl$_3$): $\delta_H$=7.29 (1H, t), 7.59 (1H, dd), 7.70 (1H,dd) 7.74 (1H, d), 7.87 (1H, dd), 8.03 (1H, d).m/z (LC-MS, ESP), RT=4.99 min, (M$^-$-1)=339

6-Bromo-thianthrene-2-carboxylic acid methyl ester

To 6-bromo-thianthrene-2-carboxylic acid (9 g, 28 mmol) in methanol (180 ml) was slowly added conc. H$_2$SO$_4$ (5 ml). The milky white suspension was heated to 80° C. until all the solid had gone into solution (2 hrs). The suspension was concentrated in vacuo. Water (100 ml) was added and the organics were then extracted with dichloromethane (3×70 ml), dried over MgSO4 and evaporated in vacuo, yielding to a yellow solid. (4.48 g, 45%). $^1$HNMR (300 MHz, CDCl$_3$): $\delta_H$=3.94 (3H, s); 7.13 (1H, t), 7.44 (1H, dd), 7.54 (1H,dd) 7.61 (1H, d), 7.93 (1H, dd), 8.13 (1H, d).

6-(4,4,5,5-Tetramethyl-[1,3,2]dioxaborolan-2-yl)-thianthrene-2-carboxylic acid methyl ester 6-Bromo-thianthrene-2-carboxylic acid methyl ester (1 g, 2.8 mmol), bis(pinacolato)diboron (0.86 g, 3.4 mmol) and potassium acetate (0.12 g, 0.14 mmol) in 1,4-dioxane (15 ml) was degassed for 15 minutes. To the yellow suspension was then added PdCl$_2$(dppf) (78 mg, 0.14 mmol) and dppf (0.83 g, 8.5 mmol). The dark red mixture was heated to 90° C. under a N$_2$ atmosphere for 48 hours. The crude mixture was purified by flash chromatography (dichloromethane) to give viscous brown oil (1.13 g), which was used without any further purification.

6-(6-Morpholin-4-yl-4-oxo-4H-pyran-2-yl)-thianthrene-2-carboxylic acid methyl ester (137)

6-(4,4,5,5-Tetramethyl-[1,3,2]dioxaborolan-2-yl)-thianthrene-2-carboxylic acid methyl ester (1.1 g, 2.83 mmol), 2-chloro-6-morpholin-4-yl-pyran-4-one (0.73 g, 3.4 mmol) and K$_2$CO$_3$ (0.8 g, 5.66 mmol) were dissolved in dry 1,4-dioxane (7 ml). The mixture was degassed for 15 mins and Pd(PPh$_3$)$_4$ (0.16 g, 5 mol %) was then added The dark brown mixture was heated to 90° C. under an atmosphere of N$_2$ for 24 hour. The reaction mixture was concentrated in vacuo and water (100 ml) was added. The brown solid was filtered and washed with water (1.23 g, 96%). m/z (LC-MS, ESP), RT=4.49 min, (M⁺+1)=454.

6-(6-Morpholin-4-yl-4-oxo-4H-pyran-2-yl)-thianthrene-2-carboxylate sodium salt (138)

6-(6-Morpholin-4-yl-4-oxo-4H-pyran-2-yl)-thianthrene-2-carboxylic acid methyl ester (1.1 g, 2.43 mmol) and NaOH Pellets (97 mg, 2.43 mmol) were dissolved in methanol (40 ml). The brown suspension was heated to 80° C. under $N_2$ for 24 hours. The solvent was removed in vacuo and the residue was triturated with diethyl ether. The product was collected by filtration as a fine dark brown powder (1.11 g, 99%). m/z (LC-MS, ESP), RT=3.90 min, (M⁻−1)=438

6-(6-Morpholin-4-yl-4-oxo-4H-pyran-2-yl)-thianthrene-2-carboxylic acid amide Derivatives 6-(6-morpholin-4-yl-4-oxo-4H-pyran-2-yl)-thianthrene-2-carboxylate sodium salt (138)(20 mg, 0.04 mmol), HBTU (18 mg, 0.05 mmol), di-isopropylethylamine (9 μl, 0.05 mmol), the appropriate amine (0.04 mmol) and dry dimethylacetamide (0.5 ml). The dark brown mixture was stirred at room temp for 2 hours and then purified by preparative HPLC to give the desired products, which are shown below:

| Compound | R | Purity | Retention Time (Mins) | M⁺ + 1 |
|---|---|---|---|---|
| 139 | methylamino | 95 | 3.65 | 453 |
| 140 | dimethylamino | 95 | 3.7 | 467 |
| 141 | diethylamino | 95 | 4.11 | 495 |
| 142 | ethylamino | 95 | 3.78 | 467 |
| 143 | n-butylamino | 95 | 4.28 | 495 |
| 144 | n-propylamino | 95 | 4.03 | 481 |
| 145 | isobutylamino | 90 | 4.22 | 495 |
| 146 | isopropylamino | 95 | 4.01 | 481 |
| 147 | NC-CH₂-CH₂-NH- | 85 | 3.84 | 477 |
| 148 | F₃C-CH₂-CH₂-NH- | 90 | 4.1 | 521 |

-continued
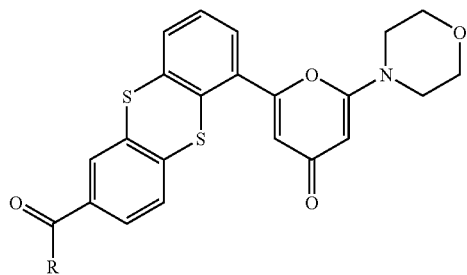
| Compound | R | Purity | Retention Time (Mins) | M+ + 1 |
|---|---|---|---|---|
| 149 | tetrahydrofuran-2-ylmethyl-NH-* | 90 | 3.81 | 523 |
| 150 | furan-2-ylmethyl-NH-* | 95 | 4.1 | 519 |
| 151 | cyclohexyl-NH-* | 95 | 4.54 | 521 |
| 152 | cyclopropylmethyl-NH-* | 95 | 4.1 | 493 |
| 153 | cyclobutyl-NH-* | 95 | 4.12 | 493 |
| 154 | cyclohexylmethyl-NH-* | 95 | 4.77 | 535 |
| 155 | cyclopentyl-NH-* | 95 | 4.3 | 507 |
| 156 | pyrrolidin-1-yl-* | 95 | 3.89 | 493 |
| 157 | piperidin-1-yl-* | 95 | 4.14 | 507 |
| 158 | 2,6-dimethylmorpholin-4-yl-* | 95 | 4.00 | 537 |

-continued
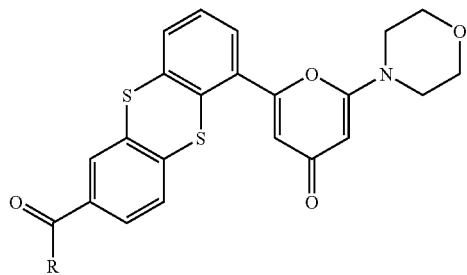
| Compound | R | Purity | Retention Time (Mins) | M⁺ + 1 |
|---|---|---|---|---|
| 159 | (2,6-dimethylmorpholinyl) | 95 | 4.02 | 537 |
| 160 | (morpholinyl) | 95 | 3.69 | 509 |
| 161 | (azepanyl) | 95 | 4.31 | 521 |
| 162 | (benzoyl hydrazide) | 95 | 3.73 | 558 |
| 163 | (2-(methoxymethyl)pyrrolidin-1-yl amino) | 95 | 3.72 | 552 |
| 164 | (4-methylpiperazin-1-yl amino) | 95 | 3.12 | 537 |
| 165 | (morpholin-4-yl amino) | 95 | 3.49 | 524 |
| 166 | (2-(piperidin-1-yl)ethylamino) | 95 | 3.29 | 550 |

-continued
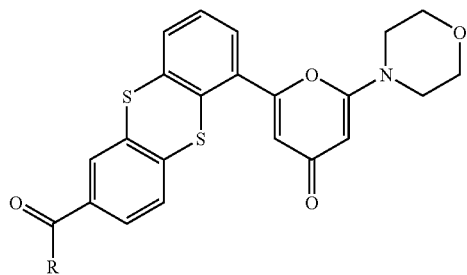
| Compound | R | Purity | Retention Time (Mins) | M+ + 1 |
|---|---|---|---|---|
| 167 | (2-pyrrolidin-1-ylethyl)amino | 95 | 3.23 | 536 |
| 168 | (2-(1-methylpyrrolidin-2-yl)ethyl)amino | 95 | 3.22 | 550 |
| 169 | (4-(dimethylamino)benzyl)amino | 95 | 3.62 | 572 |
| 170 | (pyridin-2-ylmethyl)amino | 95 | 3.43 | 530 |
| 171 | (pyridin-3-ylmethyl)amino | 95 | 3.27 | 530 |
| 172 | (pyridin-4-ylmethyl)amino | 95 | 3.21 | 530 |

-continued
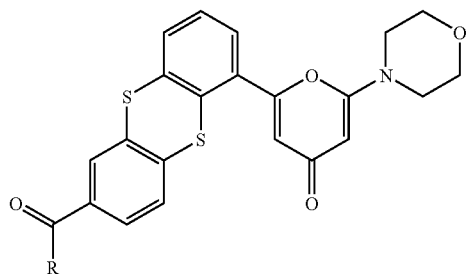
| Compound | R | Purity | Retention Time (Mins) | M+ + 1 |
|---|---|---|---|---|
| 173 | 2-(pyridin-2-yl)ethyl-NH-* | 95 | 3.26 | 544 |
| 174 | N-methyl-N-[2-(pyridin-2-yl)ethyl]-* | 95 | 3.3 | 558 |
| 175 | 2-(4-methylpiperazin-1-yl)ethyl-NH-* | 95 | 3.05 | 579 |
| 176 | 2-(1H-imidazol-4-yl)ethyl-NH-* | 95 | 3.17 | 533 |
| 177 | 2-(morpholin-4-yl)ethyl-NH-* | 95 | 3.19 | 552 |
| 178 | 3-(morpholin-4-yl)propyl-NH-* | 95 | 3.18 | 566 |
| 179 | 2-(4-benzylpiperazin-1-yl)ethyl-NH-* | 95 | 3.44 | 641 |
| 180 | 2-(4-tert-butoxycarbonylpiperazin-1-yl)ethyl-NH-* | 95 | 3.49 | 651 |
| 181 | 2-(diethylamino)ethyl-NH-* | 95 | 3.29 | 538 |

-continued

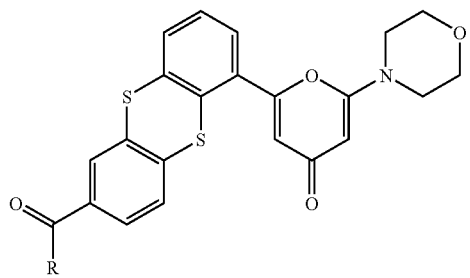

| Compound | R | Purity | Retention Time (Mins) | M⁺ + 1 |
|---|---|---|---|---|
| 182 | (diethylaminopropylamino group) | 95 | 3.27 | 552 |

B) Biological Examples

Materials and Methods

In vitro ATM inhibition Assays

In order to assess the inhibitory action of the compounds against ATM in vitro, the following assay was used to determine $IC_{50}$ values.

ATM protein was immunoprecipitated from HeLa cell nuclear extract using rabbit polyclonal anti-sera raised to the C-terminal ~500 amino-acid residues of the human ATM protein. The immunoprecipitation was performed according to the methodology described by Banin, S. et al. (1998). 10 µl of immunoprecipitated ATM in Buffer C (50 mM Hepes, pH 7.4, 6 mM $MgCl_2$, 150 mM NaCl, 0.1 mM sodium orthovanadate, 4 mM MnCl2, 0.1 mM dithiothreitol, 10% glycerol) was added to 32.5 µl of buffer C containing 1 µg of the ATM substrate GSTp53N66 in a V-bottomed 96 well polypropylene plate. The GSTp53N66 substrate is the amino terminal 66 amino acid residues of human wild type p53 fused to glutathione S-transferase. ATM phosphorylates p53 on the residue serine 15 (Banin, S. et al. (1998)). Varying concentrations of inhibitor were then added. All compounds were diluted in DMSO to give a final assay concentration of between 100 µM and 1 nM, with DMSO being at a final concentration of 1%. After 10 minutes of incubation at 37° C., the reactions were initiated by the addition of 5 µl of 500 µM Na-ATP. After 1 hour with shaking at 37° C., 150 µl of phosphate buffered saline (PBS) was added to the reaction and the plate centrifuged at 1500 rpm for 10 minutes. 5 µl of the reaction was then transferred to a 96 well opaque white plate containing 45 µl of PBS to allow the GSTp53N66 substrate to bind to the plate wells. The plate was covered and incubated at room temperature for 1 hour with shaking before discarding the contents. The plate wells were washed twice by the addition of PBS prior to the addition of 3% (w/v) bovine serum albumin (BSA) in PBS. The plate was incubated at room temperature for 1 hour with shaking before discarding the contents and washing twice with PBS. To the wells, 50 µl of a 1:10,000 dilution of primary phosphoserine-15 antibody (Cell Signaling Technology, #9284L) in 3% BSA/PBS was added to detect the phosphorylation event on the serine 15 residue of p53 elicited by the ATM kinase. After 1 hour of incubation at room temperature with shaking, the wells were washed four times with PBS prior to the addition of an anti-rabbit HRP conjugated secondary antibody (Pierce, 31462) with shaking for 1 hour at room temperature. The wells were then washed four times with PBS before the addition of chemiluminescence reagent (NEN Renaissance, NEL105). The plate was then shaken briefly, covered with a transparent plate seal and transferred to a TopCount NXT for chemiluminescent counting. Counts per second, following a one second counting time, were recorded for each reaction.

The enzyme activity for each compound is then calculated using the following equation:

$$\% \text{ Inhibition} = 100 - \left( \frac{(cpm \text{ of unknown} - \text{mean negative } cpm) \times 100}{(\text{mean positive } cpm - \text{mean negative } cpm)} \right)$$

Sensitisation of Cells to Ionising Radiation or DNA Double Strand Break Chemotherapies To test the efficacy of the ATM inhibitor compound 4 on its ability to sensitise cells to ionising radiation or to DNA double strand break inducing chemotherapeutics, clonogenic survival assays were performed using the HeLa or LoVo human tumour derived cell lines. The HeLa line was used for ionising radiation studies while LoVo was used for studies with chemotherapeutic agents. Enough cells to give ~100 colonies per treatment were seeded into 6 well dishes 4–6 hours prior to the addition of compound 4 at the concentrations shown on the graphs. After 1 hour, a concentration range of either etoposide (FIG. 2), camptothecin (FIG. 3) or doxorubicin (FIG. 4) was added. For ionising radiation treatment (FIG. 1), after 1 hour of incubation with compound 4, cells were irradiated at 1 Gy/min using a Faxitron 43855D X-ray cabinet. For all treatments, after a further 16 hours incubation, drug containing media was removed and fresh media added prior to a further incubation of 10 days before the staining of colonies with Giemsa. All compounds were solubilised in DMSO, with a final concentration on cells of no more than 0.1%. Resulting colonies containing >50 cells were counted as positives.

Recombinant Retroviral Vectors and Virus Preparation.

The Ψ⁻/LTR⁻/Vpr⁻ replication deficient HIV-1 gag/pol expressing packaging constructs were designed based on the vector LΔP2GPH (Haselhorst et al., 1998 Development of cell lines stably expressing human immunodeficiency virus type 1 proteins for studies in encapsidation and gene transfer. *J Gen Virol*, 79, 231–7.). A HIV-1 integrase mutant packaging construct, which codes for a D64V amino acid change in the integrase gene, was made by site directed mutagenesis (Quikchange mutagenesis system, Stratagene). The HIV-1 luciferase transfer vector, HIV-Luc, was constructed by inserting the firefly luciferase gene in-between two HIV-1 LTR sequences and a Ψ HIV-1 RNA packaging signal sequence. The VSV G envelope expression plasmid has been described previously (Naldini et al., (1996) In vivo gene delivery and stable transduction of nondividing cells by a lentiviral vector. *Science*, 272, 263–7). HIV-1 recombinant retroviral stocks were produced using a modification of the three-plasmid expression system described by Naldini et al., 1996. $6 \times 10^6$ human kidney 293T cells were co-transfected with 10 μg packaging construct WT or integrase D64V mutant, 8 μg HIV-Luc transfer vector and 5 μg VSV G envelope protein expression plasmids using Lipofectamine-2000 reagent (Gibco-BRL). 48 hours post transfection retrovirus-containing cell culture supernatants were harvested, filtered through 0.45 μM cellulose acetate membranes and stored at −80° C. Recombinant HIV-1 viral titres were estimated using the HIV-1 p24 gag antigen ELISA kit from Beckman-Coulter, according to the manufacturers' instructions.

Retroviral Transductions (LUCIA).

For the HIV-1 based luciferase assays (LUCIA), Jurkat T-cells (suspension cultures) were transduced with HIV-Luc recombinant virus containing supernants at an MOI of 0.5 in the presence of 8 μg/ml polybrene at 37° C. for 1 hour. Cells were washed and then plated in multiple wells ($3 \times 10^4$ cells/well) of a 96-well opaque-white tissue culture plate (Corning) containing different concentrations of inhibitors. For HeLa cells (adherent cells) were plated and allowed to attach for 24 hours before exposure to virus containing supernatants. Cells were incubated at 37° C. for 48 hours post virus addition and Luciferase activity was quantified on a Packard TopCount-NXT microplate scintillation counter using Bright-Glo luciferase assay reagent (Promega Corp.). The standard error (S.E.) given for all quantified transduction experiments is calculated from at least three independent experiments. Cytotoxicity was evaluated in parallel with LUCIA (but without virus) using the commercially available CellTiter-96 AQ$_{ueous}$ one solution cell proliferation assay (Promega Corp.), according to the manufacturers' instructions.

HIV-1 4-day Replication Assays

C8166 T-cells were washed and infected with HIV-1 (strains HXB2$_{wt}$ and HXB2$_{AZTres}$, RT amino acid changes 67N, 70R, 215F, 219Q) at low multiplicity of infection for one hour at room temperature. The cells were then washed and distributed ($5 \times 10^4$ cells/well) in triplicate into the wells of 96-well cell culture plates containing different concentrations of inhibitors. The plates were then incubated at 37° C. for 4 days. The cell-free culture fluid was then harvested and assayed for levels of p24 viral antigen using a commercially available ELISA kit (Murex), according to the manufacturers' instructions. Cytotoxicity was evaluated by distributing ($5 \times 10^4$ cells/well) uninfected C8166 T-cells into triplicate wells of 96-well cell culture plates containing different concentrations of inhibitor and incubating the plates at 37° C. After 4 days, 25 μl of XTT, which is metabolised by viable but not dead cells was added and the plates incubated for a further 3 hours at 37° C. Finally, the absorbance was read at a wavelength of 450 nm.

Results

In vitro ATM Assays

Compounds were assayed for ATM inhibition activity using the method described above. Some results are detailed below in Table 1 as IC$_{50}$ values (the concentration at which 50% of the enzyme activity is inhibited). These are determined over a range of different concentrations, normally from 100 μM down to 1 nM. Such IC$_{50}$ values are used as comparative values to identify increased compound potencies.

TABLE 1

| Compound | IC$_{50}$ - ATM |
| --- | --- |
| 4 | <200 nM |
| 5 | <200 nM |
| 6 | <2 μM |
| 7 | <200 nM |
| 9 | <20 μM |
| 13 | <20 μM |
| 17 | <200 nM |
| 18 | <200 nM |

The following compounds had IC$_{50}$ values of less than 200 nM: 19–43, 44–87, 93, 102, 106–107, 109–113, 115–117, 119, 122–124, 126–131, 133–135, 137–140, 142–182.

The following compounds had IC$_{50}$ values of less than 2 μM, in addition to those listed above: 88–92, 94–101, 103–105, 108, 114, 118, 120–121, 125, 132, 136 and 141.

Sensitisation of Cells to Ionising Radiation or DNA Double Strand Break Chemotherapies The data shown in FIGS. 1–4 clearly show that inhibiting ATM with compound 4 has a significant effect on sensitising tumour derived cell lines to DNA double strand break inducing agents.

Retroviral Transductions (LUCIA)

Compound 4 (known as Ku0064) was tested for its ability to repress retroviral infections using HIV-1 based LUCIA (FIG. 5).

It was found to efficiently inhibit HIV-1 LUCIA at low micromolar concentrations in Jurkat T-cells (FIG. 5) as well as all other ATM proficient cell lines tested. The 50% inhibitory concentration (IC$_{50}$) for Compound 4 in LUCIA was around 1–2 μM in Jurkat cells (FIG. 5) and in the range of 1 to 10 μM for all other cell lines tested.

Compound 4 was also tested for cytotoxic and growth inhibition effects in parallel to LUCIA to ensure that this was not the reason for the observed reduction in transduction efficiency. At concentrations up to 10 μM, compound 4 exposure showed no significant cytotoxic effects on Jurkat cells during the course of the assay (FIG. 5).

HIV-1 based LUCIA was performed on HeLa cells in the presence of increasing concentrations of both compound 4 and the nucleoside analog reverse transcriptase inhibitor, 3'-azido-3'-deoxythymidine (AZT).

FIG. 7 shows that the combination of compound 4 and AZT was found to act more effectively in inhibiting HIV-1 infection than either drug alone. FIG. 7 provides an example in which increasing concentrations of AZT was found to enhance the effectiveness of a compound of the present invention in inhibiting HIV-1 infections.

HIV Replication Inhibition

A replication competent HIV-1 strain ($HIV_{HXB2}$) was used to infect C8166 T-cells in the absence or presence of increasing concentrations of compound 4 (FIG. 8), in order to demonstrate the effectiveness of compounds of the present invention in a system where HIV replication occurs. After 4-days of virus replication, the amount of HIV-1 in cell culture supernatants was quantified by p24 antigen ELISA. As a control, the RT inhibitor AZT was used in parallel experiments. FIG. 8A shows the inhibition of HIV-1 replication of a wild type HIV-1 strain ($HIV_{HXB2}$ wt) by compound 4 and AZT. The $IC_{50}$ concentration of Compound 4 for HIV-1 replication inhibition was 0.1 μM. AZT showed an $IC_{50}$ of 0.002 μM.

4-day replication assays were performed using an AZT drug resistant strain of HIV-1 ($HIV_{HXB2}$ AZTres) in the absence or presence of increasing concentrations of compound 4 (FIG. 8B, Table 2). The $IC_{50}$ concentration of Compound 4 for HIV-1 replication inhibition on the AZT resistant strain was 0.06 μM. AZT showed an $IC_{50}$ of 0.05 μM (Table 2), thereby demonstrating a 25-fold resistance to AZT when compared to the wild type strain.

Compound 4 inhibited HIV-1 replication equally well on wild-type HIV-1 ($IC_{50}$=0.1 μM; FIG. 8A, Table 2) as on the AZT resistant HIV-1 strain ($IC_{50}$=0.06 μM; FIG. 8B, Table 2). These data provide evidence that compounds of the present invention may be effective in both the treatment of wild-type and acquired AZT resistant HIV-1 infections and, by implication, HIV-1 strains resistant to other drugs that target viral proteins.

Compound 4 was also tested for cytotoxic and growth inhibition effects on C8166 cells in parallel to the HIV-1 replication assays to ensure that this was not the reason for the observed effects of viral titre (FIG. 8C). Exposure of C8166 cells to Compound 4 showed no significant cytotoxic effects during the course of the assay or over the effective concentration range (less than 1 μM) shown to inhibit HIV-1 replication. The 50% cytotoxic concentration ($CC_{50}$) of compound 4 on C8166 cells was estimated to be greater than 20 μM. Table 2 summarises the experiments showing the anti-HIV-1 activity of Compound 4 in 4-day replication assays. Interestingly, the $IC_{50}$ in LUCIA (1 μM; FIG. 5) was observed to be 10-fold higher than in the replication assays (0.1 μM; FIG. 8A). This difference can be explained by the fact that in replication assays multiple rounds of infection occur and each round provides the potential for HIV-1 inhibition. Therefore, the inhibitory effect of Compound 4 becomes compounded in HIV-1 replication assays. The estimated $IC_{50}$ concentrations in replication assays may therefore represent a more accurate reflection of the extent of inhibition that may be seen in HIV-1 infected patients.

TABLE 2

| Compound | HIV-1 HXB2 ($IC_{50}$ μM) Wild type | HIV-1 HXB2 ($IC_{50}$ μM) AZT resistant |
| --- | --- | --- |
| Compound 4 | 0.1 | 0.06 |
| AZT | 0.002 | 0.05 (25 fold resistant) |

What is claimed is:

1. A compound of formula I:

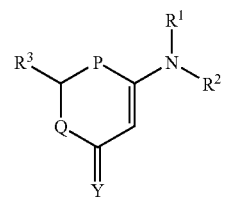

(I)

and isomers, salts, solvates, chemically protected forms, and prodrugs thereof; wherein:
one of P and Q is O, and the other of P and Q is CH, where there is a double bond between whichever of Q and P is CH and the carbon atom bearing the $R^3$ group;
Y is either O or S;
$R^1$ and $R^2$ together form, along with the nitrogen atom to which they are attached, a morpholino group;
$R^3$ is a first phenyl group, attached by a first bridge group selected from —S—, —S(=O)—, —S(=O)$_2$—, —O— and $CR^{C1}R^{C2}$—, to an optionally substituted second phenyl group;
the first phenyl group and the second phenyl group being optionally further linked by a second bridge group selected from —S—, —S(=O)—, —S(=O)$_2$—, —O—, $CR^{C1}R^{C2}$—, —$CR^{C1}R^{C2}CR^{C1}R^{C2}$—, —C=O, —$CR^{C1}R^{C2}$S—, —$CR^{C1}R^{C2}$O—, —$SCR^{C1}R^{C2}$—, —$OCR^{C1}R^{C2}$—, —RC=CR—, or a single bond, which is bound adjacent the first bridge group on both groups so as to form an optionally substituted $C_{5-7}$ ring fused to both the first phenyl group and the second phenyl group, the first phenyl group being further optionally substituted;
$R^{C1}$ and $R^{C2}$ are independently selected from hydrogen, an optionally substituted $C_{1-7}$ alkyl group and an optionally substituted $C_{5-20}$ aryl group;
wherein the first phenyl group in $R^3$ optionally bears a substituent selected from the group consisting of an amino group, a hydroxy group, a halo group, an acylamido group, a sulfonamino group, an alkoxy group, an acylkoxy group, an alkyl group, a nitro group, a cyano group, a thiol group, an alkylthio group, and an acyl group; and
wherein the second phenyl group in $R^3$ optionally bears a substitutent selected from the group consisting of an acylamido group, an ester group, an amido group, an amino group, an acyl group, a sulfonamino group, an ether group, and a carboxy group.

2. A compound according to claim 1, of formula Ia:

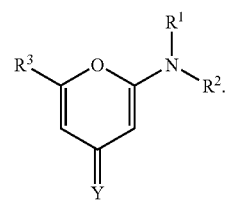

(Ia)

3. A compound according to claim 1, wherein Y is O.

4. compound according to claim 1, wherein $R^3$ is selected from the following optionally substituted groups

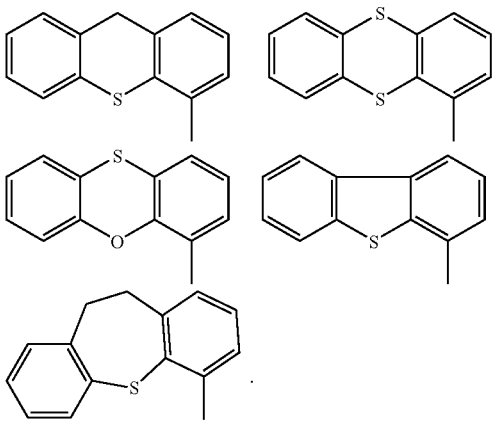

5. A composition comprising a compound according to claim 1 or a pharmaceutically acceptable salt thereof and a pharmaceutically acceptable carrier or diluent.

6. A compound of formula:

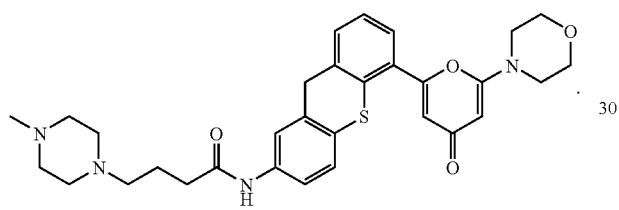

7. A compound according to claim 1 wherein the acylamido has an acyl substituent which is formula (III):

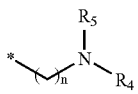

wherein n is 1 to 4, and $R_5$ and $R_4$ independently represent hydrogen, and optionally substituted $C_{1-7}$ alkyl, or $C_{5-20}$ aryl, or may together form, along with the nitrogen atom to which they are attached, an optionally substituted hetrocyclic piperazine, piperidine, or pyrrolidine.

8. A compound of formula I:

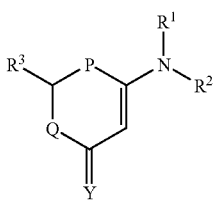

and isomers, salts, solvates, chemically protected forms, and prodrugs thereof wherein:
one of P and Q is O, and the other of P and Q is CH, where there is a double bond between whichever of Q and P is CH and the carbon atom bearing the $R^3$ group;
Y is either O or S;
$R^1$ and $R^2$ together form, along with the nitrogen atom to which they are attached, form a morpholino group;
$R^3$ is a first phenyl group, attached by a first bridge group selected from —S—, —S(=O)—, —S(=O)$_2$—, —O—, or —CR$^{C1}$R$^{C2}$— to an optionally substituted second phenyl group;
the first phenyl group and second phenyl group being optionally further linked by a second bridge group selected from —S—, —S(=O)—, —S(=O)$_2$—, —O—, CR$^{C1}$R$^{C2}$—, —CR$^{C1}$R$^{C2}$CR$^{C1}$R$^{C2}$—, —C=O, —CR$^{C1}$R$^{C2}$S—, —CR$^{C1}$R$^{C2}$O—, —SCR$^{C1}$R$^{C2}$—, —OCR$^{C1}$R$^{C2}$—, —RC=CR— or a single bond, which is bound adjacent the first bridge group on both groups so as to form an optionally substituted $C_{5-7}$ ring fused to both the first phenyl group and the second phenyl group, the first phenyl group being further optionally substituted;
$R^{C1}$ and $R^{C2}$ are independently selected from hydrogen, an optionally substituted $C_{1-7}$ alkyl group and an optionally substituted $C_{5-20}$ aryl group;
wherein the first phenyl group in $R^3$ optionally bears a substituent selected from the group consisting of acylamido, sulfonamino, and acyl; and
wherein the second phenyl group in $R^3$ optionally bears a substitutent selected from the group consisting of acylamido, sulfonamino, ether, ester, amido, and acyl;
wherein the acylamido has an acyl substituent which is formula (III):

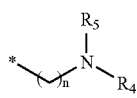

wherein n is 1 to 4, and $R_5$ and $R_4$ independently represent hydrogen, and optionally substituted $C_{1-7}$ alkyl, or $C_{5-20}$ aryl, or may together form, along with the nitrogen atom to which they are attached, an optionally substituted hetrocyclic piperazine, piperidine, or pyrrolidine.

9. An ATM inhibiting compound of formula I:

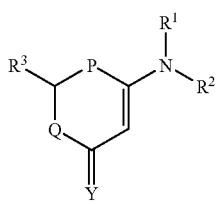

and isomers, salts, solvates, chemically protected forms, and prodrugs thereof, wherein:
one of P and Q is O, and the other of P and Q is CH, where there is a double bond between whichever of Q and P is CH and the carbon atom bearing the $R^3$ group;
Y is either O or S;
$R^1$ and $R^2$ together form, along with the nitrogen atom to which they are attached, a morpholino group;
$R^3$ is a first phenyl group, attached by a first bridge group selected from —S—, —S(=O)—, —S(=O)$_2$—, —O—, or —CR$^{C1}$R$^{C2}$— to an optionally substituted second phenyl group;

the first phenyl group and the second phenyl group being optionally further linked by a second bridge group selected from —S—, —S(=O)—, —S(=O)$_2$—, —O—, CR$^{C1}$R$^{C2}$—, —CR$^{C1}$R$^{C2}$CR$^{C1}$R$^{C2}$—, —C=O, —CR$^{C1}$R$^{C2}$S—, —CR$^{C1}$R$^{C2}$O—, —SCR$^{C1}$R$^{C2}$—, —OCR$^{C1}$R$^{C2}$—, —RC=CR—, or a single bond, which is bound adjacent the first bridge group on both groups so as to form an optionally substituted C$_{5-7}$ ring fused to both the first phenyl group and the second phenyl group, the first phenyl group being further optionally substituted;

R$^{C1}$ and R$^{C2}$ are independently selected from hydrogen, an optionally substituted C$_{1-7}$ alkyl group and an optionally substituted C$_{5-20}$ aryl group;

wherein the first phenyl group in R$^3$ optionally bears a substituent selected from the group consisting of an amino group, a hydroxy group, a halo group, an acylamido group, a sulfonamino group, an alkoxy group, an acylkoxy group, an alkyl group, a nitro group, a cyano group, a thiol group, an alkylthio group, and an acyl group; and wherein the second phenyl group in R$^3$ optionally bears a substitutent selected from the group consisting of an acylamido group, an ester group, an amido group, an amino group, an acyl group, a sulfonamino group, an ether group, and a carboxy group.

* * * * *